(12) United States Patent
Diwu et al.

(10) Patent No.: US 12,169,166 B2
(45) Date of Patent: Dec. 17, 2024

(54) FLUOROGENIC CYANINE COMPOUNDS FOR DETECTING NUCLEIC ACIDS

(71) Applicant: AAT Bioquest, Inc., Pleasanton, CA (US)

(72) Inventors: Zhenjun Diwu, Sunnyvale, CA (US); Haitao Guo, Sunnyvale, CA (US); Lok N. Neupane, Mountain View, CA (US); Deven Patel, Sunnyvale, CA (US)

(73) Assignee: AAT BIOQUEST, INC., Pleasanton, CA (US)

( * ) Notice: Subject to any disclaimer, the term of this patent is extended or adjusted under 35 U.S.C. 154(b) by 702 days.

(21) Appl. No.: 17/176,847

(22) Filed: Feb. 16, 2021

(65) Prior Publication Data

US 2022/0260464 A1   Aug. 18, 2022

(51) Int. Cl.
*G01N 1/30* (2006.01)
*C07D 417/06* (2006.01)
*C09B 23/01* (2006.01)
*C09B 23/10* (2006.01)
*G01N 21/64* (2006.01)

(52) U.S. Cl.
CPC ............ *G01N 1/30* (2013.01); *C07D 417/06* (2013.01); *C09B 23/0075* (2013.01); *C09B 23/105* (2013.01); *G01N 21/6428* (2013.01); *G01N 2001/302* (2013.01); *G01N 2021/6439* (2013.01)

(58) Field of Classification Search
None
See application file for complete search history.

(56) References Cited

U.S. PATENT DOCUMENTS

| | | | |
|---|---|---|---|
| 4,883,867 A | 11/1989 | Lee et al. | |
| 5,321,130 A | 6/1994 | Yue et al. | |
| 5,410,030 A | 4/1995 | Yue et al. | |
| 5,436,134 A | 7/1995 | Haugland et al. | |
| 5,658,751 A | 8/1997 | Yue et al. | |
| 5,863,753 A | 1/1999 | Haugland et al. | |
| 7,776,529 B2 | 8/2010 | Dallwig et al. | |
| 9,696,310 B2 * | 7/2017 | Margulies | G01N 33/53 |
| 2010/0041045 A1 | 2/2010 | Rueck et al. | |

FOREIGN PATENT DOCUMENTS

| | | |
|---|---|---|
| EP | 1668162 B1 | 4/2009 |
| WO | WO 95/01341 A1 | 1/1995 |
| WO | WO 2014/102803 A1 | 7/2014 |

OTHER PUBLICATIONS

Grant & Hackh's Chemical Dictionary (5th Ed. 1987) at p. 148.*

* cited by examiner

*Primary Examiner* — Po-Chih Chen
(74) *Attorney, Agent, or Firm* — Brennan A. Murphy; Glenn J. Foulds; Fenwick & West LLP

(57) ABSTRACT

This disclosure provides cyanine dye compounds having linked hydrogen bond-forming groups that can be used for detecting nucleic acids, particularly for fluorescent staining of DNA, in a biological sample. We found that the simultaneous incorporation of at least two hydrogen bond-forming groups (HBGs) into such a nucleic acid stain can provide for crosslinking interactions between the stain and the target nucleic acid, and lead to a significant increase in the detection sensitivity without substantially increasing undesirable cytotoxicity or mutagenicity properties of the dye compounds. The cyanine dye compounds can have a cyanine structure that connects two particular fused heterocycle ring systems, where at least two HBGs are connected to the core structure through linkers. Also provided are nucleic acid complexes including the cyanine dye compounds, and methods of using the compounds to detect nucleic acids in a biological sample.

22 Claims, 8 Drawing Sheets

FIG. 4A
FIG. 4B
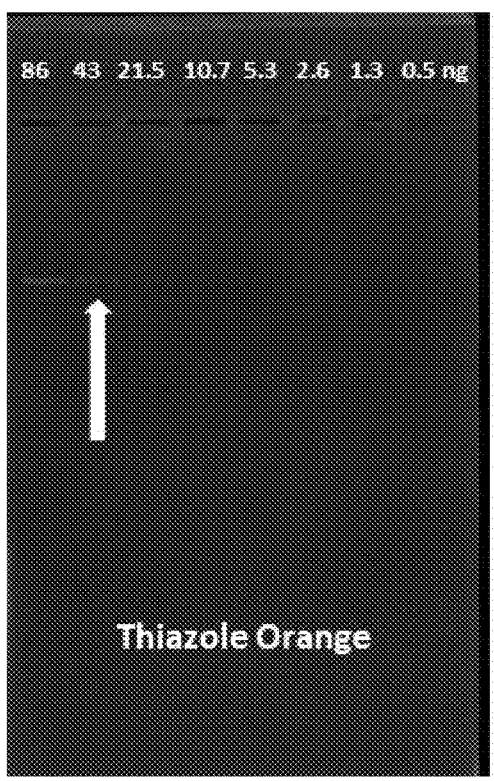
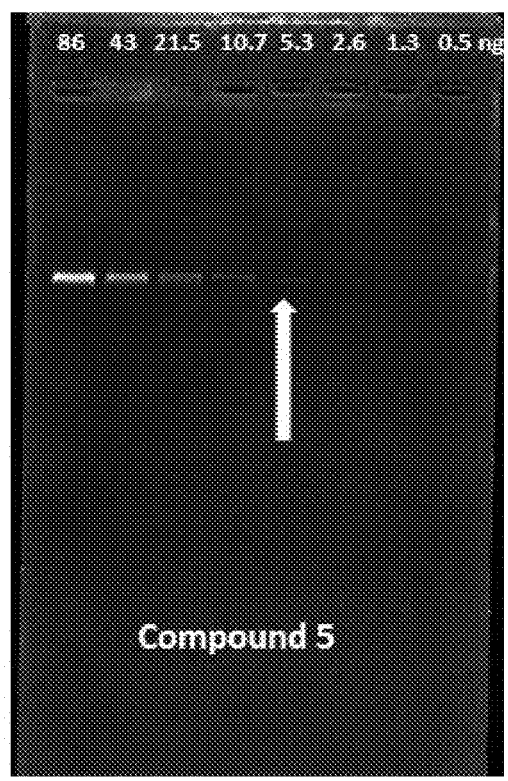

FIG. 5A
FIG. 5B
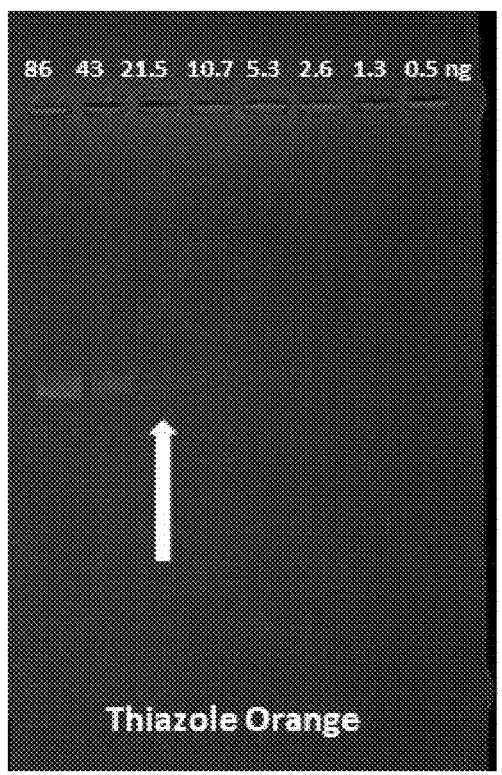
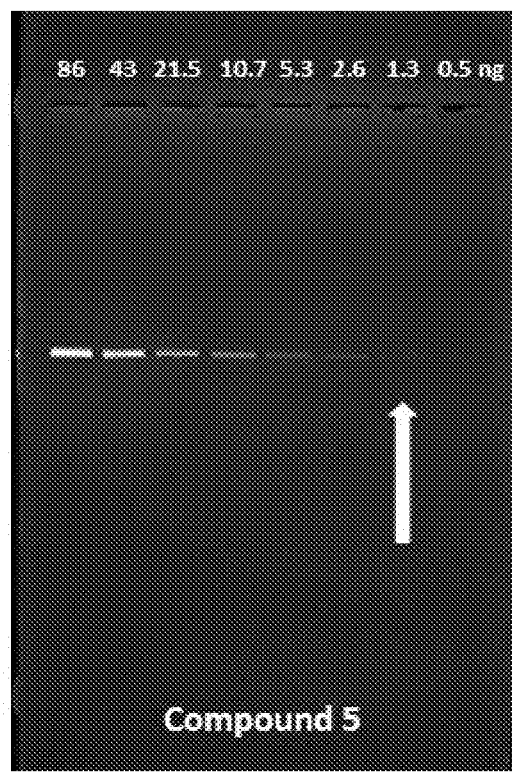

FLUOROGENIC CYANINE COMPOUNDS FOR DETECTING NUCLEIC ACIDS

FIELD OF THE DISCLOSURE

The present disclosure relates to cyanine compounds useful for staining nucleic acids, including DNA. The invention has applications in the fields of molecular biology, particularly with respect to fluorescence-based assays.

INTRODUCTION

In many fields of life sciences research, including biological, biomedical, genetic, fermentation, aquaculture, agricultural, forensic and environmental research, there is a need to detect nucleic acids (in particular DNA). In general, the detection methodology should be fast, sensitive, and selective. Such applications may also be required to detect minute amounts of nucleic acids in a variety of samples.

Some fluorescent nucleic acid stains are particularly sensitive because the fluorescence of the dye increases by several orders of magnitude upon binding to a nucleic acid. An early fluorescent nucleic acid stain was Thiazole Orange (see e.g., Lee et al. U.S. Pat. No. 4,883,867), a cyanine dye. Over the years, modifications to Thiazole Orange have led to the development of improved cyanine dyes for detecting nucleic acids, e.g., SYBR Green (see e.g., Stephen T. Yue et al., U.S. Pat. Nos. 5,321,130; 5,410,030; 5,436,134; 5,658,751 and 5,863,753). These modified Thiazole Orange analogs can bind nucleic acids more tightly than Thiazole Orange and can have increased water solubility and sensitivity (see e.g., Matthew P. Beaudet et al., EP1,668,162; Stephen T. Yue et al., U.S. Pat. Nos. 5,321,130 and 5,410,030; Jason Alfred Dallwig et al., U.S. Pat. No. 7,776,529; Alexander Rueck et al., US Appl. 2010/0041045).

Despite such improvements, many existing cyanine-based nucleic acid stains suffer from potent cytotoxicity and/or high mutagenicity, and are less friendly to users and the environment.

Nucleic acid stains that have low intrinsic fluorescence but form highly fluorescent complexes upon binding nucleic acid would be useful for the detection of nucleic acids on a solid support, such as an electrophoresis gel, in which sensitive nucleic acid detection depends largely upon a high signal to noise ratio. Furthermore, the spectral properties of such highly fluorescent nucleic acid stains should be such that these stains can be detected with commonly used detection devices. More importantly, these dyes should have minimal cytotoxicity and mutagenicity with maximum sensitivity for detecting nucleic acids. Unfortunately, many existing techniques used to enhance the DNA detection sensitivity lead to increased cytotoxicity and mutagenicity in biological systems.

Highly sensitive fluorescent nucleic acid stains that have minimal cytotoxicity and mutagenicity with maximum sensitivity for detecting nucleic acids, in particular detecting DNA, in a variety of biological samples are of interest.

SUMMARY

This disclosure provides cyanine dye compounds having linked hydrogen bond-forming groups that can be used for detecting nucleic acids, particularly for fluorescent staining of DNA, in a biological sample. We found that the simultaneous incorporation of at least two hydrogen bond-forming groups (HBGs) into such a nucleic acid stain can provide for crosslinking interactions between the stain and the target nucleic acid, and lead to a significant increase in the detection sensitivity without substantially increasing undesirable cytotoxicity or mutagenicity properties of the dye compounds.

The cyanine dye compounds can have a cyanine structure that connects two particular fused heterocycle ring systems, where at least two HBGs are connected to the core structure through linkers. Also provided are nucleic acid complexes including the cyanine dye compounds, and methods of using the compounds to detect nucleic acids in a biological sample.

In a first aspect, the cyanine dye compound of this disclosure has Formula 1a or 1b:

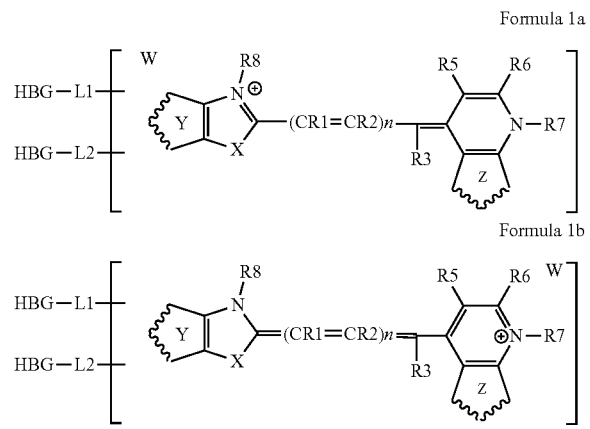

wherein:

each HBG is independently a hydrogen bonding group;

Y and Z are each independently an optionally substituted monocyclic or multicyclic fused ring system (e.g., one, two or more fused 5- and/or 6-membered rings, such as optionally substituted aryl or optionally substituted heteroaryl rings);

n is 0, 1, 2, or 3;

X is O, S, NH, NR10, Se, C(R20)R21, Si(R20)R21, PH, PR20, or (=O)R20;

R1-R3 are independently selected from hydrogen, halogen, cyano, carboxy, optionally substituted alkyl, optionally substituted alkoxy, optionally substituted aryloxy, optionally substituted aryl, optionally substituted heteroaryl, SR10, NHR10, NR10R11, -L1-HBG, and -L2-HBG;

R5 and R6 are independently selected from hydrogen, optionally substituted alkyl, halogen, carboxy, optionally substituted alkoxy, optionally substituted aryloxy, thiol, optionally substituted alkylthiol, optionally substituted arylthiol, azido, nitro, nitroso, cyano, amino, OH, a phosphonyl, a sulfonyl, a carbonyl, a boronyl, optionally substituted aryl, optionally substituted heteroaryl, -L1-HBG, and -L2-HBG, or R5 and R6 are cyclically linked to provide an optionally substituted monocyclic or bicyclic fused ring system (e.g., one or two fused 5- or 6-membered optionally substituted aryl or optionally substituted heteroaryl rings);

R7, R8, R10, R11, R20 and R21 are each independently selected from hydrogen, optionally substituted alkyl, optionally substituted alkenyl, optionally substituted alkynyl, optionally substituted aryl, optionally substituted heteroaryl, -L1-HBG, and -L2-HBG; and L1 and L2 are each independently a linker; and W is an optional counterion;

wherein each HBG moiety is independently connected to one of R1-R21, X, Y and Z through the linker L1 or L2.

BRIEF DESCRIPTION OF THE DRAWINGS

A detailed description of various aspects, features and embodiments is provided herein with reference to the accompanying drawings, which are briefly described below. The drawings are illustrative and are not necessarily drawn to scale. The drawings illustrate various aspects or features and may illustrate one or more embodiment(s) or example(s) in whole or in part. A reference numeral, letter, and/or symbol that are used in one drawing to refer to a particular element or feature may be used in another drawing to refer to a like element or feature.

FIG. 1A shows the absorption spectrum of Thiazole Orange (5 ug/ml) in Tris Buffer (pH=8.0). FIG. 1B shows the absorption spectrum of Compound 4 (5 ug/ml) in Tris Buffer (pH=8.0). Compounds 5, 6, 7 and 10 have similar absorption spectra to that of Compound 4.

FIGS. 4A-4B show a representation of pre-cast DNA gel staining with Compound 5 versus Thiazole Orange. Serial dilutions of a DNA sample (86, 43, 21.5, 10.7, 5.3, 2.6, 1.3, 0.5 ng/lane) are detected with Thiazole Orange or Compound 5. Compound 5 can clearly detect 5.3 ng DNA while TO can only detect 43 ng. Compounds 4, 6, 7 and 10 also demonstrate significantly higher sensitivity for detecting DNA on a gel than TO under the same conditions.

FIGS. 5A-5B show a representation of post-DNA gel staining with Compound 5 versus Thiazole Orange. Serial dilutions of a DNA sample (86, 43, 21.5, 10.7, 5.3, 2.6, 1.3, 0.5 ng/lane) are detected with Thiazole Orange or Compound 5. Compound 5 can clearly detect 1.3 ng DNA while TO can only detect 21.5 ng. Compounds 4, 6, 7 and 10 also demonstrate significantly higher sensitivity for detecting DNA on gel than TO under the same conditions.

DEFINITIONS

Figure 1A:
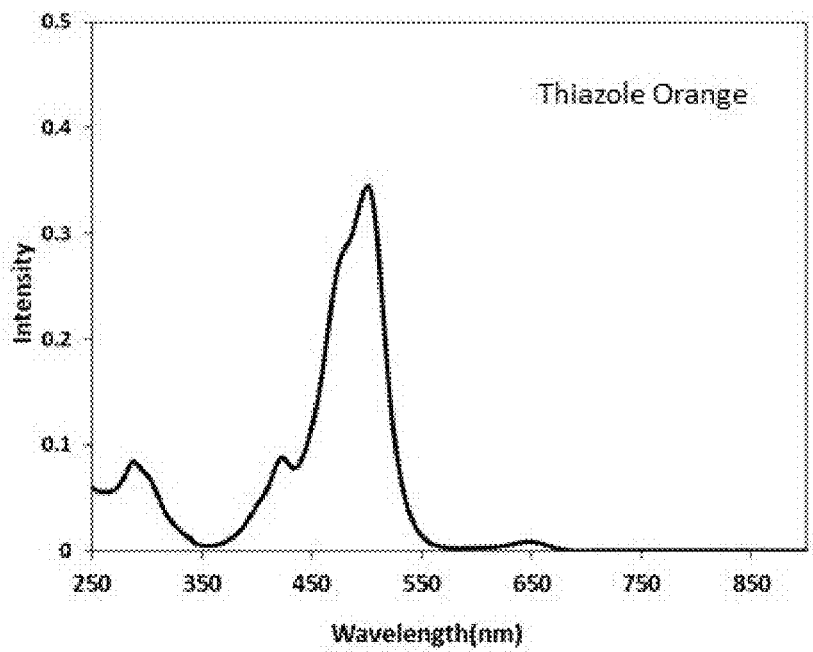
FIGS. 1A-1B show the absorbance spectra of Thiazole Orange and Compound 4.

The following definitions are set forth to illustrate and define the meaning and scope of the various terms used to describe the invention herein.

The term "alkyl," as used herein, by itself or as part of another group, refers to straight, branched chain or cyclic radicals having up to 50 carbons and 10 heteroatoms, unless the chain length or ring size is limited thereto, such as methyl, ethyl, propyl, cyclopropyl, isopropyl, butyl, t-butyl, isobutyl, pentyl, hexyl, cyclohexyl, isohexyl, heptyl, 4,4-dimethylpentyl, octyl, 2,2,4-trimethylpentyl, nonyl, and decyl, among others. The alkyl moieties may be substituted or contain other moieties including but not limited to carbonyl, ester, urea, urethane, sulfonamide, sulfone, or amide groups.

The term "alkylene" as employed herein, by itself or as part of another group, refers to straight, branched chain or cyclic divalent radicals having up to 50 carbons, unless the chain length or ring size is limited thereto. Typical examples include methylene (—CH$_2$—), ethylene (—CH$_2$CH$_2$—), propylene, butylene, pentylene, hexylene, heptylene, octylene, nonylene, and decylene, among others.

The term "alkenyl," as used herein, by itself or as part of another group, means a straight, branched chain or cyclic radical having 2-50 carbon atoms and one or more carbon-carbon double bonds, unless the chain length or ring size is limited thereto, such as ethenyl, 1-propenyl, 2-propenyl, 2-methyl-1-propenyl, 1-butenyl, and 2-butenyl, among others. The alkenyl chain may be 2 to 10 carbon atoms in length. Alternatively, the alkenyl chain may be 2 to 4 carbon atoms in length.

The term "alkenylene," as used herein, by itself or as part of another group, means straight, branched chain or cyclic divalent radical having 2-50 carbon atoms, unless the chain length or ring size is limited thereto, said straight, branched chain or cyclic radical containing at least one carbon-carbon double bond. Typical examples include ethenylene (—CH=CH—), propenylene (—CH=CHCH$_2$— and —CH$_2$CH=CH—), n-butenylene, and 3-methyl-2-pentenylene, hexenylene, heptenylene, octenylene, nonenylene, and decenylene, among others.

The term "alkynyl," as used herein, by itself or as part of another group, means a straight, branched chain or cyclic radical of 2-50 carbon atoms, unless the chain length or ring size is limited thereto, having at least one carbon-carbon triple bond between two of the carbon atoms in the chain, such as acetylenyl, 1-propynyl, and 2-propynyl, among others. The alkynyl chain may be 2 to 10 carbon atoms in length. Alternatively, the alkynyl chain may be from 2 to 4 carbon atoms in length.

The term "alkynylene" as used herein, by itself or as part of another group, means a straight, branched chain or cyclic divalent radical having 2-50 carbon atoms, unless the chain length or ring size is limited thereto, that contains at least one carbon-carbon triple bond. Typical examples include ethynylene (—C≡C—), propynylene (—C≡CCH$_2$— and —CH$_2$C≡C—), n-butynylene, 4-methyl-2-pentynylene, 1-butynylene, 2-butynylene, 3-butynylene, 4-butynylene, pentynylene, hexynylene, heptynylene, octynylene, nonynylene, and decynylene, among others.

The term "alkoxy" as used herein, by itself or as part of another group, refers to any of the above radicals linked via an oxygen atom. Typical examples include methoxy, ethoxy, isopropyloxy, sec-butyloxy, n-butyloxy, t-butyloxy, n-pentyloxy, 2-methylbutyloxy, 3-methylbutyloxy, n-hexyloxy, and 2-ethylbutyloxy, among others. Alkoxy also may include polyethylene glycol (PEG) groups (—OCH$_2$CH$_2$O—) or alkyl moieties that contain more than one oxygen atom. The alkoxy moieties may be substituted or contain other moieties including but not limited to carbonyl, ester or amide groups.

The term "aryl," as employed herein, by itself or as part of another group, refers to an aryl or aromatic ring system containing 1 to 4 unsaturated rings (each ring containing 6 conjugated carbon atoms and no heteroatoms) that are optionally fused to each other or bonded to each other by carbon-carbon single bonds, that is optionally further substituted as described below. Examples of aryl ring systems include, but are not limited to, substituted or unsubstituted derivatives of phenyl, biphenyl, o-, m-, or p-terphenyl, 1-naphthyl, 2-naphthyl, 1-, 2-, or 9-anthryl, 1-, 2-, 3-, 4-, or 9-phenanthrenyl and 1-, 2- or 4-pyrenyl. Aryl substituents may include phenyl, substituted phenyl, naphthyl or substituted naphthyl. The aryl moieties may be substituted or contain other moieties including but not limited to carbonyl, ester, urea, urethane, sulfonamide, sultone, or amide groups.

The term "arylene," as employed herein, by itself or as part of another ring, refers to an aryl or aromatic ring system containing 1 to 4 unsaturated rings (each ring containing 6 conjugated carbon atoms and no heteroatoms) that are optionally fused to each other or bonded to each other by carbon-carbon single bonds, that is optionally further substituted as described below. Examples of aryl ring systems include, but are not limited to, substituted or unsubstituted derivatives of phenylene, biphenylene, o-, m-, or p-terphenylene, 1-naphthylene, 2-naphthylene, 1-, 2-, or 9-anthrylene, 1-, 2-, 3-, 4-, or 9-phenanthrenylene and 1-, 2- or 4-pyrenylene. Arylene substituents may include phenylene, substituted phenylene, naphthylene or substituted naphthylene. The arylene moieties may be substituted or contain other moieties including but not limited to carbonyl, ester, urea, urethane, sulfonamide, sultone, or amide groups.

The term "heteroaryl," as employed herein, by itself or as part of another group, refers to groups having 5 to 14 ring atoms; 6, 10 or 14 π electrons shared in a cyclic array; and containing carbon atoms and 1, 2, 3, or 4 oxygen, nitrogen or sulfur heteroatoms (where examples of heteroaryl groups are: thienyl, benzo[b]thienyl, naphtho[2,3-b]thienyl, thianthrenyl, furyl, pyranyl, isobenzofuranyl, benzoxazolyl, chromenyl, xanthenyl, phenoxathiinyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalazinyl, naphthyridinyl, quinazolinyl, cinnolinyl, pteridinyl, carbazolyl, phenanthridinyl, acridinyl, perimidinyl, phenanthrolinyl, phenazinyl, isothiazolyl, phenothiazinyl, isoxazolyl, furazanyl, phenoxazinyl, and tetrazolyl groups). The heteroaryl moieties may be substituted or contain other moieties including but not limited to carbonyl, ester, urea, urethane, sulfonamide, sultone, or amide groups.

The term "heteroarylene," as employed herein, by itself or as part of another ring, refers to groups having 5 to 14 ring atoms; 6, 10 or 14 π electrons shared in a cyclic array; and containing carbon atoms and 1, 2, 3, or 4 oxygen, nitrogen or sulfur heteroatoms (where examples of heteroaryl groups are: thienylene, benzo[b]thienylene, naphtho[2,3-b]thienylene, thianthrenylene, furylene, pyranylene, isobenzofuranylene, benzoxazolylene, chromenylene, xanthenylene, phenoxathiinylene, 2H-pyrrolylene, pyrrolylene, imidazolylene, pyrazolylene, pyridylene, pyrazinylene, pyrimidinylene, pyridazinylene, ndolizinylene, isoindolylene, 3H-indolylene, indolylene, indazolylene, purinylene, 4H-quinolizinylene, isoquinolylene, quinolylene, phthalazinylene, naphthyridinylene, quinazolinylene, cinnolinylene, pteridinylene, carbazolylene, phenanthridinylene, acridinylene, perimidinylene, phenanthrolinylene, phenazinylene, isothiazolylene, phenothiazinylene, isoxazolylene, furazanylene, phenoxazinylene, and tetrazolylene rings). The heteroarylene moieties may be substituted or contain other moieties including but not limited to carbonyl, ester, urea, urethane, sulfonamide, sultone, or amide groups.

Any aryl, arylene, heteroaryl or heteroarylene ring system is unsubstituted or optionally and independently substituted by any synthetically accessible and chemically stable combination of substituents, such as H, halogen, cyano, sulfo, alkali or ammonium salt of sulfo, nitro, carboxy, alkyl, perfluoroalkyl, alkoxy, alkylthio, amino, monoalkylamino, dialkylamino or alkylamido, the alkyl portions of which having 18 or fewer carbons.

The terms "halogen" or "halo" as employed herein, by itself or as part of another group, refers to chlorine, bromine, fluorine or iodine.

The terms "amino" or "amine" include NH$_2$, "monoalkylamine" or "monoalkylamino," and "dialkylamine" or "dialkylamino". The terms "monoalkylamine" and "monoalkylamino," "dialkylamine" and "dialkylamino as employed herein, by itself or as part of another group, refers to the group NH$_2$ where one hydrogen has been replaced by an alkyl group, as defined above.

The terms "dialkylamine" and "dialkylamino" as employed herein, by itself or as part of another group, refers to the group NH$_2$ where both hydrogens have been replaced by alkyl groups, as defined above.

The term "hydroxyalkyl," as employed herein, by itself or as part of another group, refers to an alkyl group where one or more hydrogens thereof are substituted by one or more hydroxyl moieties.

The term "haloalkyl," as employed herein, by itself or as part of another group, refers to an alkyl group where one or more hydrogens thereof are substituted by one or more halo moieties. Typical examples include chloromethyl, fluoromethyl, difluoromethyl, trifluoromethyl, trichloroethyl, trifluoroethyl, fluoropropyl, and bromobutyl, among others.

The term "haloalkenyl," as employed herein, by itself or as part of another group, refers to an alkenyl group where one or more hydrogens thereof are substituted by one or more halo moieties.

The term "haloalkynyl," as employed herein, by itself or as part of another group, refers to an alkynyl group where one or more hydrogens thereof are substituted by one or more halo moieties.

The term "carboxyalkyl," as employed herein, by itself or as part of another group, refers to an alkyl group where one or more hydrogens thereof are substituted by one or more carboxylic acid moieties.

The term "heteroatom" as used herein, by itself or as part of another group, means an oxygen atom ("O"), a sulfur atom ("S") or a nitrogen atom ("N"). It will be recognized that when the heteroatom is nitrogen, it may form an $NR_1R_2$ moiety, where $R_1$ and $R_2$ are, independently from one another, hydrogen or alkyl, or together with the nitrogen to which they are bound, form a saturated or unsaturated 5-, 6-, or 7-membered ring.

The terms "stain" and "dye" may be used interchangeably, and refer to an aromatic molecule capable of absorbing light in the spectral range of from about 250 nm to about 1000 nm, inclusive. The term "dye" may refer to a fluorescent dye, a non-fluorescent dye, or both. The term "fluorescent dye" refers to a dye capable of emitting light when excited by another light of appropriate wavelength.

The terms "nucleic acid" refers to double-stranded DNA (dsDNA), single-stranded DNA (ssDNA), double-stranded RNA (dsRNA), single-stranded RNA (ssRNA), and/or derivatives thereof. A nucleic acid may be natural or synthetic.

The terms "complex" refers to a substance in which a dye is associated with another molecule (in particular, nucleic acids) in which at least one dye is present as a complex. Dyes and their ligands, e.g., DNA, are associated in a variety of forces, such as, hydrogen bonding, coordination bonding, static charge interaction, and/or hydrophobic interaction etc.

The terms "fluorescent nucleic acid stain" or "fluorescent nucleic acid dye" refers to a dye capable of binding to a nucleic acid to form a fluorescent dye-nucleic acid complex. A fluorescent nucleic acid dye is typically non-fluorescent or weakly fluorescent by itself, but becomes highly fluorescent upon nucleic acid binding. The term "fluorescent DNA dye" refers to a dye that becomes fluorescent upon binding to DNA.

The terms "fluorogenic" refers to the property or behavior of a compound (e.g., a dye or stain) that is weakly fluorescent or not fluorescent but can generate a stronger or enhanced fluorescence typically by an action (e.g., binding to nucleic acids).

The terms "counterion (e.g., W)" refers to a biologically compatible ion that is stable and synthetically accessible. Examples of counterion include, among others, chloride, bromide, iodide, sulfate, phosphate, perchlorate, tetrafluoroborate, nitrate, trifluoroacetate and anions of aromatic or aliphatic carboxylic acids, etc.

DETAILED DESCRIPTION

Cyanine Compounds

The present disclosure is directed to fluorogenic cyanine compounds which are useful as optically detectable nucleic acid probes, and can be applied for the detection, discrimination and quantification of a variety of biological targets and events. Embodiments of the present disclosure provide nucleic acid reporter or probe compounds having at least two hydrogen bonding group (HBG) moieties at a physiological pH. These reporter or probe compounds find use as nucleic acid stains, particularly for the fluorescent detection of DNA. In some embodiments, the compounds of this disclosure are fluorogenic and include at least HBG which provide for desirable properties in the biological sample, such as low cytotoxicity and low mutagenicity.

The term hydrogen bonding group moiety or "HBG," by itself or as part of another group, refers to a first group that is capable of forming a hydrogen bond with a second compatible HBG group to which it is in proximity. A hydrogen bond is a primarily electrostatic interaction between a hydrogen (H) atom which is covalently bound to a electronegative atom (e.g., O or N) or group of one HBG, i.e., the hydrogen bond donor, and another electronegative atom having a lone pair of electrons of another HBG, i.e., the hydrogen bond acceptor. In some embodiments, the HBG of the compound of this disclosure is the hydrogen bond donor. In some embodiments, the HBG of the compound of this disclosure is the hydrogen bond acceptor. It is understood that, in some cases, the HGB includes an electronegative atom that is covalently bonded to a hydrogen atom, which electronegative atom is itself capable of acting as a hydrogen bond donor or acceptor. In some embodiments, the HBG is a moiety or group that includes a H atom bonded to such an electronegative atom (e.g., O or N). In some embodiments, the HBG is a moiety or group that includes an electronegative atom that is capable of acting as only a hydrogen bond acceptor (e.g., the oxygen atom of a carbonyl containing group C=O). In some embodiments, the HBG is a moiety that includes a group selected from OH, amino (e.g., a primary amino —$NH_2$ or a secondary amino group), an amide (e.g., —$CONH_2$), a urea (e.g., —$NHCONH_2$), thiourea (e.g., —$NHCSNH_2$), a sulfonamide group (e.g., —$SO_2NH_2$), sulfonamide (e.g., —$SO_2NH_2$), —$NHSO_2CH_3$, —$NHSO_2CH_2F$, —$NHSO_2CHF_2$, and —$NHSO_2CF_3$.

In one aspect of the invention, the compounds of the invention may be described by Formula 1a:

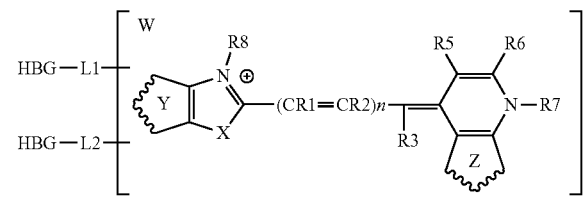

Formula 1a where the compound includes at least two linked hydrogen bonding groups (HBG).

The HBG groups can be connected via a linker to the core cyanine dye structure of the compound at any convenient positions of the structure. It is understood that the linker(s) may be incorporated into a substituent group of the compound and attached as a variety of positions. The position of attachment can be selected so that desirable optical properties of the compound (e.g., as described herein) are retained. In some embodiments, the cyanine compound of Formula 1a includes three, four, or more linked HBGs.

In some embodiments of Formula 1a, Y and Z are each independently an optionally substituted monocyclic or multicyclic fused ring system. The fused ring or fused ring system (Y) is fused to the adjacent five membered heterocyclic ring of Formula 1a to form a first heterocyclic multicyclic ring system. The fused ring or fused ring system (Z) is fused to the adjacent six membered heterocyclic ring of Formula 1a to form a second heterocyclic multicyclic ring system. Y and Z can be composed of one, two or more fused 5- and/or 6-membered rings, such as optionally substituted aryl and/or optionally substituted heteroaryl rings.

In some embodiments of Formula 1a, each HBG is independently a hydrogen bonding group (e.g., as described herein); Y and Z are each independently an optionally substituted monocyclic or multicyclic fused ring system (e.g., one, two or more fused 5- and/or 6-membered rings, such as optionally substituted aryl or optionally substituted heteroaryl rings);

n is 0, 1, 2, or 3;

X is O, S, NH, NR10, Se, C(R20)R21, Si(R20)R21, PH, PR20, or P(=O)R20;

R1-R3 are independently selected from hydrogen, halogen, cyano, carboxy, optionally substituted alkyl, optionally substituted alkoxy, optionally substituted aryloxy, optionally substituted aryl, optionally substituted heteroaryl, SR10, NHR10, NR10R11, -L1-HBG, and -L2-HBG;

R5 and R6 are independently selected from hydrogen, optionally substituted alkyl, halogen, carboxy, optionally substituted alkoxy, optionally substituted aryloxy, thiol, optionally substituted alkylthiol, optionally substituted arylthiol, azido, nitro, nitroso, cyano, amino, OH, a phosphonyl, a sulfonyl, a carbonyl, a boronyl, optionally substituted aryl, optionally substituted heteroaryl, -L1-HBG, and -L2-HBG, or R5 and R6 are cyclically linked to provide an optionally substituted monocyclic or bicyclic fused ring system (e.g., one or two fused 5- or 6-membered optionally substituted aryl or optionally substituted heteroaryl rings);

R7, R8, R10, R11, R20 and R21 are each independently selected from hydrogen, optionally substituted alkyl, optionally substituted alkenyl, optionally substituted alkynyl, optionally substituted aryl, optionally substituted heteroaryl, -L1-HBG, and -L2-HBG; and L1 and L2 are each independently a linker; and W is an optional counterion (e.g., none or a physiologically acceptable counterion);

wherein each HBG moiety is independently connected to one of R1-R21, X, Y and Z through the linker L1 or L2.

In some embodiments, the compound of Formula 1a may exist in a tautomeric form of Formula 1b or coexist with a tautomeric form of Formula 1b:

Formula 1b

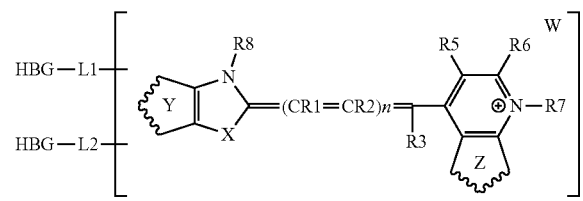

wherein each HBG is independently a hydrogen bonding group;

Y and Z are each independently an optionally substituted monocyclic or multicyclic fused ring system (e.g., one, two or more fused 5- and/or 6-membered rings, such as optionally substituted aryl or optionally substituted heteroaryl rings);

n is 0, 1, 2, or 3;

X is O, S, NH, NR10, Se, C(R20)R21, Si(R20)R21, PH, PR20, or P(=O)R20;

R1-R3 are independently selected from hydrogen, halogen, cyano, carboxy, optionally substituted alkyl, optionally substituted alkoxy, optionally substituted aryloxy, optionally substituted aryl, optionally substituted heteroaryl, SR10, NHR10, NR10R11, -L1-HBG, and -L2-HBG;

R5 and R6 are independently selected from hydrogen, optionally substituted alkyl, halogen, carboxy, optionally substituted alkoxy, optionally substituted aryloxy, thiol, optionally substituted alkylthiol, optionally substituted arylthiol, azido, nitro, nitroso, cyano, amino, OH, a phosphonyl, a sulfonyl, a carbonyl, a boronyl, optionally substituted aryl, optionally substituted heteroaryl, -L1-HBG, and -L2-HBG, or R5 and R6 are cyclically linked to provide an optionally substituted monocyclic or bicyclic fused ring system (e.g., one or two fused 5- or 6-membered optionally substituted aryl or optionally substituted heteroaryl rings);

R7, R8, R10, R11, R20 and R21 are each independently selected from hydrogen, optionally substituted alkyl, optionally substituted alkenyl, optionally substituted alkynyl, optionally substituted aryl, optionally substituted heteroaryl, -L1-HBG, and -L2-HBG; and L1 and L2 are each independently a linker; and W is an optional counterion;

wherein each HBG moiety is independently connected to one of R1-R21, X, Y and Z through the linker L1 or L2.

The terms "linker", "linking moiety" and "linking group" are used interchangeably and refer to a linking moiety that covalently connects two or more moieties, groups or compounds, such as a HBG and the core structure of a cyanine dye compound. In some cases, the linker is divalent and connects two moieties. In certain cases, the linker is a branched linking group that is trivalent (e.g., linking one cyanine dye compound to two HBGs), or of a higher multivalency. In some cases, the linker that connects the two or more moieties has a linear or branched backbone of 100 atoms or less, such as 80 atoms or less, 60 atoms or less, 50 atoms or less, 40 atoms or less, 30 atoms or less, or even 20 atoms or less) in length, e.g., as measured between the two or more moieties. A linking moiety may be a covalent bond that connects two groups, or a linear or branched chain of between 1 and 500 atoms in length, for example of about 1, 2, 3, 4, 5, 6, 8, 10, 12, 14, 16, 18, 20, 30, 40, 50, 100, 150, 200, 300, 400 or 500 carbon atoms in length, where the linker may be linear, branched, cyclic or a single atom. In certain cases, one, two, three, four, five or more, ten or more, or even more carbon atoms of a linker backbone may be optionally substituted with heteroatoms, e.g., sulfur, nitrogen and/or oxygen heteroatom. In certain instances, when the linker includes a polyethylene glycol (PEG) group, every third atom of that segment of the linker backbone is substituted with an oxygen atoms. The bonds between backbone atoms may be saturated or unsaturated, usually not more than one, two, or three unsaturated bonds will be present in a linker backbone. The linker may include one or more substituent groups, for example an alkyl, aryl or alkenyl group. A linker may include, without limitations, one or more of the following: oligo(ethylene glycol), ether, thioether, disulfide, amide, carbonate, carbamate, secondary amine, tertiary amine, alkyl which may be straight or branched, e.g., methyl, ethyl, n-propyl, 1-methylethyl (isopropyl), n-butyl, n-pentyl, 1,1-dimethylethyl (t-butyl), and the like. The linker backbone may include a cyclic group, for example, an aryl, a heterocycle, a cycloalkyl group or a heterocycle group, where 2 or more atoms, e.g., 2, 3 or 4 atoms, of the cyclic group are included in the backbone. The linker may contain at least one of heteroatoms N, O, or S, e.g. polyethylene glycol (PEG), which may be the same or different. In some embodiments, the linker is a covalent linkage having 1-100 non-hydrogen atoms selected from the group consisting of C, N, O, P, and S and is composed of any combination of single, double, triple or aromatic carbon-carbon bonds, carbon-nitrogen bonds, nitrogen-nitrogen bonds, carbon-oxygen bonds, carbon-sulfur bonds, phosphorus-oxygen bonds, and phosphorus-nitrogen bond.

Linking groups and linker units that can find use in linkers of this disclosure include, but are not limited to, amino acid residue(s), PEG units, terminal-modified PEG (e.g., —NH$(CH_2)_mO[(CH_2)_2O]_n(CH_2)_pCO$— linking groups where m is 2-6, p is 1-6 and n is 1-50, such as 1-12 or 1-6), C2-C12 alkyl or substituted C2-C12alkyl linkers, succinyl (e.g., —COCH$_2$CH$_2$CO—) units, diaminoethylene units (e.g., —NRCH$_2$CH$_2$NR— wherein R is H, alkyl or substituted alkyl) and combinations thereof, e.g., connected via linking functional groups such as amide, sulfonamide, carbamate, ether, thioether, ester, thioester, amino (—NH—) and the like. The linking component can be peptidic, e.g., a linker including a sequence of amino acid residues. The linking component can be a linker of formula -$(L^1)_a$-$(L^2)_b$-$(L^3)_c$-$(L^4)_d$-$(L^5)_e$-, where $L^1$ to $L^5$ are each independently a linker unit, and a, b, c, d and e are each independently 0 or 1, wherein the sum of a, b, c, d and e is 1 to 5. Other linkers are also possible (e.g., described herein).

In some embodiments, L1 and L2 are independently selected from optionally substituted alkyl and polyethylene glycol (e.g., PEG$_{n2}$ wherein n2 is 1 to 10, such as 1 to 6, or 1 to 3). In some embodiments, L1 and L2 each independently comprise one or more linking components selected from a single covalent bond, (C1-C6)alkyl, —CH$_2$CH$_2$O—, —OCH$_2$CH$_2$—, PEG$_{n2}$ wherein n2 is 1 to 10 (e.g., such as 1 to 6, or 1 to 3), —CONH—, —N(—)—, —NH—, —N(CH$_3$)—, —N$^+$(CH$_3$)$_2$—, —O—, —S—, —SO$_2$NH—, —NHSO$_2$—.

In some embodiments, L1 and L2 are each a linear linker. In some embodiments, at least one of L1 and L2 is a branched linker. In some embodiments, both of L1 and L2 is a branched linker. When L1 and/or L2 is a branched linker, it is understood that two or more HBG groups may be connected to the cyanine compounds via the branched linker. In some instances, the branched linker is connected to two HBGs.

In some embodiments L1 and L2 are independently

—[(CH$_2$)$_q$]$_p$-Q-(CH$_2$)$_m$— wherein:
each q and m are independently 0 to 10 (e.g., 0 to 6 or 1 to 6);
p is 1 or 2, wherein:
when p is 1, Q is selected from O, S, NH, N, CONH, NHCO, —NR31C(O)—, —CONR31, and N$^+$(R31)$_2$, wherein R31 is hydrogen or (C1-C6)alkyl; and
when p is 2, Q is N.

Specific examples of linking moieties which can comprise the linker L1 and L2 optionally include substituted or unsubstituted polymethylene, substituted or unsubstituted aryl, substituted or unsubstituted heteroaryl, substituted or unsubstituted arylene, substituted or unsubstituted alkylarylene and substituted or unsubstituted arylene-alkyl. In yet another embodiment, L1 and/or L2 include a thioether linkage. In yet another embodiment, L1 and L2 are independently a PEG linkage.

Specific examples of aryl ring systems include substituted or unsubstituted phenyl, biphenyl, naphthyl, anthryl, phenanthrenyl or pyrenyl.

Specific examples of heteroaryl ring systems include substituted or unsubstituted thienyl, benzothienyl, naphthothienyl, furyl, pyranyl, isobenzofuranyl, benzoxazolyl, chromenyl, xanthenyl, phenoxathiinyl, pyrrolyl, imidazolyl, pyrazolyl, pyridyl, pyrazinyl, pyrimidinyl, indolyl, purinyl, quinolyl, phthalazinyl, naphthyridinyl, quinazolinyl, cinnolinyl, carbazolyl, phenanthridinyl, acridinyl, phenazinyl, thiazolyl, oxazolyl, furazanyl, phenoxazinyl, or tetrazolyl.

Specific examples of arylene ring systems include substituted or unsubstituted phenylene, biphenylene, naphthylene, anthrylene, phenanthrenylene or pyrenylene.

Specific examples of heteroarylene ring systems include substituted or unsubstituted thienylene, benzothienylene, naphthothienylene, furylene, pyranylene, isobenzofuranylene, benzoxazolylene, chromenylene, xanthenylene, phenoxathiinylene, pyrrolylene, imidazolylene, pyrazolylene, pyridylene, pyrazinylene, pyrimidinylene, indolylene, purinylene, quinolylene, phthalazinylene, naphthyridinylene, quinazolinylene, cinnolinylene, carbazolylene, phenanthridinylene, acridinylene, phenazinylene, thiazolylene, oxazolylene, furazanylene, phenoxazinylene, or tetrazolylene.

Specific examples of physiological counter ions which can be included in salt forms of the cyanine compounds of this disclosure include, but are not limited to, fluoride, chloride, bromide, iodide, sulfate, sulfite, bisulfite, thiosulfate, phosphate, hydrogen phosphate, dihydrogen phosphate, thiophosphate, phosphite, nitrate, nitrite, borate, tetrafluoroborate, chlorate, chlorite, hypochlorite, perchlorate, carbonate, bicarbonate, formate, oxalate, acetate, trifluoroacetate, mesylate, tosylate, triflate, or thiocyanate, etc.

In some embodiments of Formula 1a to 1b, Y and Z are independently optionally substituted fused benzene or optionally substituted fused naphthalene ring; n is 0, 1, or 2; X is O, S, NH or NR10; R1-R3 are independently hydrogen, optionally substituted alkyl or optionally substituted aryl; R5 and R6 are independently hydrogen, halogen, optionally substituted alkyl or optionally substituted aryl; R7 and R8 are independently optionally substituted alkyl; L1 and L2 are optionally substituted alkylene, a PEG or optionally substituted arylene; W is none or a physiologically acceptable counter ion, provided that there are at least two HBG independently connected to R1-R21, X, Y or Z through Linker L1 or L2.

In some embodiments of Formula 1a, the dye compound is described by Formula 2a:

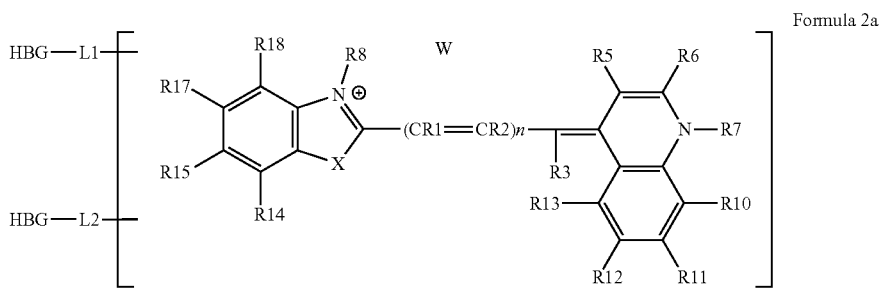

Formula 2a

In this embodiment, n is 0, 1, or 2; R1-R3 are independently selected from hydrogen, fluoro, chloro, carboxy, optionally substituted alkyl, optionally substituted alkoxy, optionally substituted aryloxy, optionally substituted aryl, optionally substituted heteroaryl, -L1-HBG, and -L2-HBG; R5, R6 and R10-R18 are independently selected from hydrogen, optionally substituted alkyl, halogen, carboxy, optionally substituted alkoxy, optionally substituted aryloxy, thiol, optionally substituted alkylthiol, optionally substituted arylthiol, azido, nitro, nitroso, cyano, amino, OH, a phosphonyl, a sulfonyl, a carbonyl, a boronyl, optionally substituted aryl, optionally substituted heteroaryl, -L1-HBG, and -L2-HBG; R7 and R8 are independently H, an alkyl, an alkenyl, an alkynyl, an aryl or a heteroaryl; W is a counterion; X is O, S, or NR20 wherein R20 is H, optionally substituted alkyl, optionally substituted alkenyl, optionally substituted alkynyl, optionally substituted aryl, or optionally substituted heteroaryl; L1 and L2 are independently a covalent linkage having 1-100 non-hydrogen atoms selected from the group consisting of C, N, O, P, and S and is composed of any combination of single, double, triple or aromatic carbon-carbon bonds, carbon-nitrogen bonds, nitrogen-nitrogen bonds, carbon-oxygen bonds, carbon-sulfur bonds, phosphorus-oxygen bonds, and phosphorus-nitrogen bond; each HBG moiety is independently selected from —OH, amino (e.g., —NH$_2$), amide (e.g., —CONH$_2$), —NHCOCH$_3$, urea (e.g., —NHCONH$_2$), thiourea (e.g., —NHCSNH$_2$), sulfonamide (e.g., —SO$_2$NH$_2$), —NHSO$_2$CH$_3$, —NHSO$_2$CH$_2$F, —NHSO$_2$CHF$_2$, and —NHSO$_2$CF$_3$, provided that there are at least two HBG moieties are independently connected to R1-R18, X, Y or Z through Linker L1 or L2.

Formula 2a may exist in a tautomeric form of Formula 2b or coexist with a tautomeric form Formula 2b:

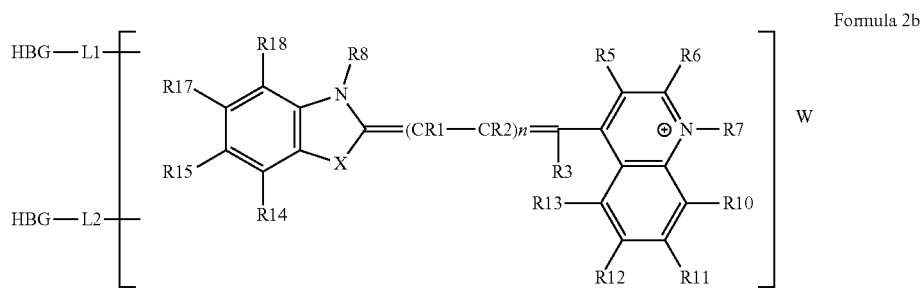

Formula 2b wherein n is 0, 1, or 2; R1-R3 are independently selected from hydrogen, fluoro, chloro, carboxy, optionally substituted alkyl, optionally substituted alkoxy, optionally substituted aryloxy, optionally substituted aryl, optionally substituted heteroaryl, -L1-HBG, and -L2-HBG; R5, R6 and R10-R18 are independently selected from hydrogen, optionally substituted alkyl, halogen, carboxy, optionally substituted alkoxy, optionally substituted aryloxy, thiol, optionally substituted alkylthiol, optionally substituted arylthiol, azido, nitro, nitroso, cyano, amino, OH, a phosphonyl, a sulfonyl, a carbonyl, a boronyl, optionally substituted aryl, optionally substituted heteroaryl, -L1-HBG, and -L2-HBG; R7 and R8 are independently H, an alkyl, an alkenyl, an alkynyl, an aryl or a heteroaryl; W is a counterion; X is O, S, or NR20 wherein R20 is H, optionally substituted alkyl, optionally substituted alkenyl, optionally substituted alkynyl, optionally substituted aryl, or optionally substituted heteroaryl; L1 and L2 are independently a covalent linkage having 1-100 non-hydrogen atoms selected from the group consisting of C, N, O, P, and S and is composed of any combination of single, double, triple or aromatic carbon-carbon bonds, carbon-nitrogen bonds, nitrogen-nitrogen bonds, carbon-oxygen bonds, carbon-sulfur bonds, phosphorus-oxygen bonds, and phosphorus-nitrogen bond; each HBG moiety is independently selected from —OH, amino (e.g., —NH$_2$), amide (e.g., —CONH$_2$), —NHCOCH$_3$, urea (e.g., —NHCONH$_2$), thiourea (e.g., —NHCSNH$_2$), sulfonamide (e.g., —SO$_2$NH$_2$), —NHSO$_2$CH$_3$, —NHSO$_2$CH$_2$F, —NHSO$_2$CHF$_2$, and —NHSO$_2$CF$_3$, provided that there are at least two HBG moieties are independently connected to R1-R18, X, Y or Z through Linker L1 or L2.

In some embodiments of Formula 2a-b, R1-R3 are independently H, optionally substituted alkyl, optionally substituted aryl or optionally substituted heteroaryl; R5, R6 and R10-R18 are independently H, optionally substituted alkyl, chloro, fluoro, carboxy, optionally substituted alkoxy, optionally substituted aryloxy, amino, OH, a boronyl, optionally substituted aryl or optionally substituted heteroaryl; R7 and R8 are independently H, optionally substituted alkyl, optionally substituted aryl or optionally substituted heteroaryl; W is chloride, iodide, sulfate, perchlorate and trifluoroacetate; X is O, S, or NR20 wherein R20 is H or optionally substituted alkyl; L1 and L2 are independently is optionally substituted alkylene, a PEG, optionally substituted arylene, or optionally substituted heteroarylene; each HBG moiety is independently selected from OH, NH$_2$, amide (e.g., —CONH$_2$), NHCOCH$_3$, sulfonamide (e.g., —SO$_2$NH$_2$), —NHSO$_2$CHF$_2$, and —NHSO$_2$CF$_3$.

In some embodiments of Formula 2a-b, R1-R3 are H; R5 and R6 are independently H, an alkyl, an aryl or a heteroaryl; R10-R18 are independently H, optionally substituted alkyl, chloro, fluoro, optionally substituted alkoxy, optionally substituted aryl or optionally substituted heteroaryl; R7 and R8 are independently optionally substituted alkyl; W is chloride, iodide, sulfate, perchlorate and trifluoroacetate; X is O, or S; L1 and L2 are independently is optionally substituted alkylene or a PEG; each HBG moiety is independently selected from OH, NH$_2$, amide (e.g., —CONH$_2$), NHCOCH$_3$, sulfonamide (e.g., —SO$_2$NH$_2$), —NHSO$_2$CHF$_2$, and —NHSO$_2$CF$_3$.

In some embodiments of formula 1a-1b, the compound is of formula 2a-2b:

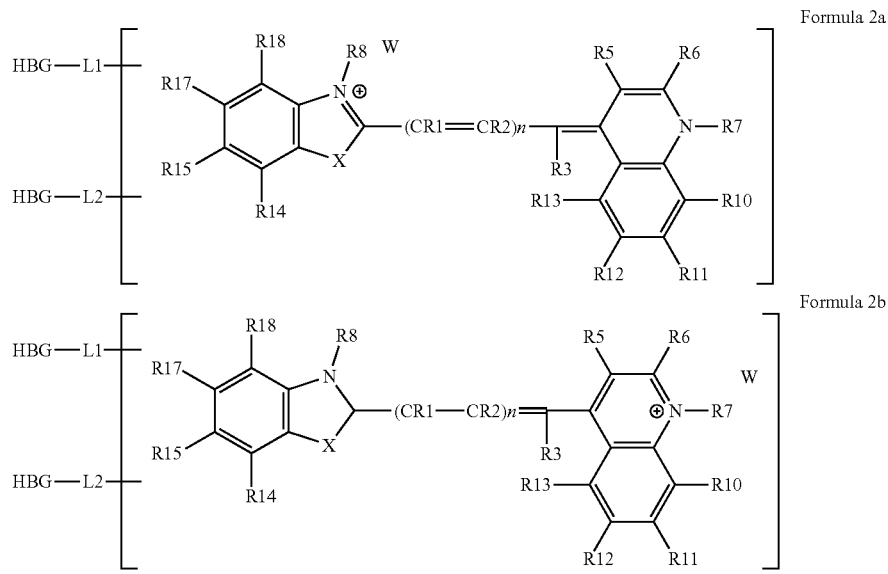

wherein:

n is 0, 1, 2 or 3;

R1-R3 are independently selected from hydrogen, fluoro, chloro, carboxy, optionally substituted alkyl, optionally substituted alkoxy, optionally substituted aryloxy, optionally substituted aryl, optionally substituted heteroaryl, -L1-HBG, and -L2-HBG;

R5 and R6 are cyclically linked to and together with the carbon atoms to which they are attached provide a fused benzene ring, or R5 and R6 are independently selected from hydrogen, optionally substituted alkyl, halogen, carboxy, optionally substituted alkoxy, optionally substituted aryloxy, thiol, optionally substituted alkylthiol, optionally substituted arylthiol, azido, nitro, nitroso, cyano, amino, OH, a phosphonyl, a sulfonyl, a carbonyl, a boronyl, optionally substituted aryl, optionally substituted heteroaryl, -L1-HBG, and -L2-HBG;

R14 and R15 are cyclically linked to and together with the carbon atoms to which they are attached provide a fused benzene ring, or R14 and R15 are independently selected from hydrogen, optionally substituted alkyl, halogen, carboxy, optionally substituted alkoxy, optionally substituted aryloxy, thiol, optionally substituted alkylthiol, optionally substituted arylthiol, azido, nitro, nitroso, cyano, amino, OH, a phosphonyl, a sulfonyl, a carbonyl, a boronyl, optionally substituted aryl, optionally substituted heteroaryl, -L1-HBG, and -L2-HBG;

R10-R13 and R16-R18 are independently selected from hydrogen, optionally substituted alkyl, halogen, carboxy, optionally substituted alkoxy, optionally substituted aryloxy, thiol, optionally substituted alkylthiol, optionally substituted arylthiol, azido, nitro, nitroso, cyano, amino, OH, a phosphonyl, a sulfonyl, a carbonyl, a boronyl, optionally substituted aryl, optionally substituted heteroaryl, -L1-HBG, and -L2-HBG;

R7 and R8 are independently H, an alkyl, an alkenyl, an alkynyl, an aryl or a heteroaryl; W is a counterion; X is O, S, or NR20 wherein R20 is H, optionally substituted alkyl, optionally substituted alkenyl, optionally substituted alkynyl, optionally substituted aryl, or optionally substituted heteroaryl; L1 and L2 are independently a covalent linkage having 1-100 non-hydrogen atoms selected from the group consisting of C, N, O, P, and S and is composed of any combination of single, double, triple or aromatic carbon-carbon bonds, carbon-nitrogen bonds, nitrogen-nitrogen bonds, carbon-oxygen bonds, carbon-sulfur bonds, phosphorus-oxygen bonds, and phosphorus-nitrogen bond; each HBG moiety is independently selected from —OH, amino (e.g., —NH$_2$), amide (e.g., —CONH$_2$), —NHCOCH$_3$, urea (e.g., —NHCONH$_2$), thiourea (e.g., —NHCSNH$_2$), sulfonamide (e.g., —SO$_2$NH$_2$), —NHSO$_2$CH$_3$, —NHSO$_2$CH$_2$F, —NHSO$_2$CHF$_2$, and —NHSO$_2$CF$_3$, provided that there are at least two HBG moieties are independently connected to R1-R18, X, Y or Z through Linker L1 or L2.

In some embodiments of Formula 2a-2b, R5 and R6 are cyclically linked to and together with the carbon atoms to which they are attached provide a fused benzene ring, and R14 and R15 are not cyclically linked.

In some embodiments of Formula 2a-2b, R14 and R15 are cyclically linked to and together with the carbon atoms to which they are attached provide a fused benzene ring, and R5 and R6 are not cyclically linked.

In some embodiments of Formula 2a-2b, the at least two HBG moieties are connected to R7 and R8 through Linker L1 or L2, respectively. In some embodiments of Formula 2a-2b, L1 and L2 are independently selected from

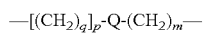

wherein:
each q and m are independently 0 to 10 (e.g., 0 to 6 or 1 to 6);
p is 1 or 2, wherein:
when p is 1, Q is selected from O, S, NH, N, CONH, NHCO, —NR31C(O)—, —CONR31, and N$^+$(R31)$_2$, wherein R31 is hydrogen or (C1-C6)alkyl; and
when p is 2, Q is N.

In some embodiments of Formula 2a-2b, each HBG is independently selected from —OH, amino (e.g., —NH$_2$), amide (e.g., —CONH$_2$), —NHCOCH$_3$, urea (e.g., —NHCONH$_2$), thiourea (e.g., —NHCSNH$_2$), sulfonamide (e.g., —SO$_2$NH$_2$), —NHSO$_2$CH$_3$, —NHSO$_2$CH$_2$F, —NHSO$_2$CHF$_2$, and —NHSO$_2$CF$_3$. In some embodiments of Formula 2a-2b, each HBG is independently —OH, or —NH$_2$.

In some embodiments of Formula 2a-2b, R6 is an optionally substituted aryl or optionally substituted heteroaryl. In some embodiments of Formula 2a-2b, R6 is selected from optionally substituted phenyl, optionally substituted pyridyl (e.g., 4-pyridyl), optionally substituted thiophenyl (e.g., 2-thienyl) and optionally substituted biphenyl.

In another aspect of the disclosure, the dye compound may be described by Formula 3a:

Formula 3a

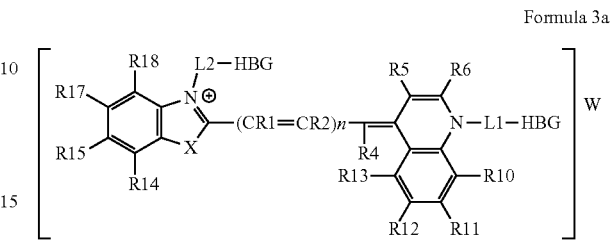

In this embodiment, n is 0, 1, or 2; R1-R3 are independently selected from hydrogen, optionally substituted alkyl, fluoro, chloro, carboxy, optionally substituted alkoxy, optionally substituted aryloxy, optionally substituted aryl, and optionally substituted heteroaryl; R5, R6 and R10-R18 are independently selected from hydrogen, optionally substituted alkyl, halogen, carboxy, optionally substituted alkoxy, optionally substituted aryloxy, thiol, optionally substituted alkylthiol, optionally substituted arylthiol, azido, nitro, nitroso, cyano, amino, OH, a phosphonyl, a sulfonyl, a carbonyl, a boronyl, optionally substituted aryl, and optionally substituted heteroaryl; X is O, S, or NR20 wherein R20 is selected from hydrogen, optionally substituted alkyl, optionally substituted alkenyl, optionally substituted alkynyl, optionally substituted aryl, and optionally substituted heteroaryl; each HBG moiety is independently selected from OH, NH$_2$, amide (e.g., —CONH$_2$), NHCOCH$_3$, sulfonamide (e.g., —SO$_2$NH$_2$), —NHSO$_2$CHF$_2$, and —NHSO$_2$CF$_3$; and W is a counterion.

Formula 3a may exist in a tautomeric form of Formula 3b or coexist with a tautomeric form of Formula 3b:

Formula 3b

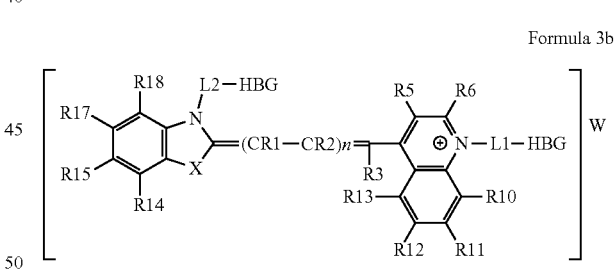

wherein n is 0, 1, or 2; R1-R3 are independently selected from hydrogen, optionally substituted alkyl, fluoro, chloro, carboxy, optionally substituted alkoxy, optionally substituted aryloxy, optionally substituted aryl, and optionally substituted heteroaryl; R5, R6 and R10-R18 are independently selected from hydrogen, optionally substituted alkyl, halogen, carboxy, optionally substituted alkoxy, optionally substituted aryloxy, thiol, optionally substituted alkylthiol, optionally substituted arylthiol, azido, nitro, nitroso, cyano, amino, OH, a phosphonyl, a sulfonyl, a carbonyl, a boronyl, optionally substituted aryl, and optionally substituted heteroaryl; X is O, S, or NR20 wherein R20 is selected from hydrogen, optionally substituted alkyl, optionally substituted alkenyl, optionally substituted alkynyl, optionally substituted aryl, and optionally substituted heteroaryl; each HBG moiety is independently selected from OH, NH$_2$, amide (e.g., —CONH$_2$), NHCOCH$_3$, sulfonamide (e.g., —SO$_2$NH$_2$), —NHSO$_2$CHF$_2$, and —NHSO$_2$CF$_3$; and W is a counterion.

In some embodiments of Formula 3a-b, R1-R3 are independently H, optionally substituted alkyl, optionally substituted aryl or optionally substituted heteroaryl; R5, R6 and R10-R18 are independently H, optionally substituted alkyl, chloro, fluoro, carboxy, optionally substituted alkoxy, optionally substituted aryloxy, an amino, OH, a boronyl, optionally substituted aryl or optionally substituted heteroaryl; W is chloride, iodide, sulfate, perchlorate and trifluoroacetate; X is O, S, or NR20 wherein R20 is H or optionally substituted alkyl; L1 and L2 are independently is optionally substituted alkylene, a PEG, optionally substituted aryl, or optionally substituted heteroaryl; each HBG moiety is independently OH, NH$_2$, an amide, or a sulfonamide group.

In some embodiments of Formula 3a-b, R1-R3 are H; R5 and R6 are independently H, optionally substituted alkyl, optionally substituted aryl or optionally substituted heteroaryl; R10-R18 are independently H, optionally substituted alkyl, chloro, fluoro, optionally substituted alkoxy, optionally substituted aryl or optionally substituted heteroaryl; R7 and R8 are independently optionally substituted alkyl; W is chloride, iodide, sulfate, perchlorate and trifluoroacetate; X is O, or S; L1 and L2 are independently is optionally substituted alkylene or a PEG; HBG moieties are independently OH, NH$_2$, an amide, or a sulfonamide group.

In some embodiments of formula 1a-2b, the compound is of formula 3a-3b:

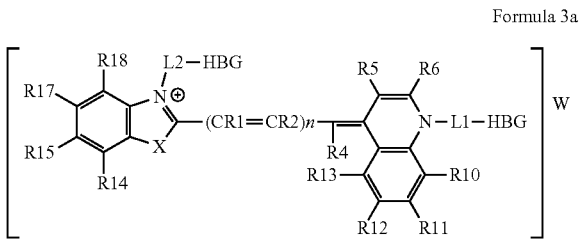

Formula 3a

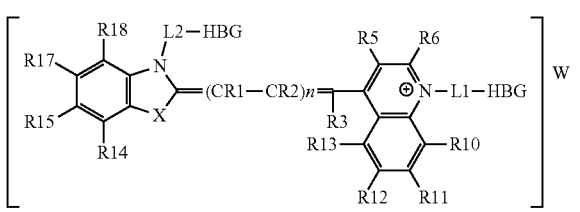

Formula 3b wherein:

n is 0, 1, 2 or 3;

R1-R3 are independently selected from hydrogen, fluoro, chloro, carboxy, optionally substituted alkyl, optionally substituted alkoxy, optionally substituted aryloxy, optionally substituted aryl, and optionally substituted heteroaryl;

R5 and R6 are cyclically linked to and together with the carbon atoms to which they are attached provide a fused benzene ring, or R5 and R6 are independently selected from hydrogen, optionally substituted alkyl, halogen, carboxy, optionally substituted alkoxy, optionally substituted aryloxy, thiol, optionally substituted alkylthiol, optionally substituted arylthiol, azido, nitro, nitroso, cyano, amino, OH, a phosphonyl, a sulfonyl, a carbonyl, a boronyl, optionally substituted aryl, and optionally substituted heteroaryl;

R14 and R15 are cyclically linked to and together with the carbon atoms to which they are attached provide a fused benzene ring, or R14 and R15 are independently selected from hydrogen, optionally substituted alkyl, halogen, carboxy, optionally substituted alkoxy, optionally substituted aryloxy, thiol, optionally substituted alkylthiol, optionally substituted arylthiol, azido, nitro, nitroso, cyano, amino, OH, a phosphonyl, a sulfonyl, a carbonyl, a boronyl, optionally substituted aryl, and optionally substituted heteroaryl;

R10-R13 and R16-R18 are independently selected from hydrogen, optionally substituted alkyl, halogen, carboxy, optionally substituted alkoxy, optionally substituted aryloxy, thiol, optionally substituted alkylthiol, optionally substituted arylthiol, azido, nitro, nitroso, cyano, amino, OH, a phosphonyl, a sulfonyl, a carbonyl, a boronyl, optionally substituted aryl, optionally substituted heteroaryl, -L1-HBG, and -L2-HBG;

R7 and R8 are independently H, an alkyl, an alkenyl, an alkynyl, an aryl or a heteroaryl; W is a counterion; X is O, S, or NR20 wherein R20 is H, optionally substituted alkyl, optionally substituted alkenyl, optionally substituted alkynyl, optionally substituted aryl, or optionally substituted heteroaryl;

L1 and L2 are independently a linker;

each HBG moiety is independently selected from —OH, amino (e.g., —NH$_2$), amide (e.g., —CONH$_2$), —NHCOCH$_3$, urea (e.g., —NHCONH$_2$), thiourea (e.g., —NHCSNH$_2$), sulfonamide (e.g., —SO$_2$NH$_2$), —NHSO$_2$CH$_3$, —NHSO$_2$CH$_2$F, —NHSO$_2$CHF$_2$, and —NHSO$_2$CF$_3$.

In some embodiments of Formula 3a-3b, R5 and R6 are cyclically linked to and together with the carbon atoms to which they are attached provide a fused benzene ring, and R14 and R15 are not cyclically linked.

In some embodiments of Formula 3a-3b, R14 and R15 are cyclically linked to and together with the carbon atoms to which they are attached provide a fused benzene ring, and R5 and R6 are not cyclically linked.

In some embodiments of Formula 3a-3b, L1 and L2 are independently selected from

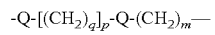

-Q-[(CH$_2$)$_q$]$_p$-Q-(CH$_2$)$_m$— wherein:

each q and m are independently 0 to 10 (e.g., 0 to 6 or 1 to 6);

p is 1 or 2, wherein:

when p is 1, each Q is independently selected from absent, O, S, NH, N, CONH, NHCO, —NR31C(O)—, —CONR31, and N$^+$(R31)$_2$, wherein R31 is hydrogen or (C1-C6)alkyl; and when p is 2, each Q is independently selected from absent and N.

In some embodiments of Formula 3a-3b, each HBG is independently selected from —OH, amino (e.g., —NH$_2$), amide (e.g., —CONH$_2$), —NHCOCH$_3$, urea (e.g., —NHCONH$_2$), thiourea (e.g., —NHCSNH$_2$), sulfonamide (e.g., —SO$_2$NH$_2$), —NHSO$_2$CH$_3$, —NHSO$_2$CH$_2$F, —NHSO$_2$CHF$_2$, and —NHSO$_2$CF$_3$. In some embodiments of Formula 3a-3b, each HBG is independently —OH, or —NH$_2$. In some embodiments of Formula 3a-3b, L1-HBG and L2-HBG are each independently —(CH$_2$)$_m$—OH or —(CH$_2$)$_m$—NH$_2$, where m is 1 to 6.

In some embodiments of Formula 3a-3b, R6 is an optionally substituted aryl or optionally substituted heteroaryl. In some embodiments of Formula 3a-3b, R6 is selected from optionally substituted phenyl, optionally substituted pyridyl (e.g., 4-pyridyl), optionally substituted thiophenyl (e.g., 2-thienyl) and optionally substituted biphenyl.

In any one of the embodiments described here, the cyanine dye compound includes HBGs that are hydrogen bond donor groups. In some embodiments, the HBG is selected from OH, and NH$_2$. In any one of the embodiments described here, the cyanine dye compound includes HBGs that include both a hydrogen bond donor and a hydrogen bond acceptor. In some embodiments, a HBG moiety is —CONH$_2$, —SO$_2$NH$_2$, NHCOCH$_3$, —NHSO$_2$CHF$_2$, and —NHSO$_2$CF$_3$.

In some embodiments of Formula 3a-3b:
R1-R3 are each hydrogen;
R5 and R6 are independently selected from hydrogen, optionally substituted alkyl, optionally substituted aryl, and optionally substituted heteroaryl;
R10-R18 are independently selected from hydrogen, optionally substituted alkyl, chloro, fluoro, optionally substituted alkoxy, optionally substituted aryl, and optionally substituted heteroaryl;
R7 and R8 are independently optionally substituted alkyl;
W is chloride, iodide, sulfate, perchlorate or trifluoroacetate;
X is O, or S;
L1 and L2 are independently is optionally substituted alkyl or a PEG;
each HBG moiety is independently selected from OH, NH$_2$, an amide, and sulfonamide.

In some embodiments of Formula 3a-3b:
n is 0, or 1;
R1-R3 are each H;
R6 is optionally substituted aryl or optionally substituted heteroaryl;
X is O or S;
each HBG moiety is independently selected from OH, NH$_2$, NHCOCH$_3$, —NHSO$_2$CHF$_2$, and —NHSO$_2$CF$_3$; and
L1 and L2 are independently —[(CH$_2$)$_q$]$_p$-Q-(CH$_2$)$_m$— wherein:
each q and m are independently 0 to 10 (e.g., 0 to 6 or 1 to 6);
p is 1 or 2, wherein:
when p is 1, Q is selected from O, S, NH, N, CONH, NHCO, —NR31C(O)—, —CONR31, and N$^+$(R31)$_2$, wherein R31 is hydrogen or (C1-C6)alkyl; and
when p is 2, Q is N.
In some embodiments of Formula 3a-3b, n is 0. In some embodiments of Formula 3a-3b, X is O. of Formula 3a-3b, each HBG moiety is independently selected from OH, and NH$_2$, of Formula 3a-3b, L1 and L2 are independently (C2-C6)alkylene (e.g., (C3-C5)alkylene, such as C3 or C4-alkylene).

In some embodiments of Formula 3a-3b, the compound is of Formula 4a or 4b:

Formula 4a

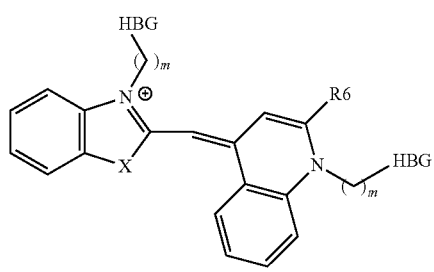

-continued

Formula 4b

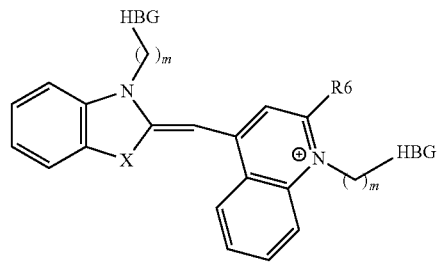

or a salt thereof (e.g., including counterion W),
wherein:
each m is independently 2 to 6;
X is O or S;
R6 is selected from optionally substituted phenyl, optionally substituted pyridyl (e.g., 4-pyridyl), optionally substituted thiophenyl (e.g., 2-thienyl) and optionally substituted biphenyl; and
each HBG is selected from OH, NH$_2$, NHCOCH$_3$, —NHSO$_2$CHF$_2$, and —NHSO$_2$CF$_3$.

In some embodiments of Formula 4a to 4b, m is 3 or 4. In some embodiments of Formula 4a to 4b, X is S. In some embodiments of Formula 4a to 4b, X is O. In some embodiments of Formula 4a to 4b, R6 is optionally substituted phenyl. In some embodiments of Formula 4a to 4b, HBG is selected from OH, and NH$_2$.

In some embodiments of Formula 1a to 4b, the cyanine dye compound is a compound as described in Table 1, or a salt thereof.

In some embodiments of Formula 4a to 4b, the compound is selected from:

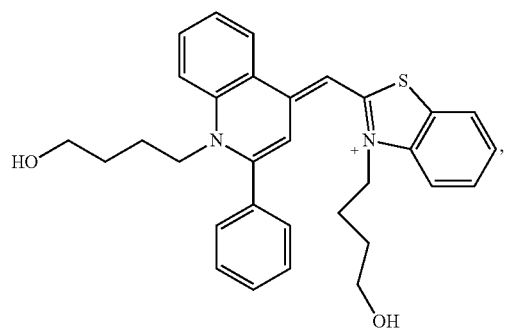

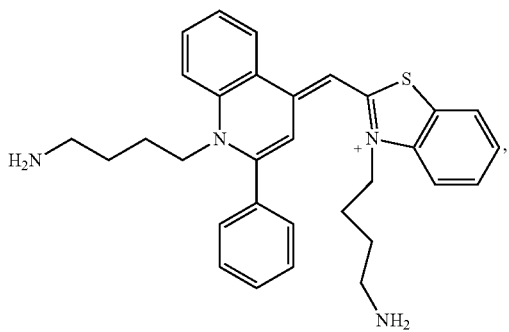

-continued

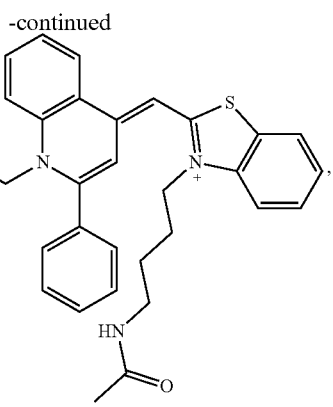

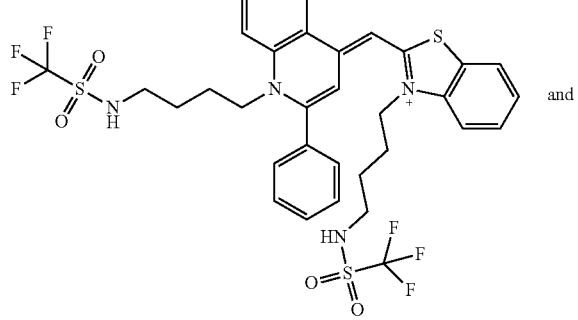
and

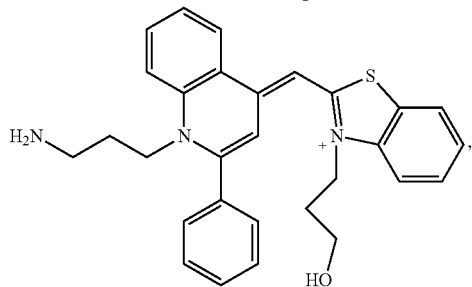

or a tautomer thereof, or a salt thereof.

The cyanine compounds of this disclosure can possess an overall electronic charge. It is to be understood that when such electronic charges are shown to be present, they are balanced by the presence of appropriate counterions, which may or may not be explicitly identified. A physiologically acceptable counterion, which is preferred for some applications, is not toxic in biological applications, and does not have a substantially deleterious effect on biomolecules. Counterions can be readily substituted using well known methods, such as ion-exchange chromatography, or selective precipitation. In some embodiments, where the cyanine compound is positively charged, the counterion is selected from, chloride, bromide, iodide, sulfate, alkanesulfonate, arylsulfonate, phosphate, perchlorate, tetrafluoroborate, tetraarylboride, nitrate and anions of aromatic or aliphatic carboxylic acids. In some embodiments, where the cyanine compound is negatively charged, the counterion is selected from alkali metal ions, alkaline earth metal ions, transition metal ions, ammonium or substituted ammonium and pyridinium ions.

It is to be understood that although the cyanine compounds of this disclosure may be depicted having a particular electronic resonance structure, other permitted resonance structures are meant to be encompassed by this disclosure and apply to all aspects of this disclosure described herein.

Aspects of this disclosure include conjugates of the cyanine compounds. The cyanine compounds can be conjugated to a wide variety of biological, organic or inorganic substances that contain or are modified to contain functional groups with suitable reactivity, resulting in chemical attachment of the conjugated substances.

In one embodiment, the conjugate contains at least one Linker-Biomolecule attached to the cyanine compound (e.g., as described herein). Biomolecules of interest include, but are not limited to, an amino acid, a peptide, a protein, a tyramine, a polysaccharide, an ion-complexing moiety, a nucleoside, a nucleotide, an oligonucleotide, a nucleic acid, a hapten, a psoralen, a drug, a hormone, a lipid, a lipid assembly, a polymer, a polymeric microparticle, a biological cell or virus. In some instances, the biomolecule is an antibody or antibody fragment.

In another embodiment, the conjugate contains at least one Linker-Polymeric Dye attached to the cyanine compound (e.g., as described herein), where the polymeric dye and the cyanine compound may be configured in proximity such that fluorescence resonance energy transfer is possible under favorable conditions. In certain embodiments, the covalent linkage attaching the cyanine compound to the biomolecule or polymeric dye contains multiple intervening atoms that serve as the Linker.

Fluorescent Complex

Aspects of this disclosure include complexes of the cyanine compounds and a nucleic acid.

The nucleic acid can be single stranded or double stranded. In some embodiments, the nucleic acid of the complex is DNA. In some embodiments, the nucleic acid of the complex is RNA.

The nucleic acid can be naturally occurring. In some embodiments, the nucleic acid is genomic DNA. In some embodiments, the nucleic acid is non-naturally occurring. In some embodiments, the nucleic acid is a synthetic DNA or RNA construct. In some embodiments, the nucleic acid is plasmid DNA.

The nucleic acids targeted for complexation can be obtained or derived from any convenient biological sample. In some embodiments, the biological sample containing the nucleic acid of interest is tissue, cells, blood, serum, plants, or a forensic sample. In some embodiments, the cyanine dye compounds of this disclosure have an absorption maximum wavelength in the range from about 300 nm to about 900 nm, however the dyes generally provide only a negligible fluorescence emission peak unless bound to a nucleic acid. Upon binding to nucleic acid (e.g., DNA or RNA), the optical properties of the dyes can change significantly. The fluorescence intensity of the dyes in the bound state is generally over 10-fold brighter than unbound state. In some embodiments, the fluorescence or absorption or emission wavelength maximum of the dye can shift upon binding to the target nucleic acid.

Methods

Aspects of this disclosure include methods of detecting a nucleic acid analyte in a sample. In some embodiments, when the dye is bound to a nucleic acid a detectable change of optical or spectral properties occurs which can be used to quantitatively or qualitatively detect, assess and/or analyze the presence and/or the amount of nucleic acids in a sample.

A detectable optical response means a change in, or occurrence of, an optical signal that is detectable either by observation or instrumentally. In some embodiments, the detectable response is a change in fluorescence, such as a change in the intensity, excitation or emission wavelength distribution of fluorescence, fluorescence lifetime, fluorescence polarization, or a combination thereof. The degree and/or location of staining, compared with a standard or expected response, indicates whether and to what degree the sample possesses a given characteristic.

In some embodiments, the method of detecting nucleic acids in a sample, comprises:
a) contacting a sample that contains, or is suspected of containing, a nucleic acid with a dye compound (e.g., as described herein);
b) incubating the contacted sample under conditions sufficient for the dye compound to associate with the nucleic acid, if present, in the sample to produce a fluorescent nucleic acid-dye complex; and
c) detecting, if present, a fluorescent signal of the nucleic acid-dye complex.

To detect or analyze the presence of nucleic acids in a sample, the dye in a buffered solution can be added to a sample thought to contain nucleic acids. The cyanine compounds can be used in an aqueous, mostly aqueous or aqueous-miscible solution prepared according to methods generally known in the art. The exact concentration of cyanine compound used is dependent upon the experimental conditions and the desired results. The optimal concentration is determined by systematic variation until satisfactory results with minimal background fluorescence are accomplished.

Measurement of fluorescence of the solution before and after the combination of the sample with nucleic acids are compared. The fluorescence intensity of the nucleic acid-dye complex is proportional to the amount of nucleic acid in the sample, which can be readily determined, e.g., by comparison to a standard curve.

In some embodiments, the change of fluorescence intensity can be used to qualitatively measure the activity of enzymes, such as DNAase that hydrolyze the nucleic acids, for example, and the changes of nucleic acids in a sample. The fluorescence of the solution containing dye and nucleic acids is compared with the fluorescence of the solution after the addition of a hydrolyzing enzyme.

In some embodiments, the dyes of this disclosure can be used as nucleic acid stains in cells. Because different dyes have different cell membrane permeability, the cell permeant dyes can be used for living cell stains, and the cell impermeant dyes can be used for dead or fixed cell stains. Besides, the dyes can be used to measure the viability of cells in the sample. Cell death or toxicity usually results in loss of cell membrane integrity. When the cell membrane is damaged, the nucleic acids inside the cell become accessible to the cell impermeant dyes. By choosing one dye that is cell permeant and another dye that is cell impermeant with different emission wavelengths, the live/dead cells can be differentiated based on fluorescence signals at two different emission wavelengths.

In some embodiments, techniques that permeabilize the plasma membrane, such as electroporation, shock treatments or high extracellular ATP can be used to introduce the cyanine dye compounds into cells for intracellular staining.

At any time after or during staining, the sample is illuminated with a wavelength of light selected to give a detectable optical response, and observed with a means for detecting the optical response. Equipment that is useful for illuminating the cyanine compounds of this disclosure includes, but is not limited to, hand-held ultraviolet lamps, mercury arc lamps, xenon lamps, lasers and laser diodes. These illumination sources are optionally integrated into laser scanners, transilluminators, fluorescence microplate readers, standard or minifluorometers, or chromatographic detectors.

The optical response is optionally detected by visual inspection, or by use of any of the following devices: CCD cameras, video cameras, photographic films, laser-scanning devices, fluorometers, photodiodes, quantum counters, epifluorescence microscopes, scanning microscopes, flow cytometers, fluorescence microplate readers, or by means for amplifying the signal such as photomultiplier tubes. Where the sample is examined using a flow cytometer, examination of the sample optionally includes sorting portions of the sample according to their fluorescence response.

In some embodiments, the intensity of fluorescence can be used to measure the effect of a cytotoxic event including exposure to a chemical reagent, the addition of a biological agent, or other change in environmental condition that results in membrane disruption. The effect of a cytotoxic event can be observed over time, or after a fixed period of time. To measure the effect of a cytotoxic event that involves the addition of a cytotoxic reagent, a stock solution of the reagent is prepared at a concentration greater that what is expected to be a toxic dose and this is added to the cells or tissue in a suitable medium. Typically, various concentrations of the reagent are added from 0 to greater than a toxic dose. Toxicity can be measured by the fluorescence intensity of cells after addition of the dyes.

In some embodiments, the dyes of this disclosure can be used for detection of nucleic acids immobilized relative to a matrix or a surface, or as nucleic acid gel stains. There are generally two methods for staining nucleic acids in gels using the dyes. The first method is post-gel staining, wherein a nucleic acid sample is separated by gel electrophoresis, the gel comprising the separated nucleic acids is incubated in a solution comprising the dye, the gel may be destained, if desirable or necessary to remove background fluorescence, and the resulting gel is viewed using a transilluminator or laser scanner. The second method is pre-cast gel staining, wherein a gel is premixed or pre-embedded with the dye, the nucleic acid sample is separated by electrophoresis using the pre-cast gel, and the stained gel is viewed using a transilluminator or laser scanner. In general, the dyes of this disclosure can be used for post-gel staining, pre-cast gel staining, or variations thereof.

Thus, aspects of this disclosure include a bioanalytical system (e.g., including one or more components as described above) that includes a fluorescent complex of target nucleic acid and cyanine compound of this disclosure. In some embodiments, the bioanalytical system is a gel electrophoresis system for separation and detection of target nucleic acids.

In some embodiments, the dyes of this disclosure may be included in a kit that facilitates the practice of various assays using any of the cyanine dyes or conjugates of this disclosure (e.g., as described herein). A kit may comprise the dye, information or a protocol regarding use of the dye or the kit, and/or other useful or necessary materials or reagents, such as any materials or reagents suitable for the detection of nucleic acids, for example, such as a buffer (e.g., incubation buffer or wash buffer), a detergent, a DNA or RNA standard, a DNA or RNA ladder, matrix materials, additional detection reagents, a purification medium, luminescence standards, enzymes, enzyme inhibitors, and/or organic solvent.

Additional Embodiments

In addition to the appended claims, the clauses provided below illustrate several embodiments of this disclosure. They are not intended to limit or define the entire scope of the invention.

Clause 1. A cyanine compound having Formula 1a or 1b:

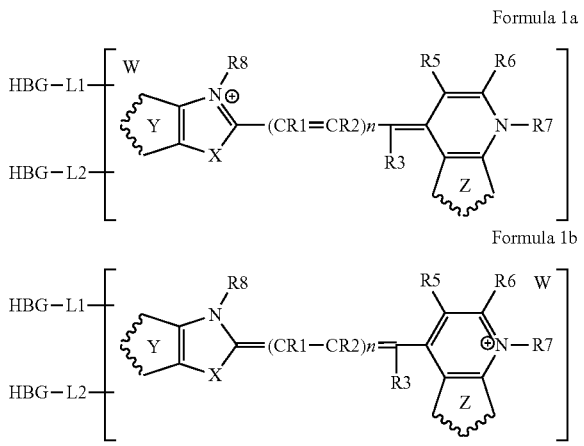

Formula 1a

Formula 1b wherein:
  each HBG is independently a hydrogen bonding group;
  Y and Z are each independently an optionally substituted monocyclic or multicyclic fused ring system (e.g., one, two or more fused 5- and/or 6-membered rings, such as optionally substituted aryl or optionally substituted heteroaryl rings);
  n is 0, 1, 2, or 3;
  X is O, S, NH, NR10, Se, C(R20)R21, Si(R20)R21, PH, PR20, or P(=O)R20;
  R1-R3 are independently selected from hydrogen, halogen, cyano, carboxy, optionally substituted alkyl, optionally substituted alkoxy, optionally substituted aryloxy, optionally substituted aryl, optionally substituted heteroaryl, SR10, NHR10, NR10R11, -L1-HBG, and -L2-HBG;
  R5 and R6 are independently selected from hydrogen, optionally substituted alkyl, halogen, carboxy, optionally substituted alkoxy, optionally substituted aryloxy, thiol, optionally substituted alkylthiol, optionally substituted arylthiol, azido, nitro, nitroso, cyano, amino, OH, a phosphonyl, a sulfonyl, a carbonyl, a boronyl, optionally substituted aryl, optionally substituted heteroaryl, -L1-HBG, and -L2-HBG, or R5 and R6 are cyclically linked to provide an optionally substituted monocyclic or bicyclic fused ring system (e.g., one or two fused 5- or 6-membered optionally substituted aryl or optionally substituted heteroaryl rings);
  R7, R8, R10, R11, R20 and R21 are each independently selected from hydrogen, optionally substituted alkyl, optionally substituted alkenyl, optionally substituted alkynyl, optionally substituted aryl, optionally substituted heteroaryl, -L1-HBG, and -L2-HBG; and
  L1 and L2 are each independently a linker; and
  W is an optional counterion;
wherein each HBG moiety is independently connected to one of R1-R21, X, Y and Z through the linker L1 or L2.

Clause 2. The compound according to clause 1, wherein the compound is configured to exhibit a 10-fold or greater fluorescence intensity increase upon binding to a DNA molecule (e.g., when irradiated with light at about the absorbance maximum of the compound).

Clause 3. The compound according to clause 1 or 2, wherein L1 and L2 are independently selected from optionally substituted polymethylene, optionally substituted aryl, optionally substituted heteroaryl, optionally substituted arylene, optionally substituted alkyl-arylene and optionally substituted arylene-alkyl.

Clause 4. The compound according to clause 1 or 2, wherein L1 and L2 are independently selected from optionally substituted alkyl and polyethylene glycol (e.g., $PEG_{n2}$ wherein n2 is 1 to 10, such as 1 to 6, or 1 to 3).

Clause 5. The compound according to any one of clauses 1 to 4, wherein L1 and L2 each independently comprise one or more linking components selected from a single covalent bond, (C1-C6)alkyl, —$CH_2CH_2O$—, —$OCH_2CH_2$—, $PEG_2$ wherein n2 is 1 to 6, —CONH—, —N(—)—, —NH—, —N($CH_3$)—, —$N^+(CH_3)_2$—, —O—, —S—, —$SO_2NH$—, —$NHSO_2$—.

Clause 6. The compound according to any one of clauses 1 to 5, wherein L1 and L2 are each linear linkers.

Clause 7. The compound according to any one of clauses 1 to 5, wherein at least one of L1 and L2 is a branched linker.

Clause 8. The compound according to any one of clauses 1 to 7, wherein L1 and L2 are independently —$[(CH_2)_q]_p$-Q-$(CH_2)_m$— wherein:
  each q and m are independently 0 to 10 (e.g., 0 to 6 or 1 to 6);
  p is 1 or 2, wherein:
    when p is 1, Q is selected from O, S, NH, N, CONN, NHCO, —NR31C(O)—, —CONR31, and $N^+(R31)_2$, wherein R31 is hydrogen or (C1-C6)alkyl; and
    when p is 2, Q is N.

Clause 9. The compound according to any one of clauses 1 to 8, wherein Y and Z are independently selected from optionally substituted benzene, optionally substituted biphenylene, optionally substituted naphthylene, optionally substituted anthrylene, optionally substituted phenanthrenylene and optionally substituted pyrenylene.

Clause 10. The compound according to any one of clauses 1 to 8, wherein Y and Z are independently selected from optionally substituted thienylene, optionally substituted benzothienylene, optionally substituted naphthothienylene, optionally substituted furylene, optionally substituted pyranylene, optionally substituted isobenzofuranylene, optionally substituted benzoxazolylene, optionally substituted chromenylene, optionally substituted xanthenylene, optionally substituted phenoxathiinylene, optionally substituted pyrrolylene, optionally substituted imidazolylene, optionally substituted pyrazolylene, optionally substituted pyridylene, optionally substituted pyrazinylene, optionally substituted pyrimidinylene, optionally substituted indolylene, optionally substituted purinylene, optionally substituted quinolylene, optionally substituted phthalazinylene, optionally substituted naphthyridinylene, optionally substituted quinazolinylene, optionally substituted cinnolinylene, optionally substituted carbazolylene, optionally substituted phenanthridinylene, optionally substituted acridinylene, optionally substituted phenazinylene, optionally substituted thiazolylene, optionally substituted oxazolylene, optionally substituted furazanylene, optionally substituted phenoxazinylene, and optionally substituted tetrazolylene.

Clause 11. The compound according any one of clauses 1 to 8, wherein Y and Z are independently optionally substituted fused benzene ring or optionally substituted fused naphthylene ring system.

Clause 12. The compound according any one of clauses 1 to 11, wherein n is 0, 1, or 2.
Clause 13. The compound according any one of clauses 1 to 12, wherein X is O, S, NH or NR10.
Clause 14. The compound according any one of clauses 1 to 13, wherein R1-R3 are independently selected from hydrogen, optionally substituted alkyl, and optionally substituted aryl.
Clause 15. The compound according any one of clauses 1 to 14, wherein R5 and R6 are independently selected from hydrogen, halogen, optionally substituted alkyl, and optionally substituted aryl.
Clause 16. The compound according any one of clauses 1 to 15, wherein R7 and R8 are independently optionally substituted alkyl.
Clause 17. The compound according any one of clauses 1 to 16, wherein L1 and L2 are independently selected from optionally substituted alkyl, a PEG, and optionally substituted aryl.
Clause 18. The compound according any one of clauses 1 to 17, wherein W is chloride, bromide, iodide, sulfate, trifluoroacetate, mesylate, tosylate, or triflate.
Clause 19. The compound according any one of clauses 1 to 18, wherein each HBG moiety is independently selected from —OH, amino (e.g., —NH$_2$), amide (e.g., —CONH$_2$), —NHCOCH$_3$, urea (e.g., —NHCONH$_2$), thiourea (e.g., —NHCSNH$_2$), sulfonamide (e.g., —SO$_2$NH$_2$), —NHSO$_2$CH$_3$, —NHSO$_2$CH$_2$F, —NHSO$_2$CHF$_2$, and —NHSO$_2$CF$_3$.
Clause 20. The compound of any one of clauses 1 to 8, wherein Y and Z are each independently an optionally substituted fused benzene ring, and wherein the compound has Formula 2a or 2b:

optionally substituted alkoxy, optionally substituted aryloxy, thiol, optionally substituted alkylthiol, optionally substituted arylthiol, azido, nitro, nitroso, cyano, amino, OH, a phosphonyl, a sulfonyl, a carbonyl, a boronyl, optionally substituted aryl, optionally substituted heteroaryl, -L1-HBG, and -L2-HBG;
X is O, S, or NR20; and
R7, R8, and R20 are independently selected from hydrogen, optionally substituted alkyl, optionally substituted alkenyl, optionally substituted alkynyl, optionally substituted aryl, and optionally substituted heteroaryl.
Clause 21. The compound according to clause 20, wherein each HBG moiety is independently selected from —OH, amino (e.g., —NH$_2$), amide (e.g., —CONH$_2$), —NHCOCH$_3$, urea (e.g., —NHCONH$_2$), thiourea (e.g., —NHCSNH$_2$), sulfonamide (e.g., —SO$_2$NH$_2$), —NHSO$_2$CH$_3$, —NHSO$_2$CH$_2$F, —NHSO$_2$CHF$_2$, and —NHSO$_2$CF$_3$.
Clause 22. The compound according to clause 20, wherein:
R1-R3 are independently selected from hydrogen, optionally substituted alkyl, optionally substituted aryl, and optionally substituted heteroaryl;
R5, R6 and R10-R18 are independently selected from hydrogen, optionally substituted alkyl, chloro, fluoro, carboxy, optionally substituted alkoxy, optionally substituted aryloxy, amino, OH, a boronyl, optionally substituted aryl, and optionally substituted heteroaryl;
R7 and R8 are independently H, optionally substituted alkyl, optionally substituted aryl or optionally substituted heteroaryl;
X is O, S, or NR20, wherein R20 is hydrogen or optionally substituted alkyl;

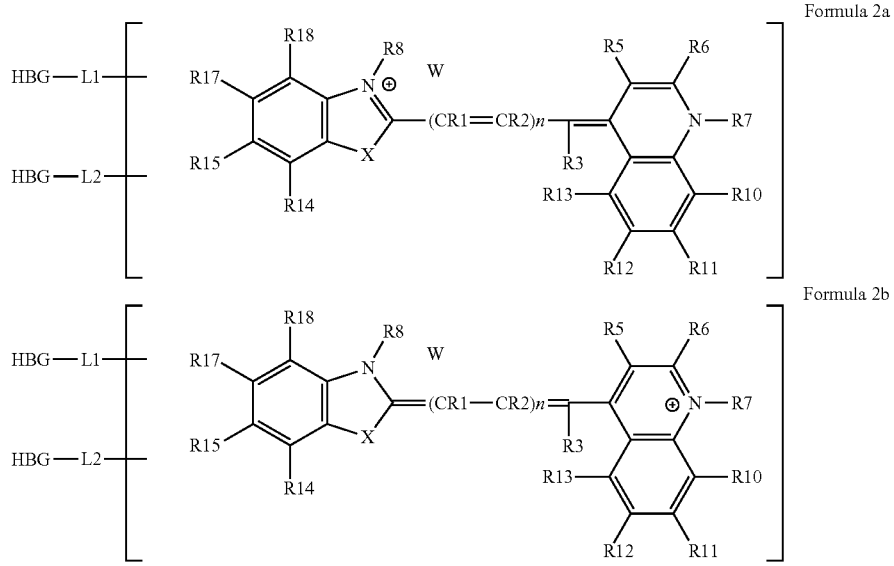

Formula 2a

Formula 2b wherein:
n is 0, 1, or 2;
R1-R3 are independently selected from hydrogen, fluoro, chloro, carboxy, optionally substituted alkyl, optionally substituted alkoxy, optionally substituted aryloxy, optionally substituted aryl, optionally substituted heteroaryl, -L1-HBG, and -L2-HBG;
R5, R6 and R10-R18 are independently selected from hydrogen, optionally substituted alkyl, halogen, carboxy, W is chloride, iodide, sulfate, perchlorate or trifluoroacetate;
L1 and L2 are independently selected from optionally substituted alkyl, a PEG, optionally substituted aryl, and optionally substituted heteroaryl; and
each HBG moiety is independently selected from OH, NH$_2$, amide (e.g., —CONH$_2$), NHCOCH$_3$, sulfonamide (e.g., —SO$_2$NH$_2$), —NHSO$_2$CHF$_2$, and —NHSO$_2$CF$_3$.

Clause 23. The compound according to any one of clauses 20 to 22, wherein:
R1-R3 are H;
R5 and R6 are independently selected from hydrogen, optionally substituted alkyl, optionally substituted aryl, and optionally substituted heteroaryl;
R10-R18 are independently selected from hydrogen, optionally substituted alkyl, chloro, fluoro, optionally substituted alkoxy, optionally substituted aryl, and optionally substituted heteroaryl;
R7 and R8 are independently selected from optionally substituted alkyl;
W is chloride, iodide, sulfate, perchlorate or trifluoroacetate;
X is O, or S;
L1 and L2 are independently is optionally substituted alkyl or a PEG;
each HBG moiety is independently selected from OH, $NH_2$, amide (e.g., —$CONH_2$), $NHCOCH_3$, sulfonamide (e.g., —$SO_2NH_2$), —$NHSO_2CHF_2$, and —$NHSO_2CF_3$.

Clause 24. The cyanine compound according to any one of clauses 1 to 8, wherein Y and Z are each independently an optionally substituted fused benzene ring, and wherein the compound has Formula 3a or 3b:

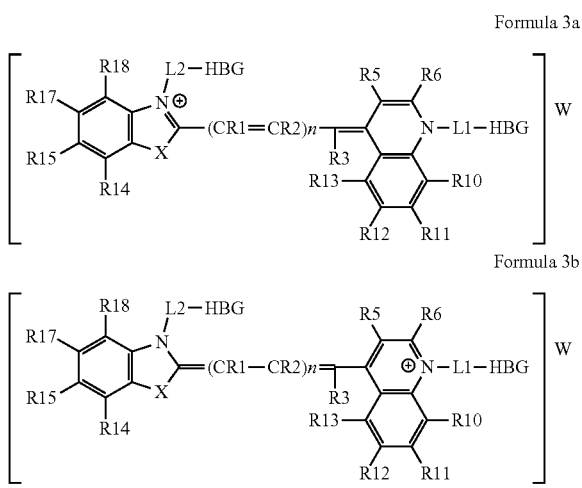

Formula 3a

Formula 3b wherein:
n is 0, 1, or 2;
R1-R3 are independently selected from hydrogen, optionally substituted alkyl, fluoro, chloro, carboxy, optionally substituted alkoxy, optionally substituted aryloxy, optionally substituted aryl, and optionally substituted heteroaryl;
R5, R6 and R10-R18 are independently selected from hydrogen, optionally substituted alkyl, halogen, carboxy, optionally substituted alkoxy, optionally substituted aryloxy, thiol, optionally substituted alkylthiol, optionally substituted arylthiol, azido, nitro, nitroso, cyano, amino, OH, a phosphonyl, a sulfonyl, a carbonyl, a boronyl, optionally substituted aryl, and optionally substituted heteroaryl;
X is O, S, or NR20 wherein R20 is selected from hydrogen, optionally substituted alkyl, optionally substituted alkenyl, optionally substituted alkynyl, optionally substituted aryl, and optionally substituted heteroaryl;
each HBG moiety is independently selected from OH, $NH_2$, amide (e.g., —$CONH_2$), $NHCOCH_3$, sulfonamide (e.g., —$SO_2NH_2$), —$NHSO_2CHF_2$, and —$NHSO_2CF_3$.

Clause 25. The compound according to clause 24, wherein:
R1-R3 are independently selected from hydrogen, optionally substituted alkyl, optionally substituted aryl, and optionally substituted heteroaryl;
R5, R6 and R10-R18 are independently selected from hydrogen, optionally substituted alkyl, chloro, fluoro, carboxy, optionally substituted alkoxy, optionally substituted aryloxy, amino, OH, a boronyl, optionally substituted aryl, and optionally substituted heteroaryl;
W is chloride, iodide, sulfate, perchlorate and trifluoroacetate;
X is O, S, or NR20 wherein R20 is hydrogen or optionally substituted alkyl;
L1 and L2 are independently is optionally substituted alkyl, a PEG, optionally substituted aryl, or optionally substituted heteroaryl; and
each HBG moiety is independently selected from OH, $NH_2$, amide, and sulfonamide.

Clause 26. The compound according to clause 24 or 25, wherein:
R1-R3 are each hydrogen;
R5 and R6 are independently selected from hydrogen, optionally substituted alkyl, optionally substituted aryl, and optionally substituted heteroaryl;
R10-R18 are independently selected from hydrogen, optionally substituted alkyl, chloro, fluoro, optionally substituted alkoxy, optionally substituted aryl, and optionally substituted heteroaryl;
R7 and R8 are independently optionally substituted alkyl;
W is chloride, iodide, sulfate, perchlorate or trifluoroacetate;
X is O, or S;
L1 and L2 are independently is optionally substituted alkyl or a PEG;
each HBG moiety is independently selected from OH, $NH_2$, an amide, and sulfonamide.

Clause 27. The compound according to clause 24, wherein:
n is 0, or 1;
R1-R3 are each H;
R6 is optionally substituted aryl or optionally substituted heteroaryl;
X is O or S;
each HBG moiety is independently selected from OH, $NH_2$, $NHCOCH_3$, —$NHSO_2CHF_2$, and —$NHSO_2CF_3$; and
L1 and L2 are independently —[$(CH_2)_q$]$_p$-Q-$(CH_2)_m$— wherein:
each q and m are independently 0 to 10 (e.g., 0 to 6 or 1 to 6);
p is 1 or 2, wherein:
when p is 1, Q is selected from O, S, NH, N, CONH, NHCO, —NR31C(O)—, —CONR31, and $N^+(R31)_2$, wherein R31 is hydrogen or (C1-C6)alkyl; and
when p is 2, Q is N.

Clause 28. The compound according to clause 27, wherein n is 0.

Clause 29. The compound according to clause 27 or 28, wherein X is O.

Clause 30. The compound according to any one of clauses 27 to 29, wherein each HBG moiety is independently selected from OH, and $NH_2$.

Clause 31. The compound according to any one of clauses 27 to 30, wherein L1 and L2 are independently (C2-C6) alkylene (e.g., (C3-C5)alkylene, such as C3 or C4-alkylene).

Clause 32. The compound according to clause 27, wherein the compound is of Formula 4a or 4b:

Formula 4a

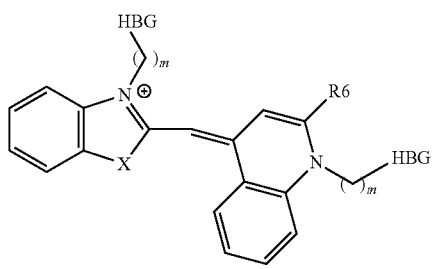

Formula 4b

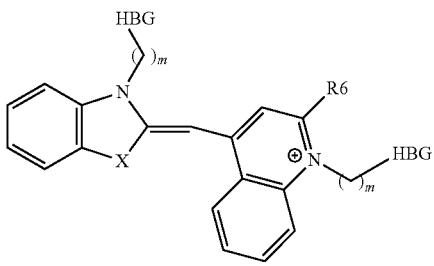

or a salt thereof,
wherein:
each m is independently 2 to 6;
X is O or S;
R6 is selected from optionally substituted phenyl, optionally substituted pyridyl (e.g., 4-pyridyl), optionally substituted thiophenyl (e.g., 2-thienyl) and optionally substituted biphenyl; and
each HBG is selected from OH, NH$_2$, NHCOCH$_3$, —NHSO$_2$CHF$_2$, and —NHSO$_2$CF$_3$.
Clause 33. The compound according to clause 32, wherein the compound is selected from:

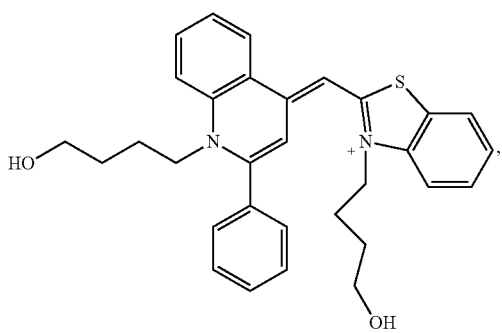

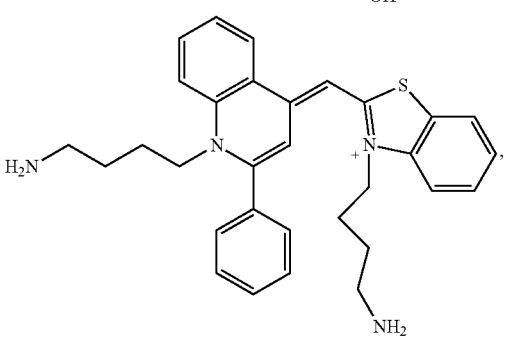

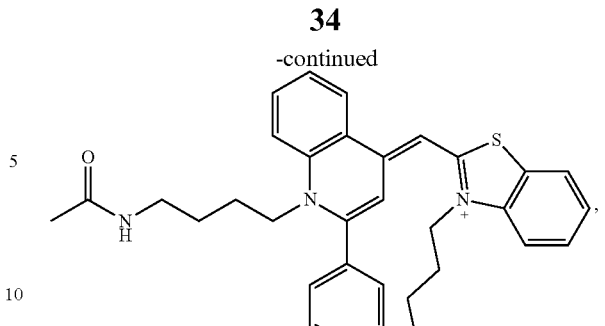

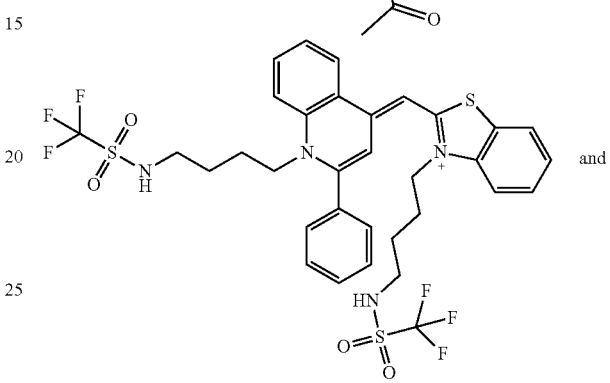

and

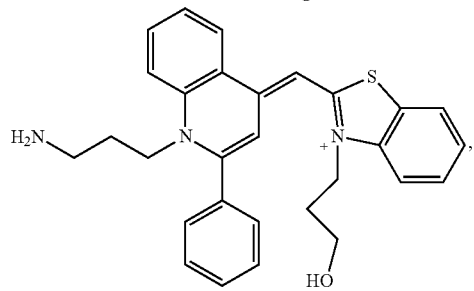

or a tautomer thereof, or a salt thereof.
Clause 34. A fluorescent complex comprising:
a nucleic acid; and
one or more cyanine compounds according to any one of clauses 1 to 33.
Clause 35. The fluorescent complex according to clause 34, wherein the nucleic acid is single stranded.
Clause 36. The fluorescent complex according to clause 34, wherein the nucleic acid is double stranded.
Clause 37. The fluorescent complex according to any one of clauses 34 to 36, wherein the nucleic acid is DNA.
Clause 38. The fluorescent complex according to any one of clauses 34 to 36, wherein the nucleic acid is RNA.
Clause 39. The fluorescent complex according to any one of clauses 34 to 37, wherein the nucleic acid is genomic DNA of a biological sample (e.g., tissue, cells, blood, serum, plants, forensic sample).
Clause 40. The fluorescent complex according to clause 39, wherein the genomic DNA has been extracted from the biological sample.
Clause 41. The fluorescent complex according to any one of clauses 34 to 37, wherein the nucleic acid is plasmid DNA.
Clause 42. The fluorescent complex according to any one of clauses 34 to 37, wherein the nucleic acid is a synthetic DNA or RNA construct.
Clause 43. The fluorescent complex according to any one of clauses 27 to 34, wherein the complex is comprised in an electrophoresis gel.

Clause 44. A bioanalytical system comprising the fluorescent complex according to any one of clauses 34 to 43.

Clause 45. The system according to clause 44, wherein the bioanalytical system comprises an electrophoresis gel.

Clause 46. A method of detecting nucleic acids in a sample, comprising:
   a) contacting a sample that contains a nucleic acid with a dye compound according to any one of clauses 1 to 33;
   b) incubating the contacted sample under conditions sufficient for the dye compound to associate with the nucleic acid in the sample to produce a fluorescent nucleic acid-dye complex; and
   c) detecting a fluorescent signal of the nucleic acid-dye complex.

Clause 47. The method according to clause 46, wherein the nucleic acids are enclosed in a biological structure (e.g., intracellular).

Clause 48. The method according to clause 47, wherein the nucleic acids are not enclosed in a biological structure (e.g., a cell).

Clause 49. The method according to clause 46, wherein the nucleic acids are isolated nucleic acids.

Clause 50. The method according to any one of clauses 46 to 48, wherein the sample is a biological sample.

Clause 51. The method according to any one of clauses 46 to 50, wherein the sample is, or is derived from, a biological sample selected from tissue, cells, blood, serum, plant, and forensic sample.

Clause 52. The method according to clauses 50 or 51, wherein the sample is a cellular sample.

Clause 53. The method according to clause 50 or 51, wherein the nucleic acid is genomic DNA of the biological sample.

Clause 54. The method according to any one of clauses 46 to 49, wherein the nucleic acid is plasmid DNA.

Clause 55. The method according to any one of clauses 46 or 49, wherein the nucleic acid is a synthetic DNA or RNA construct.

Clause 56. The method according to clause 39 or 46, further comprising, prior to step a), extracting the nucleic acid from a biological sample.

Clause 57. The method according to any one of clauses 46 to 56, further comprising, prior to step a), performing a gel electrophoresis separation on the sample comprising the nucleic acid.

Clause 58. The method according to any one of clauses 46 to 57, wherein the nucleic acid is comprised in an electrophoretic gel.

Clause 59. A kit for detecting nucleic acids in a sample, the kit comprising:
   a) one or more cyanine compounds according to any one of clauses 1 to 33;
   b) one or more components selected from a buffer (e.g., incubation buffer or wash buffer), a nucleic acid control sample, a DNA or RNA ladder, a detergent, a matrix, and an instruction sheet concerning use of the kit for detecting nucleic acids in a sample.

Clause 60. The kit according to clause 59, comprising the instruction sheet concerning use of the kit for detecting nucleic acids in a sample.

Clause 61. The cyanine compound according to any one of clauses 1 to 33, the fluorescent complex according to any one of clauses 34 to 43, the bioanalytical system according to clause 44 or 45, the method according to any one of clauses 46 to 58, or the kit according to clause 59 or 50, wherein the cyanine compound is selected from the compounds of the examples or Table 1, or a salt thereof.

EXAMPLES

The examples provided below illustrate selected aspects of this disclosure. They are not intended to limit or define the entire scope of the invention. Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

Example 1. Preparation of Compound 1

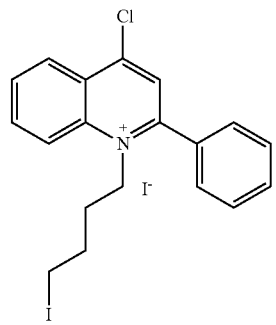

2-Phenyl-4-chloroquinoline is mixed with 1,4-diiodobutane (5 molar equivalents) and heated at 150° C. in an oil bath for 24 hours. The crude product is precipitated with ether to give pure Compound 1 as a pale-yellow solid.

Example 2. Preparation of Compound 2

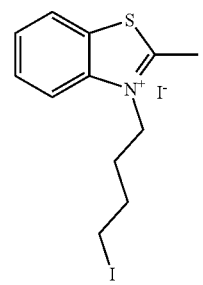

The mixture of 2-methyl-benzothiazole (1 g, 6.70 mmol) and 1,4-diiodobutane (10.38 g, 33.50 mmol) is heated at 130° C. in an oil bath for 6 hours. The solid is poured into ether, and the resulted solid is washed with dry ether and air-dried to give Compound 2.

Example 3. Preparation of Compound 3

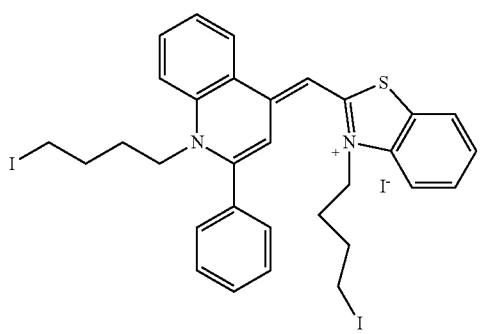

Compound 1 (0.5 g, 0.90 mmol), Compound 2 (0.44 g, 0.95 mmol) and triethyl amine (0.37 mL, 2.70 mmol) are mixed in 10 mL EtOH. The resulted solution is stirred at room temperature for 30 min. The reaction mixture is concentrated to dryness under reduced pressure to give the crude product. The crude product is further purified on a silica gel column to yield the desired pure Compound 3 using 10:1 dichloromethane/methanol (v/v) as eluant.

Example 4. Preparation of Compound 4

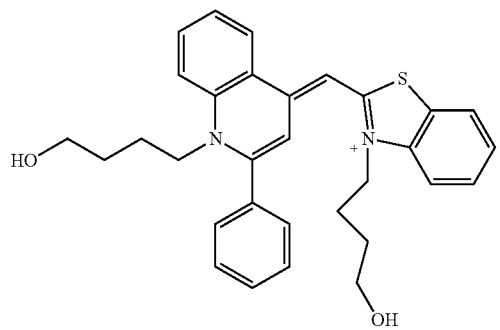

To Compound 3 (0.3 g, 0.35 mmol) in DMF (5 mL) is added potassium acetate (70 mg 0.71 mmol). The reaction mixture is stirred at 45° C. for 30 min. The resulted solution is concentrated under high vacuum, and the residue is poured into ether. The resulted precipitate is collected, washed with ether, and air-dried. The precipitate is dissolved in methanol, and to the methanol solution is added 1 N NaOH solution (5 molar equivalents). The reaction mixture is stirred at room temperature for 30 min and concentrated under reduced pressure. The residue is dissolved in 50 mL of dichloromethane and extracted with 50 mL of water. The organic layer is washed with brine, dried over $Na_2SO_4$, and concentrated under reduced pressure. The crude product is further purified on silica gel column using 10:1 dichloromethane/methanol (v/v) to give pure Compound 4 as a red solid.

Example 5. Preparation of Compound 5

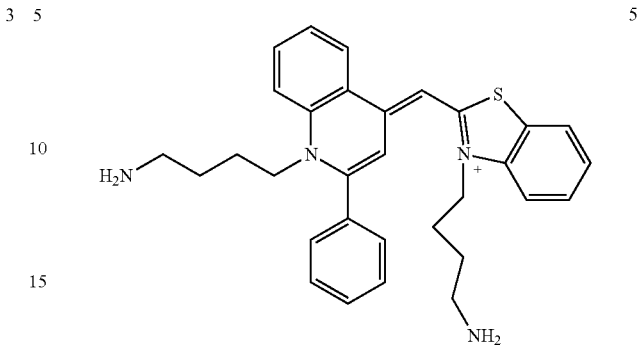

To the solution of Compound 3 (0.2 g, 0.236 mmol) in DMF (5 mL) is added phthalimide potassium salt (97 mg, 0.52 mmol). The reaction mixture is heated at 55° C. for 2 hours. The reaction mixture is concentrated under high vacuum, and the residue is washed with ether to give a red precipitate. The precipitate is dissolved in methanol (5 mL), and to the methanol solution is added hydrazine monohydrate. The resulting mixture is stirred at room temperature for 24 hours. The resulted crude product is further purified on a C18 column using a gradient mixture of water (0.1% TFA)-acetonitrile (0.1% TFA) to give the desired pure product.

Example 6. Preparation of Compound 6

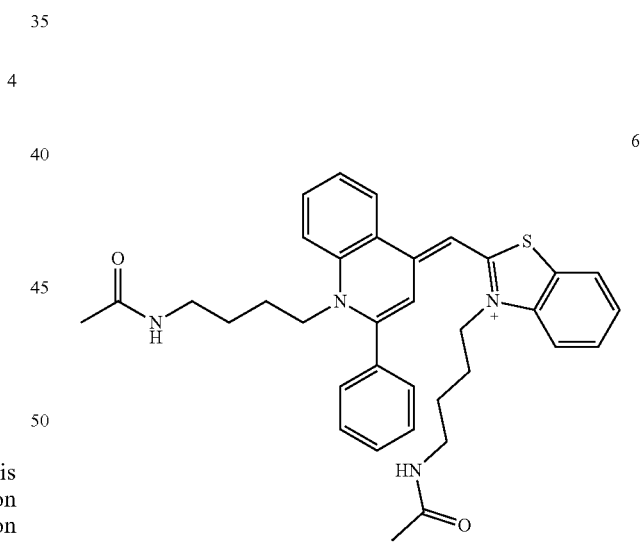

To the solution of Compound 5 (0.1 g, 0.16 mmol) in DMA (1 mL) are added triethylamine (0.23 mL, 1.6 mmol) and acetic anhydride (0.08 mL, 0.8 mmol). The reaction mixture is stirred at room temperature for 2 hours and concentrated under high vacuum. The residue is poured into 50 mL of water and extracted with 50 mL of dichloromethane. The organic layer is washed with brine, dried over $Na_2SO_4$, and concentrated under reduced pressure. The crude product is further purified on a silica gel column using 10:1 dichloromethane/methanol (v/v) to give the desired pure product as a red solid.

Example 7. Preparation of Compound 7

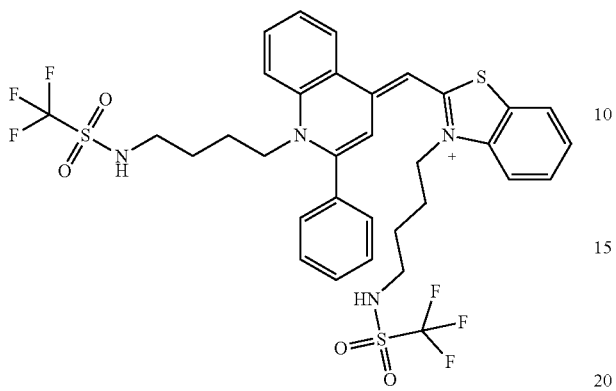

To the solution of Compound 5 (0.1 g, 0.16 mmol) in DMA (1 mL) are added at 0° C. triethylamine (0.23 mL, 1.6 mmol) and methyl trifluoromethanesulfonate (0.087 mL, 0.8 mmol), and the reaction mixture is stirred at 0° C. for 1 hour. The resulted mixture is concentrated under high vacuum, and the residue is dispersed into 50 mL of water and extracted with 50 mL of dichloromethane. The organic layer is washed with brine, dried over $Na_2SO_4$, and concentrated under reduced pressure. The crude product is further purified on a silica gel column using 10:1 dichloromethane/methanol (v/v) to give the desired pure product as a red solid.

Example 8. Preparation of Compound 8

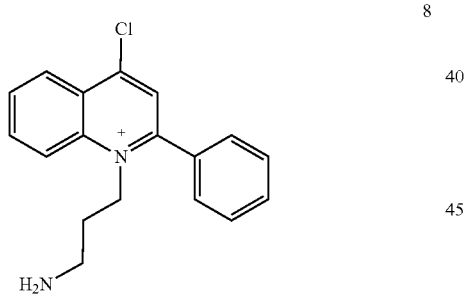

Compound 8 is prepared from the reaction of Compound 1 with 3-bromopropylamine analogously according to the procedure of Gang Li (CN111233856).

Example 9. Preparation of Compound 9

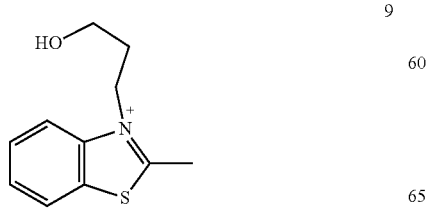

Compound 9 is prepared from the reaction of Compound 8 with 3-(3-hydroxypropyl)-2-methyl-benzothiazolium tosylate (David Margulies, et al, WO2014102803) analogously according to the procedure of Compound 3.

Example 10. Preparation of Compound 10

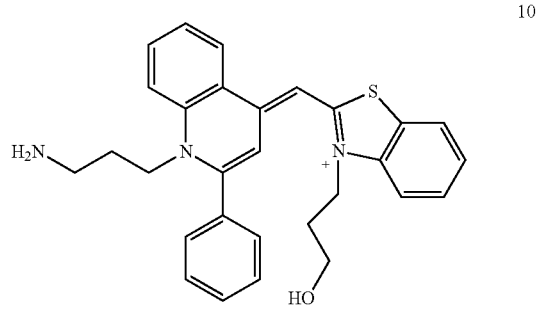

Compound 10 is prepared from the reaction of Compound 8 with 3-(3-hydroxypropyl)-2-methyl-benzoxazolium chloride (Christopher Bieniarz et al., WO9501341) analogously according to the procedure of Compound 3.

Example 11. Preparation of Compound 11

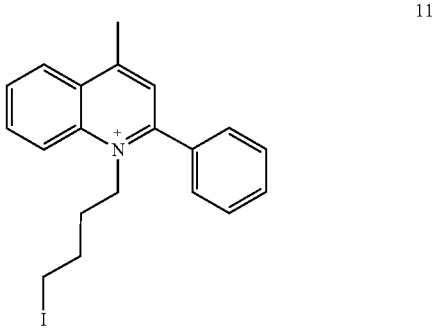

The mixture of 4-methyl-2-phenylquinoline (3 g, 14.6 mmol) and 1,4-diiodobutane (13.48 g, 43.8 mmol) is heated at 120° C. in an oil bath for 24 hours. The solid is poured into dry ether. The resulted suspension is filtered off, and the precipitate is collected and washed with dry ether. The light-yellow solid is dried in vacuum to give the desired product.

Example 12. Preparation of Compound 12

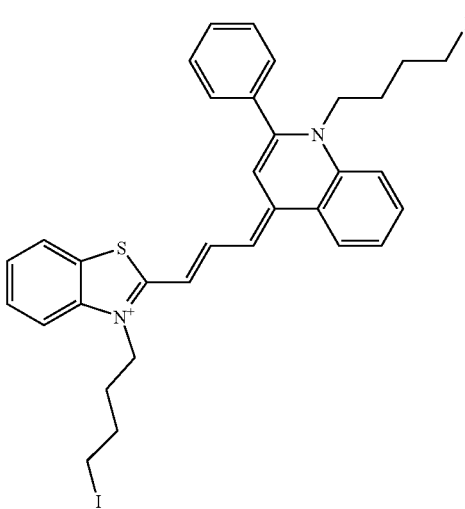

12

Compound 11 (0.53 g, 1 mmol) and N,N'-diphenylformamidine (0.59 g, 3 mmol) are mixed in acetic anhydride (3 mL). The reaction mixture is stirred at 120° C. for 2 hours. To the reaction mixture are sequentially added 3-(4-idobutyl)-2-methyl-benzothiazolium iodide (0.46 g, 1 mmol), dichloromethane (5 mL), MeOH (5 mL) and trimethylamine (1.5 mL). The solution is stirred in the dark for 2 hours. The mixture is concentrated to dryness under reduced pressure. The crude product is purified on a silica gel column using 10:1 dichloromethane/methanol (v/v) to yield the desired product as a blue solid.

Example 13. Preparation of Compound 13

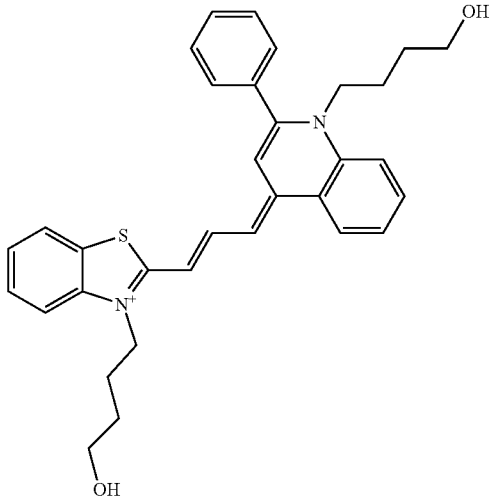

13

To the solution of Compound 12 (0.35 mmol) in DMF (5 mL) is added potassium acetate (0.71 mmol). The reaction mixture is stirred at 45° C. for 30 min. The resulted solution is concentrated under high vacuum, and the residue is poured into ether. The resulted precipitate is collected, washed with ether, and air-dried. The precipitate is dissolved in methanol, and to the methanol solution is added 1 N NaOH solution (5 molar equivalents). The reaction mixture is stirred at room temperature for 30 min and concentrated under reduced pressure. The residue is dissolved in 50 mL of dichloromethane and extracted with 50 mL of water. The organic layer is washed with brine, dried over $Na_2SO_4$, and concentrated under reduced pressure. The crude product is further purified on silica gel column using 10:1 dichloromethane/methanol (v/v) to give the desired pure product as a blue solid.

Example 14. Preparation of Compound 14

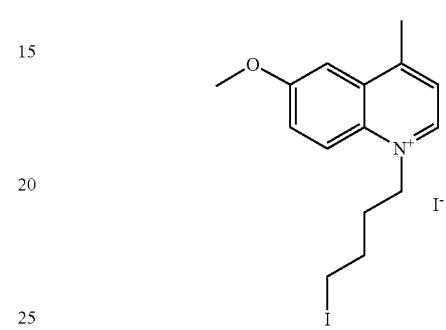

14

The mixture of 4-methyl-6-methoxyquinoline (15 mmol) and 1,4-diiodobutane (50 mmol) is heated at 120° C. in an oil bath for 24 hours. The solid is poured into dry ether. The resulted suspension is filtered off, and the precipitate is collected and washed with dry ether. The light-yellow solid is dried in vacuum to give the desired product.

Example 15. Preparation of Compound 15

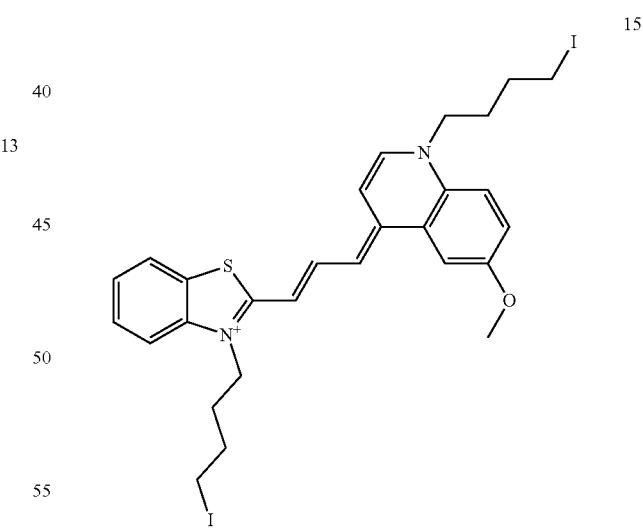

15

Compound 14 (1 mmol) and N,N'-diphenylformamidine (3 mmol) are mixed in acetic anhydride (3 mL). The reaction mixture is stirred at 120° C. for 2 hours. To the reaction mixture are sequentially added 3-(4-idobutyl)-2-methyl-benzothiazolium iodide (1 mmol), dichloromethane (5 mL), MeOH (5 mL) and trimethylamine (1.5 mL). The solution is stirred in the dark for 2 hours. The mixture is concentrated to dryness under reduced pressure. The crude product is purified on a silica gel column using 10:1 dichloromethane/methanol (v/v) to yield the desired product as a blue solid.

Example 16. Preparation of Compound 16

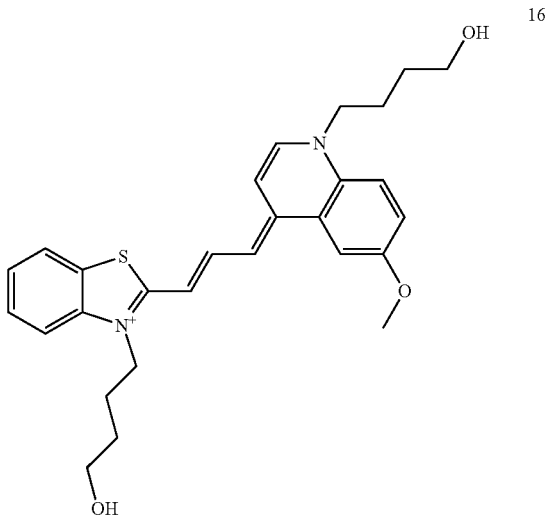 [SMILES: COc1ccc2c(c1)/C(=C/C=C/c1sc3ccccc3[n+]1CCCCO)C=CN2CCCCO]

To the solution of Compound 15 (0.35 mmol) in DMF (5 mL) is added potassium acetate (0.71 mmol). The reaction mixture is stirred at 45° C. for 30 min. The resulted solution is concentrated under high vacuum, and the residue is poured into ether. The resulted precipitate is collected, washed with ether, and air-dried. The precipitate is dissolved in methanol, and to the methanol solution is added 1 N NaOH solution (5 molar equivalents). The reaction mixture is stirred at room temperature for 30 min and concentrated under reduced pressure. The residue is dissolved in 50 mL of dichloromethane and extracted with 50 mL of water. The organic layer is washed with brine, dried over $Na_2SO_4$, and concentrated under reduced pressure. The crude product is further purified on silica gel column using 10:1 dichloromethane/methanol (v/v) to give the desired pure product as a blue solid.

It is understood that a variety of cyanine dye compounds of this disclosure can be analogously prepared by adapting the methods illustrated in the above examples. Exemplary cyanine dyes of this disclosure are listed in the following table.

TABLE 1

Exemplary cyanine dyes of this disclosure.

| Compound Code | Structure |
|---|---|
| 20 | 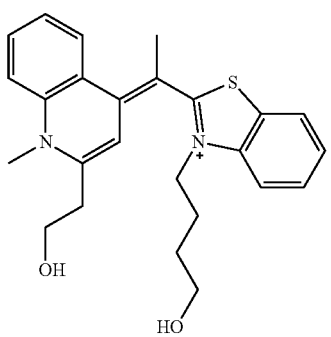 |
| 23 | 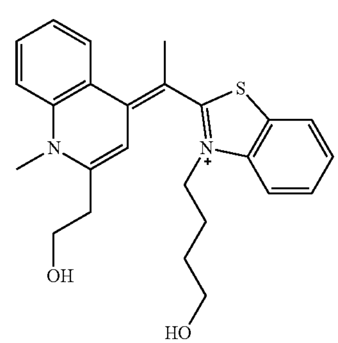 [SMILES: C/C(=C1/C=C(CCO)N(C)c2ccccc21)c1sc2ccccc2[n+]1CCCCO] |

TABLE 1-continued
Exemplary cyanine dyes of this disclosure.
| Compound Code | Structure |
|---|---|
| 24 | 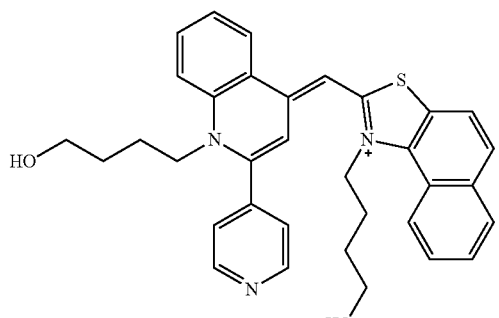 |
| 25 | 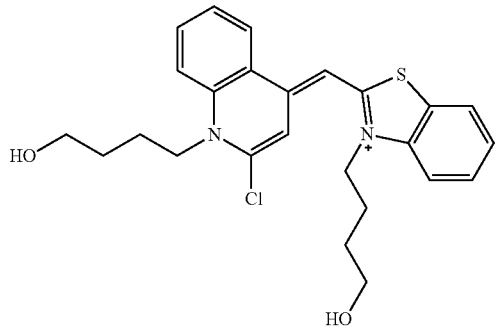 [SMILES: OCCCCN1C(Cl)=C/C(=C\c2sc3ccccc3[n+]2CCCCO)c2ccccc21] |
| 26 | 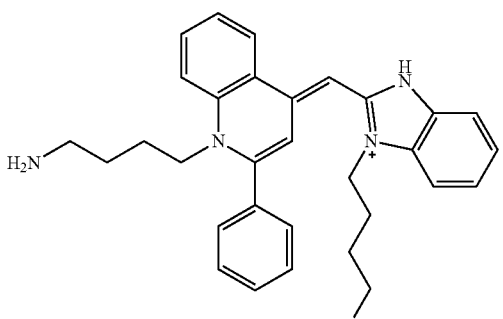 |
| 27 | 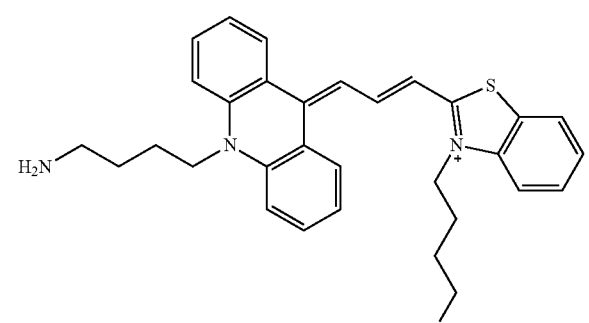 |

TABLE 1-continued
Exemplary cyanine dyes of this disclosure.
| Compound Code | Structure |
|---|---|
| 28 | 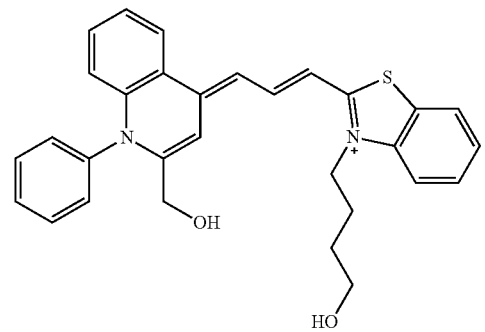 [SMILES: OCCCC[n+]1c(/C=C/C=C2\C=C(CO)N(c3ccccc3)c3ccccc32)sc2ccccc21] |
| 29 | 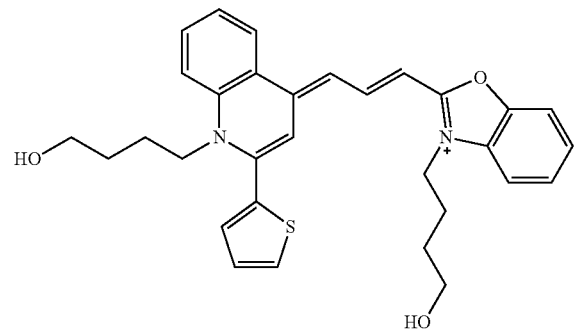 [SMILES: OCCCCN1C(c2cccs2)=C/C(=C\C=C\c2oc3ccccc3[n+]2CCCCO)c2ccccc21] |
| 30 | 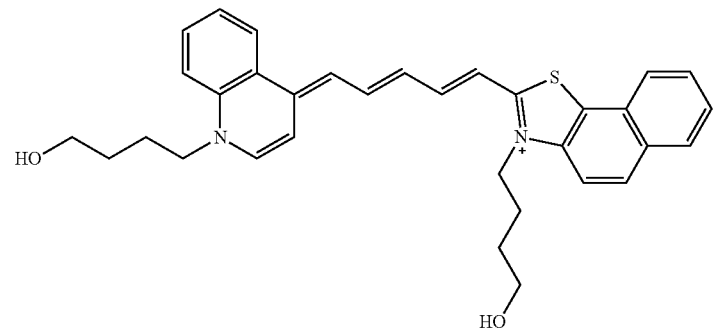 [SMILES: OCCCCN1C=C\C(=C/C=C/C=C/c2sc3c4ccccc4ccc3[n+]2CCCCO)c2ccccc21] |
| 31 | 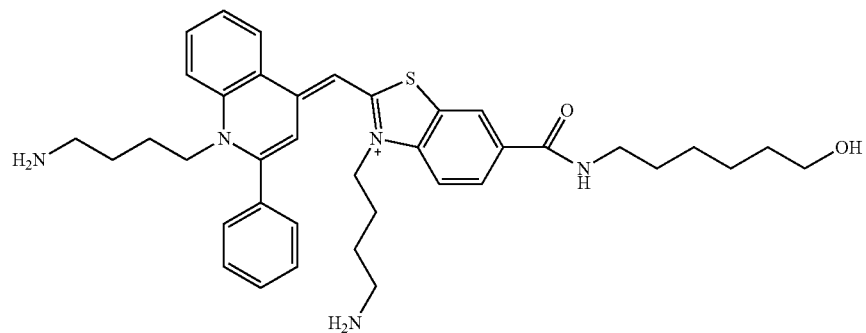 [SMILES: NCCCCN1C(c2ccccc2)=C/C(=C\c2sc3cc(C(=O)NCCCCCCO)ccc3[n+]2CCCCN)c2ccccc21] |

TABLE 1-continued
Exemplary cyanine dyes of this disclosure.
| Compound Code | Structure |
|---|---|
| 32 | 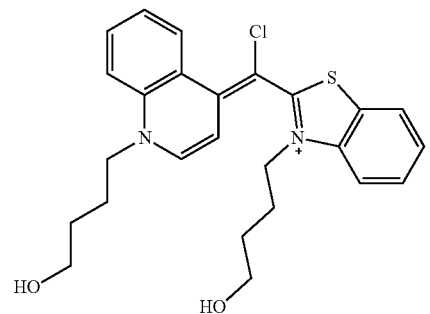 [SMILES: OCCCCN1C=C/C(=C(/Cl)c2sc3ccccc3[n+]2CCCCO)c2ccccc21] |
| 33 | 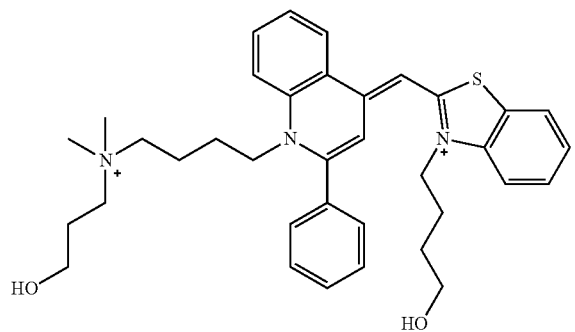 [SMILES: C[N+](C)(CCCO)CCCCN1C(c2ccccc2)=C/C(=C\c2sc3ccccc3[n+]2CCCCO)c2ccccc21] |
| 34 | 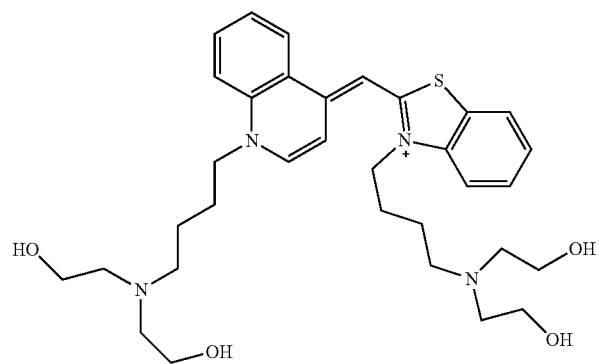 [SMILES: OCCN(CCO)CCCCN1C=C/C(=C\c2sc3ccccc3[n+]2CCCCN(CCO)CCO)c2ccccc21] |
| 35 | 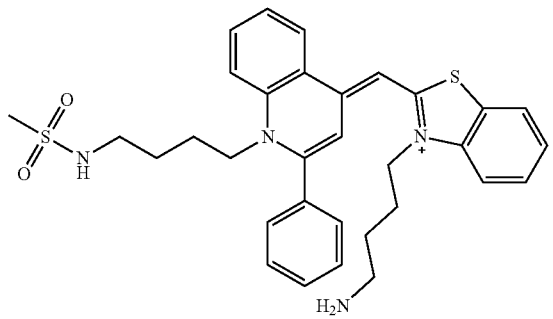 [SMILES: CS(=O)(=O)NCCCCN1C(c2ccccc2)=C/C(=C\c2sc3ccccc3[n+]2CCCCN)c2ccccc21] |

US 12,169,166 B2
TABLE 1-continued
Exemplary cyanine dyes of this disclosure.
| Compound Code | Structure |
|---|---|
| 36 | 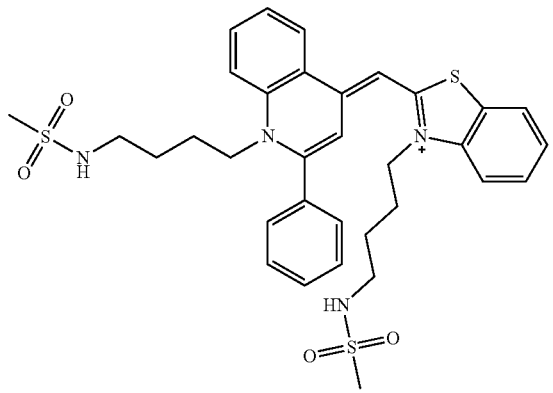 [SMILES: CS(=O)(=O)NCCCCN1C(c2ccccc2)=C/C(=C\c2sc3ccccc3[n+]2CCCCNS(C)(=O)=O)c2ccccc21] |
| 37 | 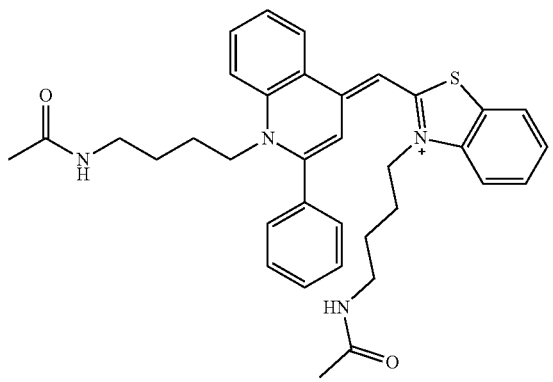 [SMILES: CC(=O)NCCCCN1C(c2ccccc2)=C/C(=C\c2sc3ccccc3[n+]2CCCCNC(C)=O)c2ccccc21] |
| 38 | 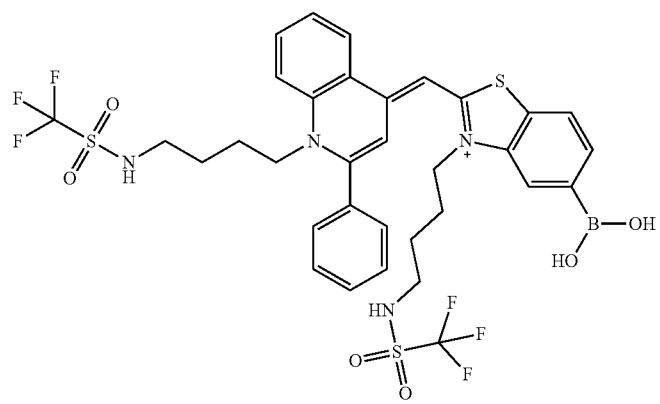 [SMILES: O=S(=O)(NCCCCN1C(c2ccccc2)=C/C(=C\c2sc3ccc(B(O)O)cc3[n+]2CCCCNS(=O)(=O)C(F)(F)F)c2ccccc21)C(F)(F)F] |

TABLE 1-continued

Exemplary cyanine dyes of this disclosure.

| Compound Code | Structure |
|---|---|
| 39 | 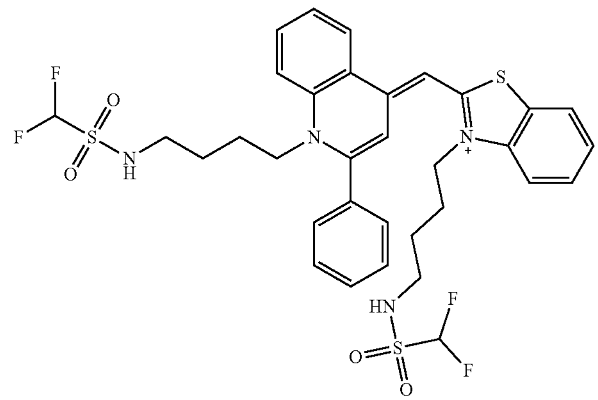 [SMILES: O=S(=O)(NCCCCN1C(c2ccccc2)=C/C(=C\c2sc3ccccc3[n+]2CCCCNS(=O)(=O)C(F)F)c2ccccc21)C(F)F] |
| 40 | 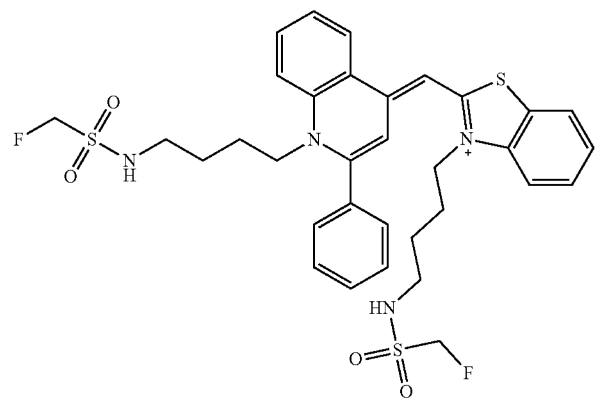 [SMILES: O=S(=O)(CF)NCCCCN1C(c2ccccc2)=C/C(=C\c2sc3ccccc3[n+]2CCCCNS(=O)(=O)CF)c2ccccc21] |
| 41 | 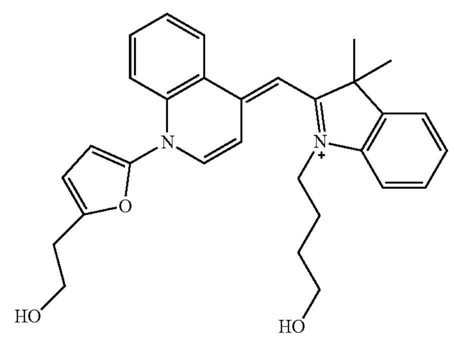 [SMILES: CC1(C)C(/C=C2\C=CN(c3ccc(CCO)o3)c3ccccc32)=[N+](CCCCO)c2ccccc21] |
| 51 | 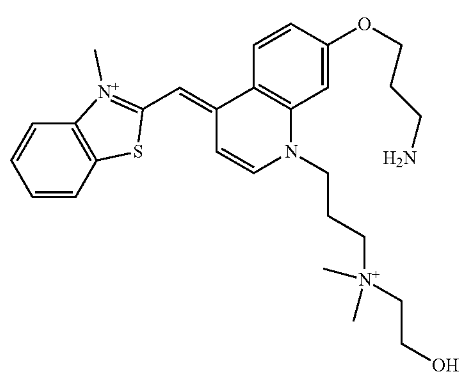 [SMILES: C[n+]1c(/C=C2\C=CN(CCC[N+](C)(C)CCO)c3cc(OCCCN)ccc32)sc2ccccc21] |

TABLE 1-continued
Exemplary cyanine dyes of this disclosure.
| Compound Code | Structure |
|---|---|
| 52 | 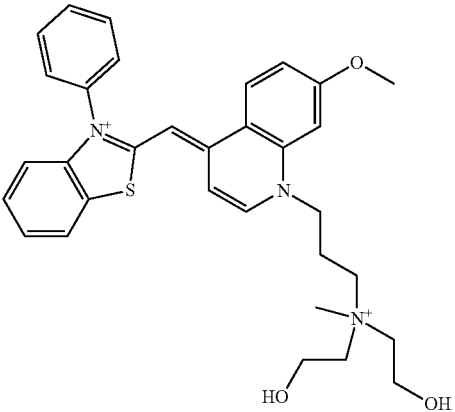 [SMILES: COc1ccc2c(c1)N(CCC[N+](C)(CCO)CCO)C=C/C2=C\c1sc2ccccc2[n+]1-c1ccccc1] |
| 53 | 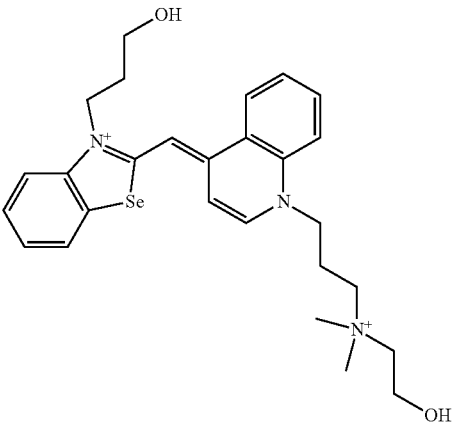 [SMILES: C[N+](C)(CCO)CCCN1C=C/C(=C\c2[se]c3ccccc3[n+]2CCCO)c2ccccc21] |
| 54 | 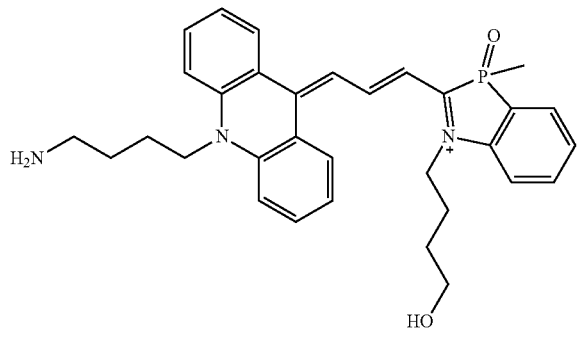 [SMILES: CP1(=O)C(/C=C/C=C2c3ccccc3N(CCCCN)c3ccccc32)=[N+](CCCCO)c2ccccc21] |
| 55 | 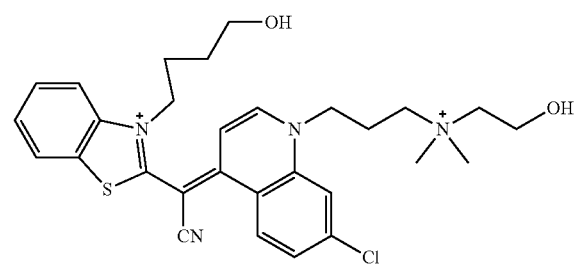 [SMILES: C[N+](C)(CCO)CCCN1C=C/C(=C(/C#N)c2sc3ccccc3[n+]2CCCCO)c2ccc(Cl)cc21] |

TABLE 1-continued
Exemplary cyanine dyes of this disclosure.
| Compound Code | Structure |
|---|---|
| 56 | 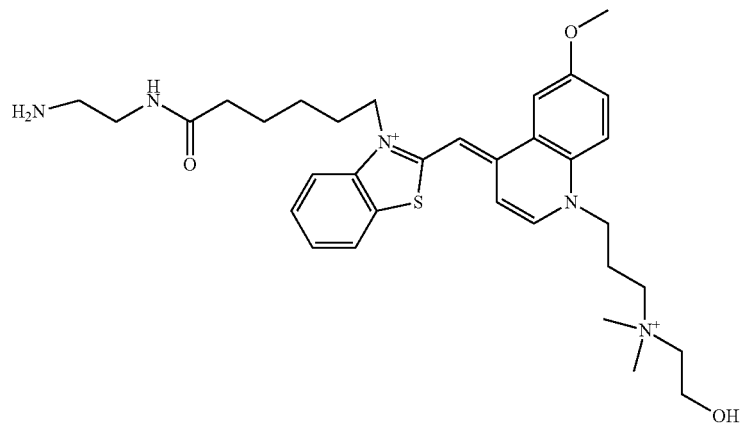 [SMILES: COc1ccc2c(c1)/C(=C/c1sc3ccccc3[n+]1CCCCCC(=O)NCCN)C=CN2CCC[N+](C)(C)CCO] |
| 57 | 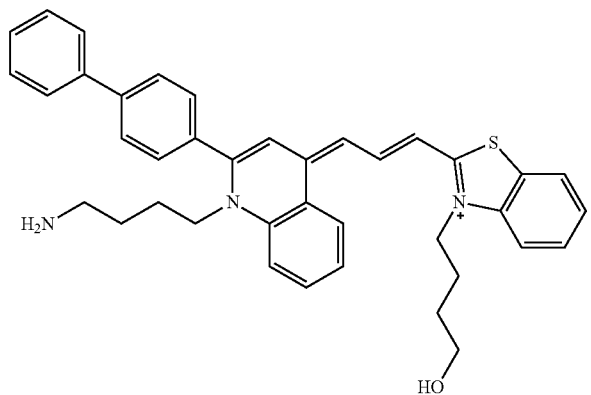 [SMILES: NCCCCN1C(c2ccc(-c3ccccc3)cc2)=C/C(=C/C=C/c2sc3ccccc3[n+]2CCCCO)c2ccccc21] |
| 58 | 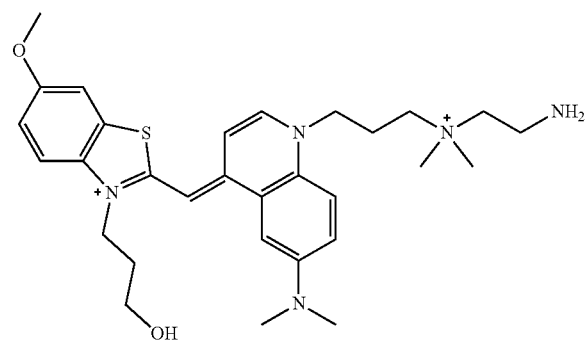 [SMILES: COc1ccc2c(c1)sc(/C=C1\C=CN(CCC[N+](C)(C)CCN)c3ccc(N(C)C)cc31)[n+]2CCCO] |

TABLE 1-continued
Exemplary cyanine dyes of this disclosure.
| Compound Code | Structure |
|---|---|
| 59 | 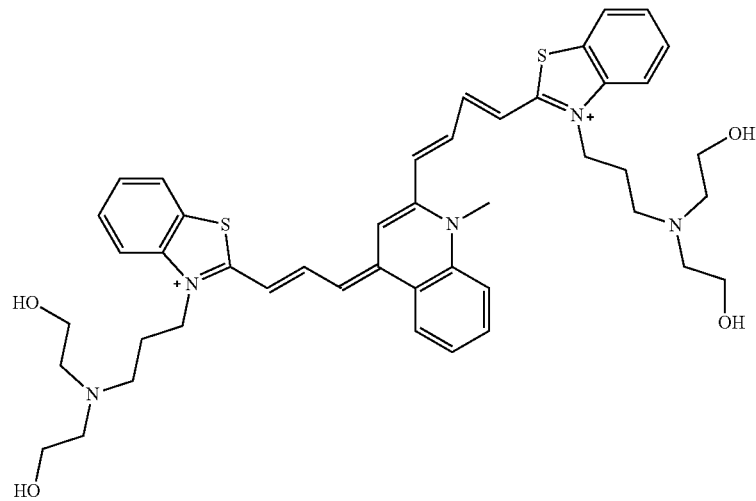 [SMILES: CN1C(/C=C/C=C/c2sc3ccccc3[n+]2CCCN(CCO)CCO)=CC(=C\C=C\c2sc3ccccc3[n+]2CCCN(CCO)CCO)/c2ccccc21] |
| 60 | 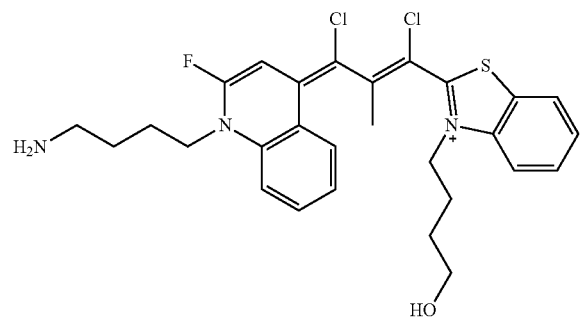 [SMILES: CC(=C(/Cl)c1sc2ccccc2[n+]1CCCCO)/C(Cl)=C1/C=C(F)N(CCCCN)c2ccccc21] |
| 61 | 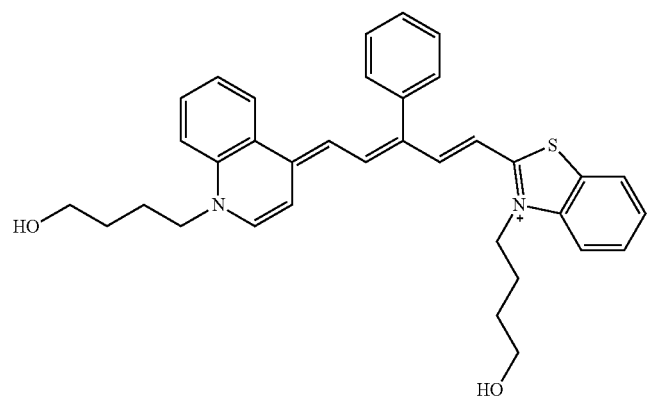 [SMILES: OCCCCN1C=C\C(=C/C=C(/C=C/c2sc3ccccc3[n+]2CCCCO)c2ccccc2)c2ccccc21] |
| 62 | 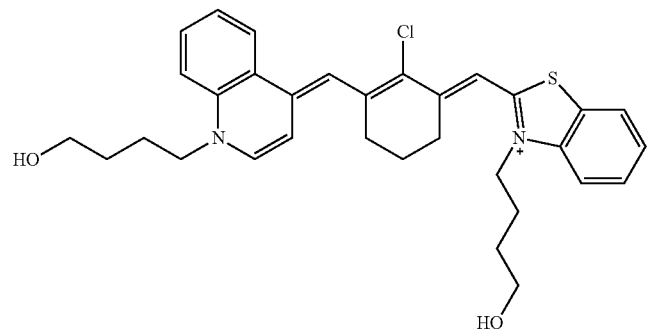 [SMILES: OCCCCN1C=C/C(=C\C2=C(Cl)C(=C/c3sc4ccccc4[n+]3CCCCO)/CCC2)c2ccccc21] |

TABLE 1-continued
Exemplary cyanine dyes of this disclosure.
| Compound Code | Structure |
|---|---|
| 63 | 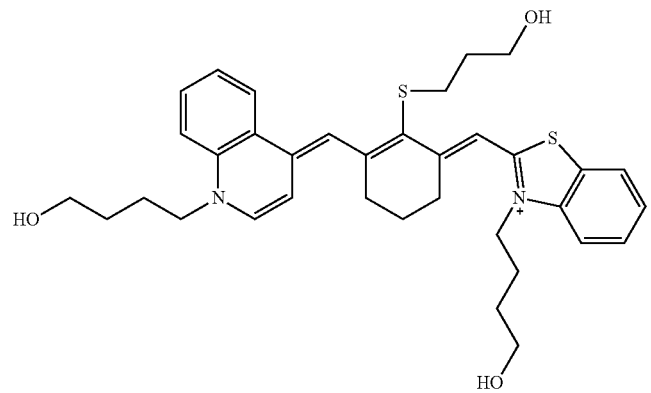 [SMILES: OCCCCN1C=C/C(=C\C2=C(SCCCO)C(=C/c3sc4ccccc4[n+]3CCCCO)/CCC2)c2ccccc21] |
| 64 | 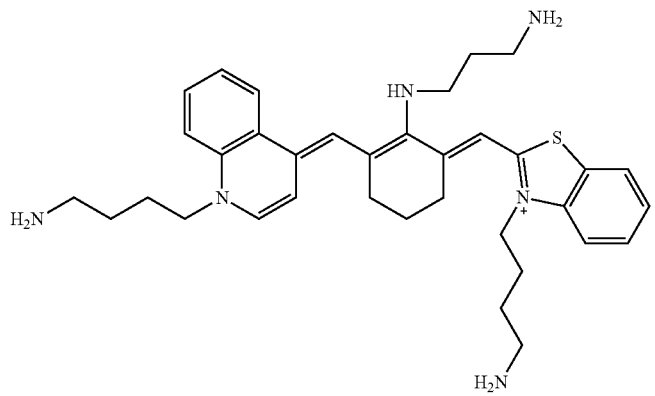 [SMILES: NCCCCN1C=C/C(=C\C2=C(NCCCN)C(=C/c3sc4ccccc4[n+]3CCCCN)/CCC2)c2ccccc21] |
| 65 | 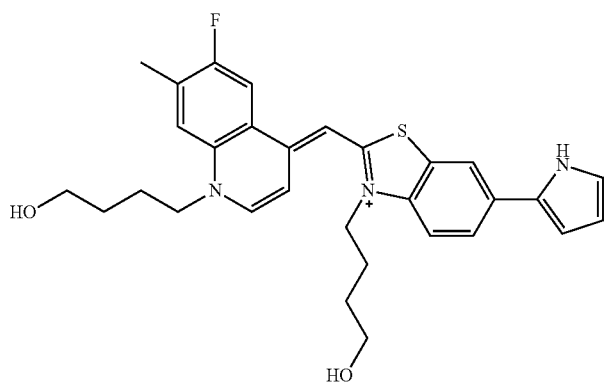 [SMILES: Cc1cc2c(cc1F)/C(=C/c1sc3cc(-c4ccc[nH]4)ccc3[n+]1CCCCO)C=CN2CCCCO] |
| 66 | 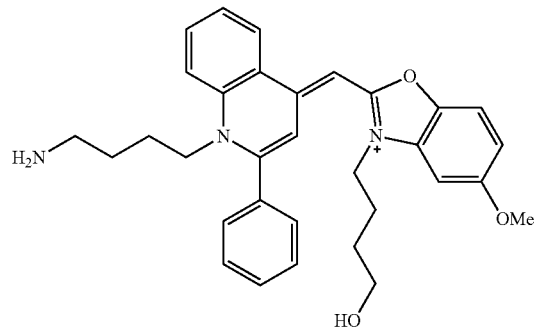 [SMILES: COc1ccc2oc(/C=C3\C=C(c4ccccc4)N(CCCCN)c4ccccc43)[n+](CCCCO)c2c1] |

TABLE 1-continued

Exemplary cyanine dyes of this disclosure.

| Compound Code | Structure |
|---|---|
| 67 | 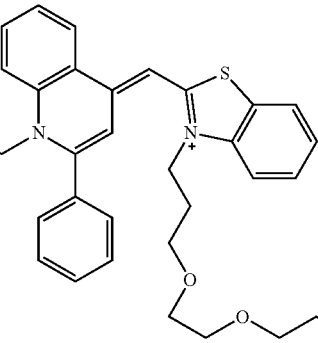 |
| 68 | 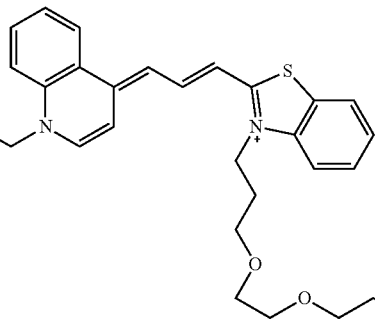 |

It is understood that salt forms (e.g., including a counterion as disclosed herein) of any of the compounds of the table 1 are also included.

TABLE 2

Selected dyes for comparative experiments

| Compound Code | Structure |
|---|---|
| TO (Thiazole Orange) | 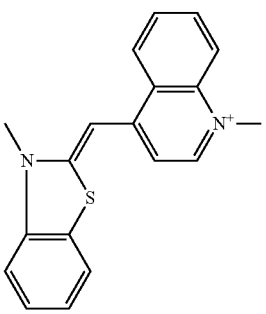 [SMILES: CN1/C(=C/c2cc[n+](C)c3ccccc23)Sc2ccccc21] |
| SB (SYBR Green) | 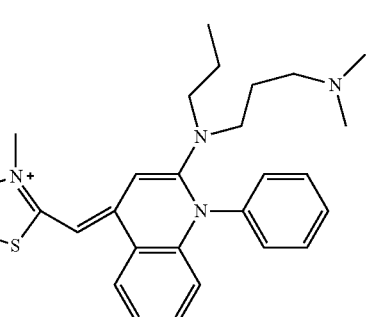 |

Example 17. Absorption and Fluorescence Spectra of Cyanine Compounds

Figure 1B:
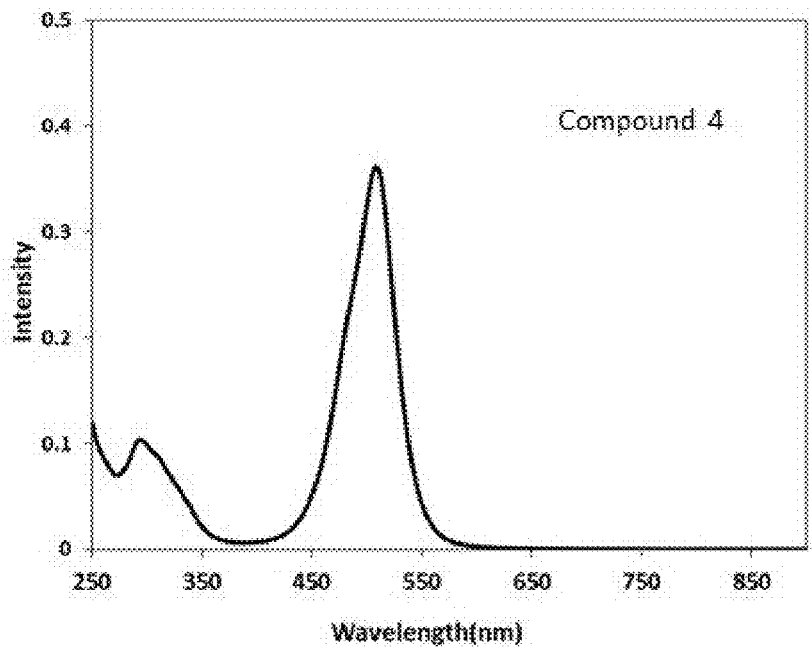
Figure 2A:
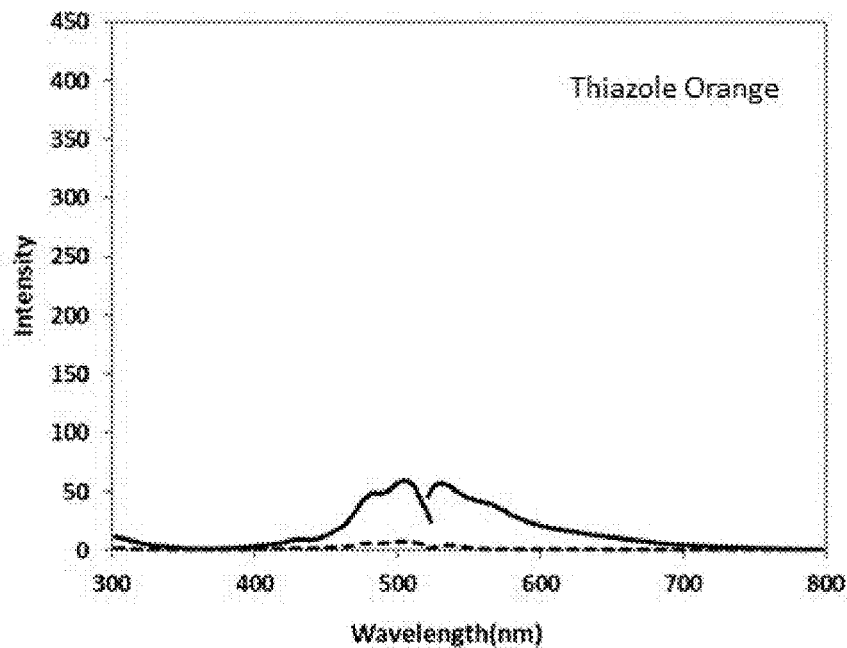
FIGS. 2A-2B shows the fluorescence emission spectra of Thiazole Orange (TO) (5 ug/ml) and Compound 4 (5 ug/ml) in the presence (solid line) or absence (dot line) of DNA (3 ug/ml) in Tris Buffer (pH=8.0). Compounds 5, 6, 7 and 10 have stronger fluorescence enhancements than TO as Compound 4 does.
Figure 2B:
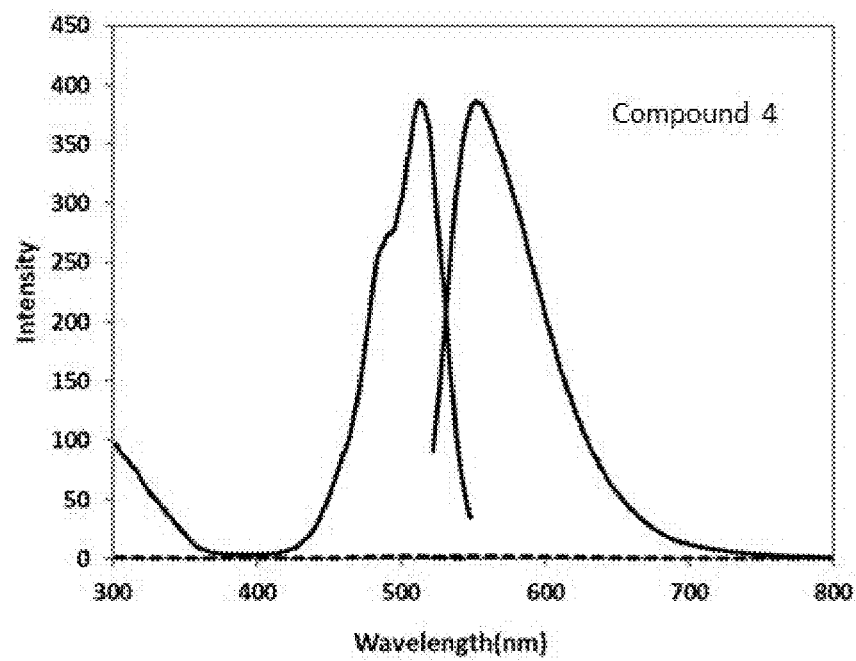

Absorption and fluorescence spectra of cyanine compounds are measured in the presence or absence of DNA in Tris buffer (pH=8.0). Specifically, with Compound 4 as an example, its absorption and fluorescence spectra are measured separately in the presence of 50 ug/ml of Calf thymus DNA in Tris buffer (pH=8.0). The excitation and emission spectra are normalized to 100 in the plot as shown in FIGS. 1 and 2.

Example 18. DNA Responses in Solution

Figure 3:
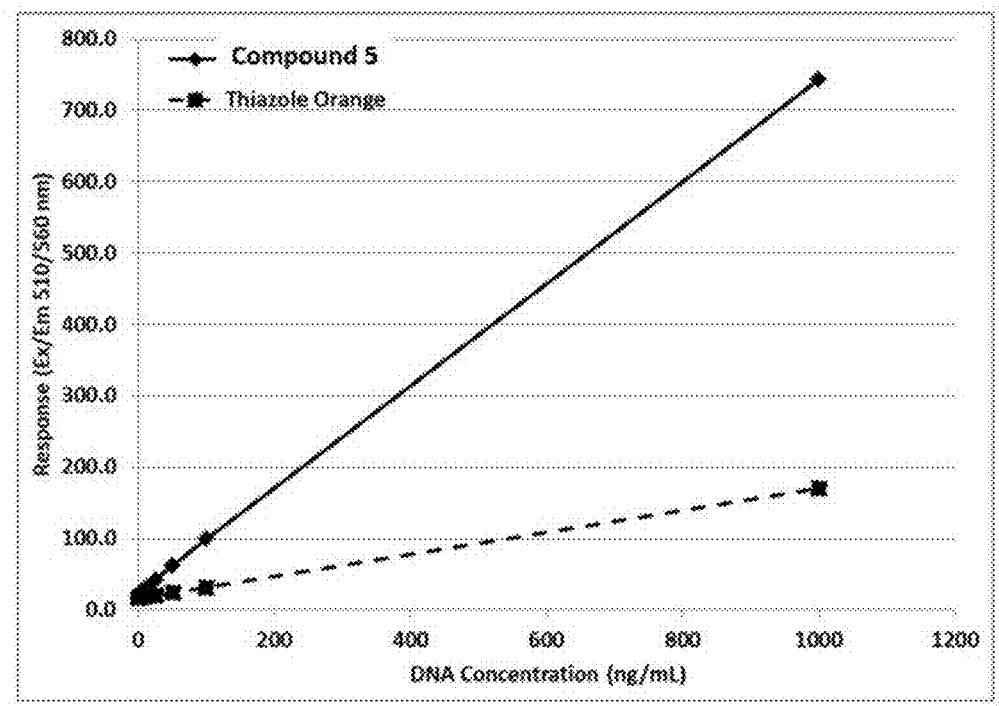
FIG. 3 shows fluorescence response of Compound 5 (0.25 ug/ml) to increasing concentrations on DNA in Tris Buffer (pH=8.0). The fluorescence intensities of Compound 5 are measured in the presence of serial dilutions of a DNA sample (0, 3.12, 6.25, 12.5, 25, 50, 100, 1000 ng/ml). Compound 5 demonstrates significantly higher fluorescence signals than Thiazole orange (TO). Compounds 4, 6, 7 and 10 also have stronger fluorescence signals than TO similar to Compound 4.

The fluorescence of a cyanine compound in 100 μL of Tris Buffer (pH=8.0) are measured in the presence of 0, 0.21, 0.62, 1.85, 5.6, 16.7, and 50 μg/ml final concentrations of Calf thymus DNA with a microtiter plate reader. The fluorescence is plotted against DNA concentration. As shown in FIG. 3, the fluorescence intensities of Compound 4 are linearly responded to the DNA concentrations with better sensitivity than TO as shown in FIG. 3. Compounds 5, 6, 7 and 10 also have stronger fluorescence signals than TO as Compound 4 does.

Example 19. Pre-Cast DNA Gel Staining

An agarose gel solution (0.9% agarose) is prepared following a standard protocol (J. Roskams et al., *Lab Ref A Handbook of Recipes, Reagents, and Other Reference Tools for Use at the Bench*, Cold Spring Harbor Laboratory Press, Cold Spring Harbor, N.Y., 2002). A stock solution of a cyanine dye in DMSO is prepared. An aliquot of the stock solution of dye is added to the gel solution, while it is hot, resulting in an effective working concentration of the dye (1 μg/ml). The resulting solution is thoroughly mixed by swirling. The resulting gel solution is poured onto a gel slab to cast the gel. Serial two-fold dilutions of pGL3 Control vector (Promega) are made and the resulting DNA samples are loaded onto the gel in eight lanes from left to right with a loading of 86, 43, 21.5, 10.7, 5.3, 2.6, 1.3, 0.5 ng/lane, respectively. The DNA samples are electrophoretically separated in 1×TAE buffer using a standard protocol. The resulting gel is then viewed using a UV transilluminator with 300 nm excitation. Photographs of the illuminated gels are taken with an EB filter. As shown in FIG. 4, Compound 5 can clearly detect 5.3 ng DNA while TO can only detect 43 ng. Compounds 4, 6, 7 and 10 also demonstrate much higher sensitivity for detecting DNA on gel than TO under the same conditions.

Example 20. Post-DNA Gel Staining

Agarose gels (0.9% agarose) are prepared following a standard protocol (J. Roskams et al., *Lab Ref A Handbook of Recipes, Reagents, and Other Reverence Tools for Use at the Bench*, Cold Spring Harbor Laboratory Press, Cold Spring Harbor, N.Y., 2002). Serial two-fold dilutions of pGL3 Control vector (Promega) are made and the resulting DNA samples are loaded onto an agarose gel in eight lanes from left to right with a loading of 86, 43, 21.5, 10.7, 5.3, 2.6, 1.3, 0.5 ng/lane, respectively. The DNA samples are electrophoretically separated in 1×TAE buffer using a standard protocol. A stock solution of a cyanine dye in DMSO at about 12 mM concentration is prepared. The stock solution of dye is diluted using an appropriate aqueous solvent to provide a staining solution with an appropriate effective working concentration of the dye (1 ug/ml). The agarose gel is submerged in the staining solution for approximately 30 minutes to stain the gel. The resulting gel is then viewed using a UV transilluminator with 300 nm excitation. Photographs of the fluorescent images of the illuminated gels are taken with an EB filter. As shown in FIG. 5, Compound 5 can clearly detect 5.3 ng DNA while TO can only detect 43 ng. Compounds 4, 6, 7 and 10 also demonstrate much higher sensitivity for detecting DNA on gel than TO under the same conditions.

Example 21. Cellular Nucleic Acid Staining

Figure 6:
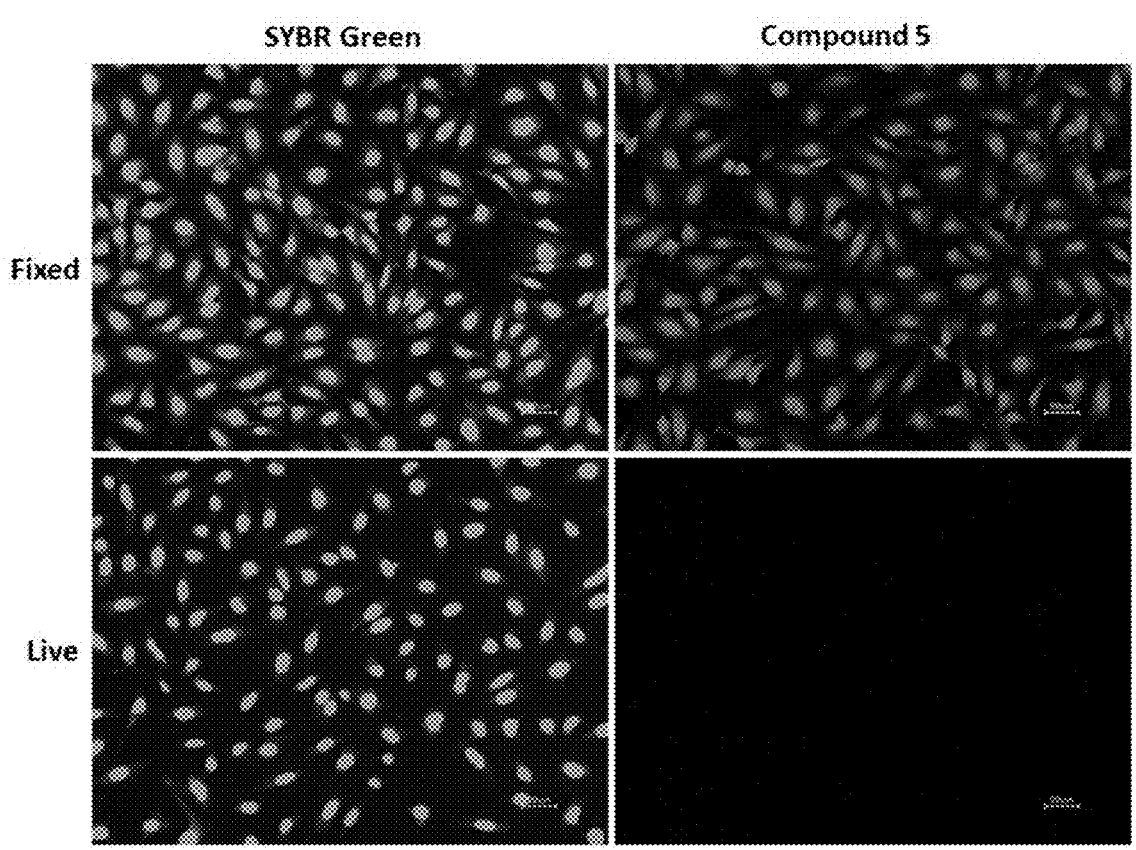
FIG. 6 shows a representation of cell images after incubation with Thiazole Orange or Compound 5 in either fixed cells (top) or live cells (bottom), respectively. A cyanine dye (1 μg/ml) in PBS buffer is incubated with live or fixed HeLa cells in 96-well plate for 30 min respectively. The fluorescence image of cells is taken with a fluorescence microscope. As shown in the figure, Compound 5 is live cell impermeant while Thiazole Orange can readily penetrate the cells. Compounds 4, 6, 7 and 10 also demonstrate cell impermeability under the same conditions.

A cyanine dye (1 μg/ml) in PBS buffer (prepared from 1 mM DMSO stock solution) is incubated with live and fixed HeLa cells in 96-well plate for 30 min respectively. The fluorescence image of cells is taken with a fluorescence microscope as shown in FIG. 6. As shown in the figure, Compound 5 is live cell impermeant while Thiazole Orange can readily penetrate cells. Compounds 4, 6, 7 and 10 also demonstrate cell impermeability under the same conditions.

Example 22. Cellular Cytotoxicities of Cyanine Dyes

Figure 7:
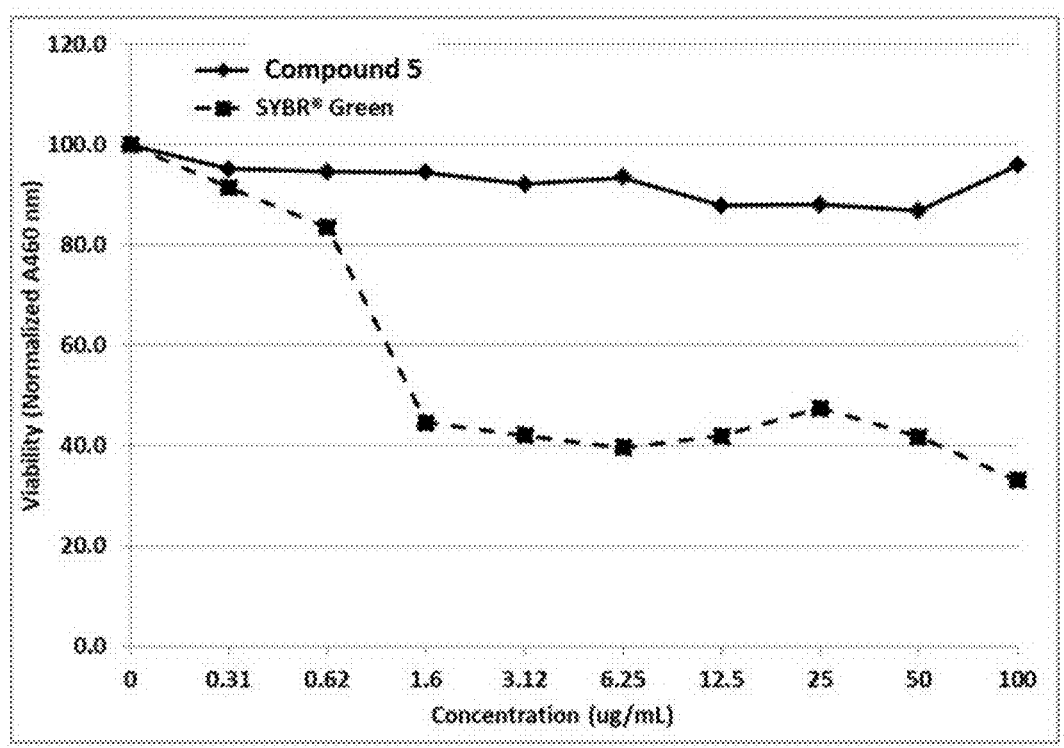
FIG. 7 shows a graphical representation of lack of cellular toxicity exhibited by increasing concentrations of Compound 5 versus SYBR Green. HeLa cells are plated in a 96-well plate (100 μL volume). Next day, to each 100 ul of cells is added 100 ul cyanine solution to make a series of cell samples with the final cyanine dye concentrations of 0, 0.31, 0.62, 1.6, 3.12, 6.25, 12.5, 25, 50, 100 ug/mL respectively. The cell viabilities are measured and plotted for each sample. Compound 5 exhibits significantly lower cell toxicity than SYBR Green. Compounds 4, 6, 7 and 10 also demonstrate lower cell toxicity compared to SYBR Green.

HeLa cells are plated in a 96-well plate (100 μL volume). Next day, to each 100 ul of cells is added 100 ul cyanine solution to make a serial cell samples with the final cyanine dye concentrations of 0, 0.31, 0.62, 1.6, 3.12, 6.25, 12.5, 25, 50, 100 ug/mL respectively (total volume is 200 μL for each sample), The cells are incubated in the cyanine-containing media for 24 hours. The cell viabilities are measured with Cell Meter™ Colorimetric WST-5' Cell Quantification Kit (AAT Bioquest) according to the product instruction. As shown in FIG. 7, Compound 5 has much lower cell toxicity than SYBR Green. Compounds 4, 6, 7 and 10 also demonstrate much lower cell toxicity than SYBR Green.

Example 23. Mutagenicities of Cyanine Dyes

Figure 8:
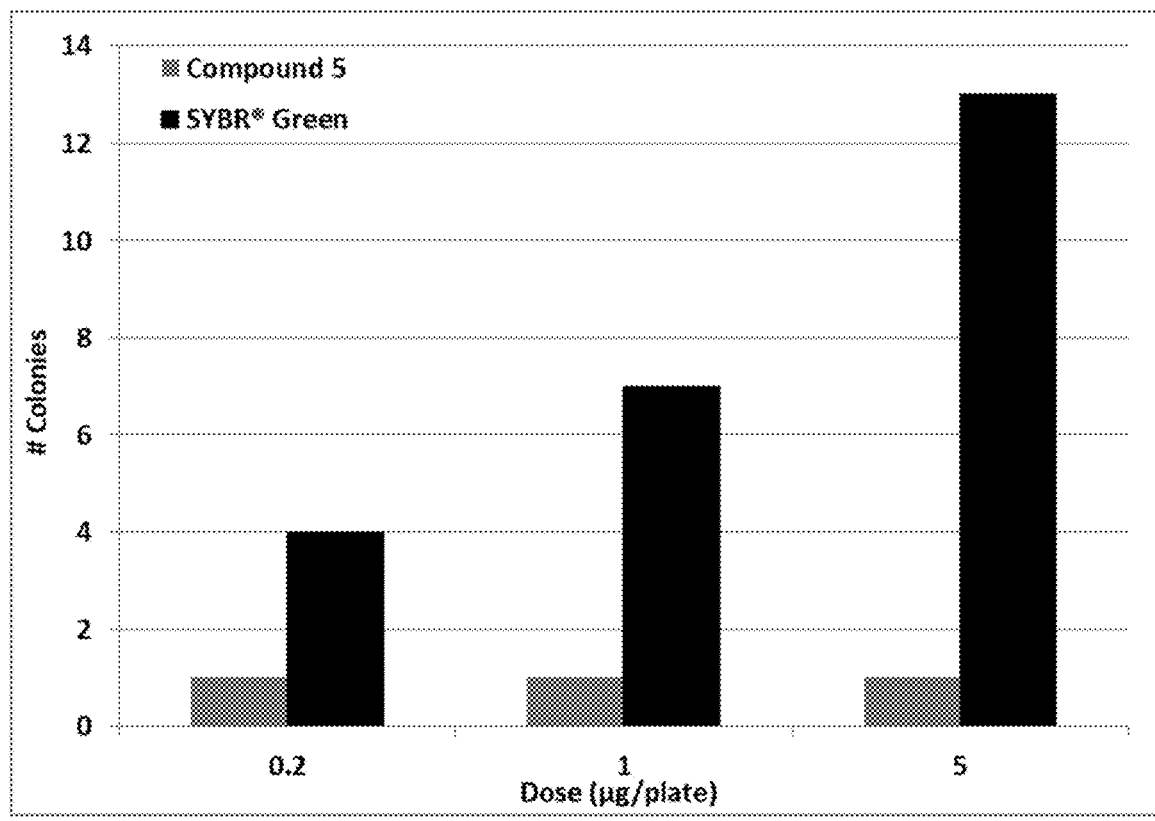
FIG. 8 shows a graphical representation of the results of a mutagenicity study using *S. typhimurium* bacteria with different amounts of Compound 5 versus SYBR Green. Mutagenicity tests are performed as described in Example 23. Compound 5 demonstrates significantly lower mutagenicity than SYBR Green. Compounds 4, 6, 7 and 10 also show significantly lower mutagenicity than SYBR Green.

Tubes of top agar are liquified and cooled to 55-60° C. 0.3 mL of histidine/biotin stock (Presque Isle Cultures) is added alongside 20 uL of S9 liver extract. (Sigma). To the top agar tubes 0.1 mL of *S. typhimurium* (Grown overnight at 37° C. in TSB culture) is added with 1 mL serological pipette. The mixture is thoroughly mixed by vortexing at low speed. The culture mixture is poured into the plates of the glucose-minimal salts agar plates. With the sterile loops, a disk on its edge is placed near the center of the plate. A serial concentrations of cyanine compounds (0.2, 1 and 5 ug/plate) are added to saturate the disk with a sterile Pasteur pipette. Sterile water is used with the same volume as a negative control. The plates are incubated for 48 hours at 37° C., and the colonies are counted near the disk. As shown in FIG. 8, Compound 5 demonstrates much low mutagenicity than SYBR Green. Compounds 4, 6, 7 and 10 also have much lower mutagenicity than SYBR Green.

Cyanine dyes are suitable for detecting the presence or absence of immobilized nucleic acids in a gel matrix, on a solid surface or in cells. As shown (but not limited to) in the above examples, useful methods of preparing any of various dyes described herein and useful methods of using any of these dyes have also been described. Useful kits suitable for determining immobilized nucleic acids, which comprises a suitable dye described herein, have also been described. Various modifications, processes, as well as numerous structures relating to the description herein may be applicable, as they are obvious to those of ordinary skill in the art, upon review of the specification. Various aspects and features may have been explained or described in relation to understandings, beliefs, theories, underlying assumptions, and/or working or prophetic examples, although it will be understood that any such understanding, belief, theory, underlying assumption, and/or working or prophetic example is not binding. Although the various aspects and features have been described with respect to various embodiments and examples herein, it will be understood that any of same is not limiting with respect to the full scope of the claims.

What is claimed is:

1. A cyanine compound, wherein the compound is of Formula 4a or 4b:

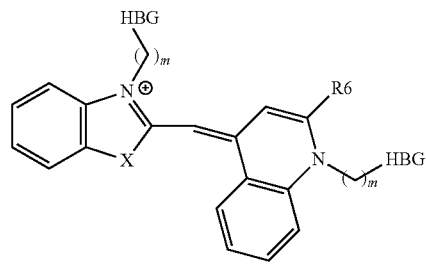

Formula 4a

Formula 4b

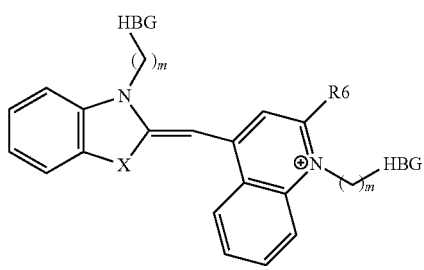

or a tautomer thereof, or a salt thereof, wherein:

each m is independently 2 to 6;

X is O, S, or NR20, wherein R20 is selected from hydrogen, optionally substituted alkyl, optionally substituted alkenyl, optionally substituted alkynyl, optionally substituted aryl, and optionally substituted heteroaryl;

R6 is selected from optionally substituted alkyl, halogen, carboxy, optionally substituted alkoxy, optionally substituted aryloxy, thiol, optionally substituted alkylthiol, optionally substituted arylthiol, azido, nitro, nitroso, cyano, amino, OH, a phosphonyl, a sulfonyl, a carbonyl, a boronyl, optionally substituted aryl, optionally substituted heteroaryl, optionally substituted phenyl, optionally substituted pyridyl, optionally substituted thiophenyl, and optionally substituted biphenyl; and each HBG is selected from —OH, —NH$_2$, —NHCOCH$_3$, —NHSOCH$_3$, —NHSO$_2$CH$_2$F, —NHSO$_2$CHF$_2$, and —NHSO$_2$CF$_3$.

2. The compound according to claim 1, wherein the compound is selected from:

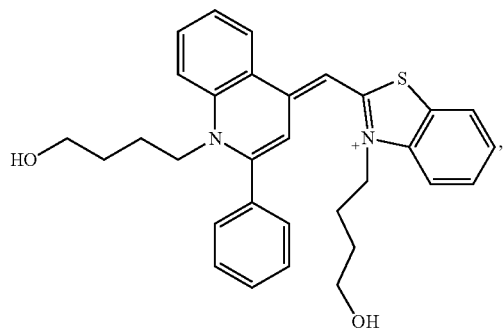

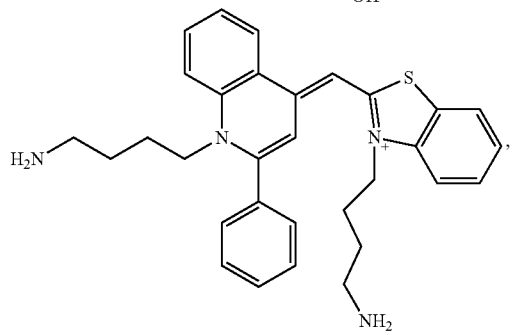

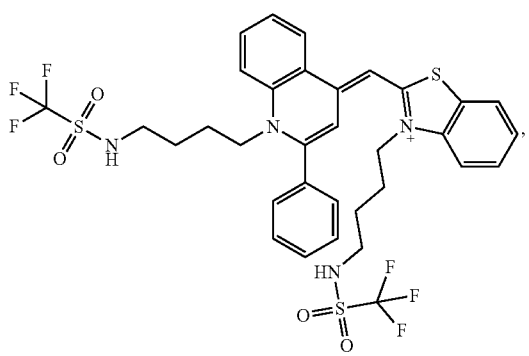

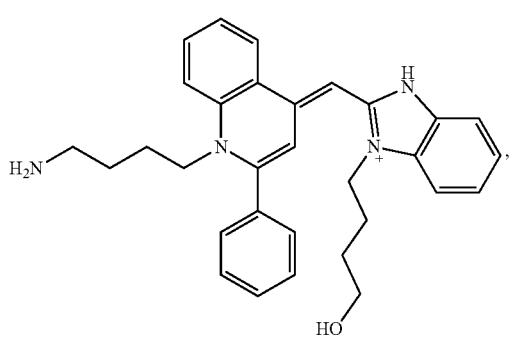

-continued

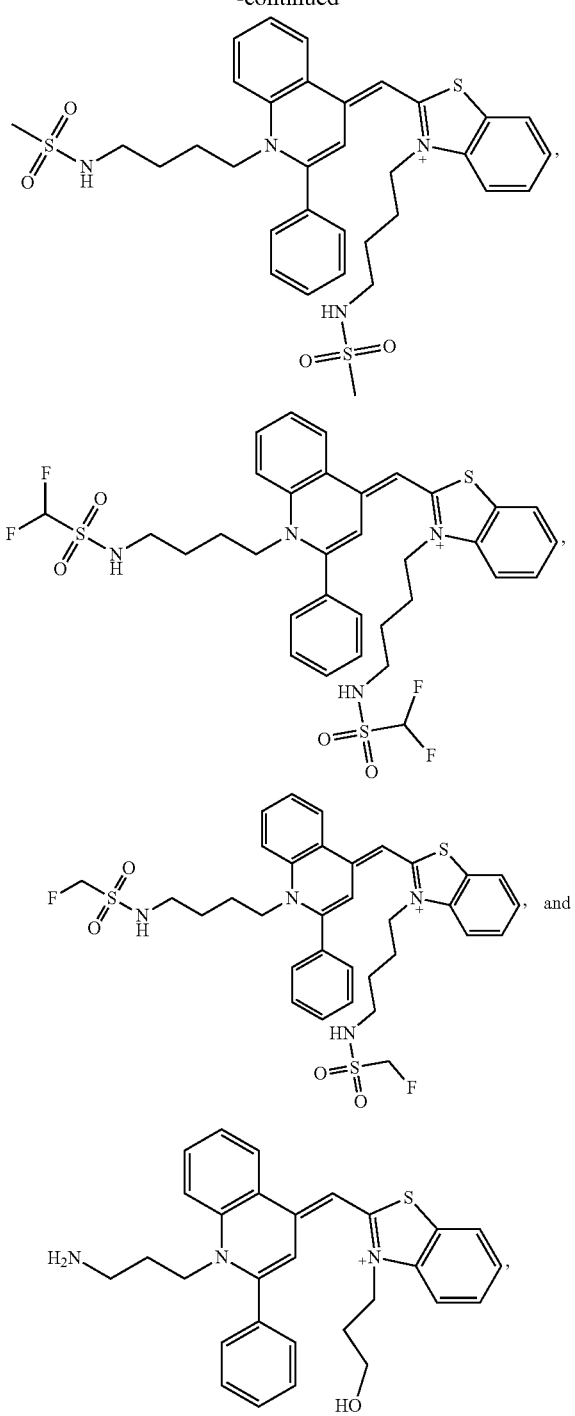

or a tautomer thereof, or a salt thereof.

3. A fluorescent complex comprising:
a nucleic acid; and
one or more cyanine compounds according to claim 1.

4. The compound according to claim 1, wherein
X is O or S; and
R6 is selected from optionally substituted phenyl, optionally substituted pyridyl, optionally substituted thiophenyl, and optionally substituted biphenyl.

5. The compound according to claim 4, wherein
each m is independently 3 or 4; and
each HBG is selected from —NH₂, —NHCOCH₃, —NHSO₂CH₃, —NHSO₂CH₂F, —NHSO₂CHF₂, and —NHSO₂CF₃.

6. The compound according to claim 5, wherein the compound is selected from:

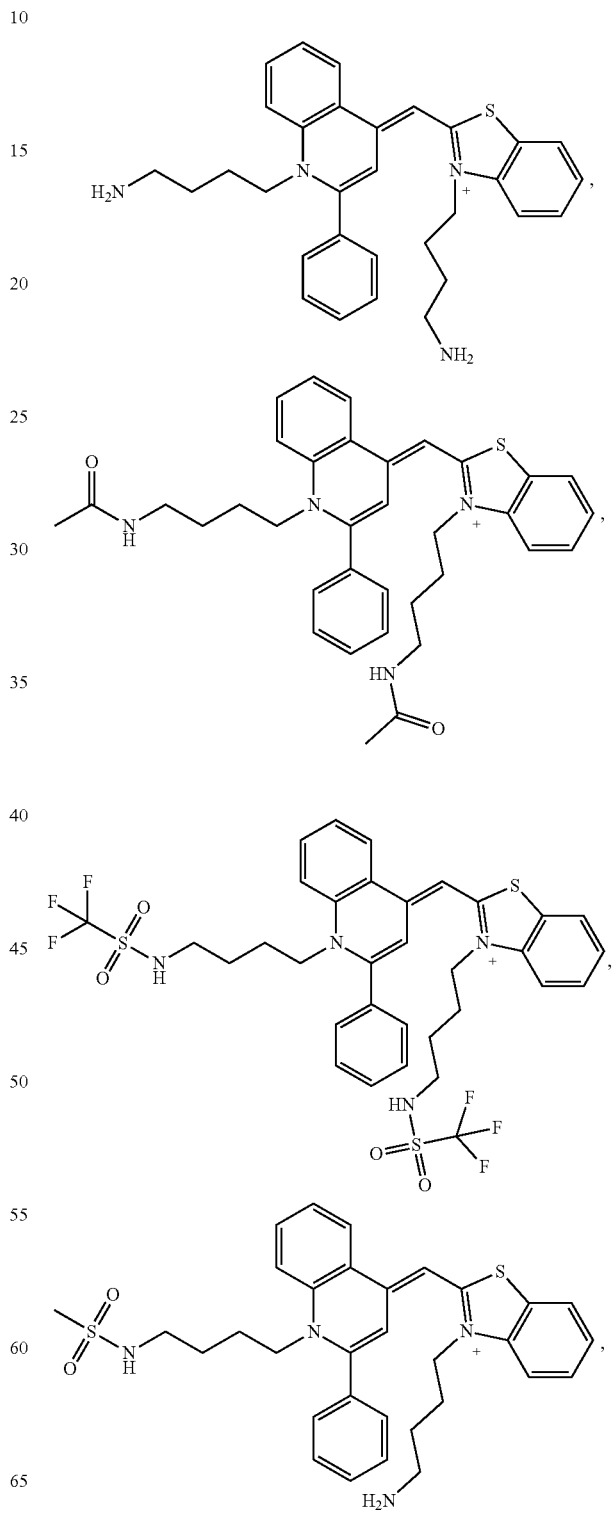

-continued

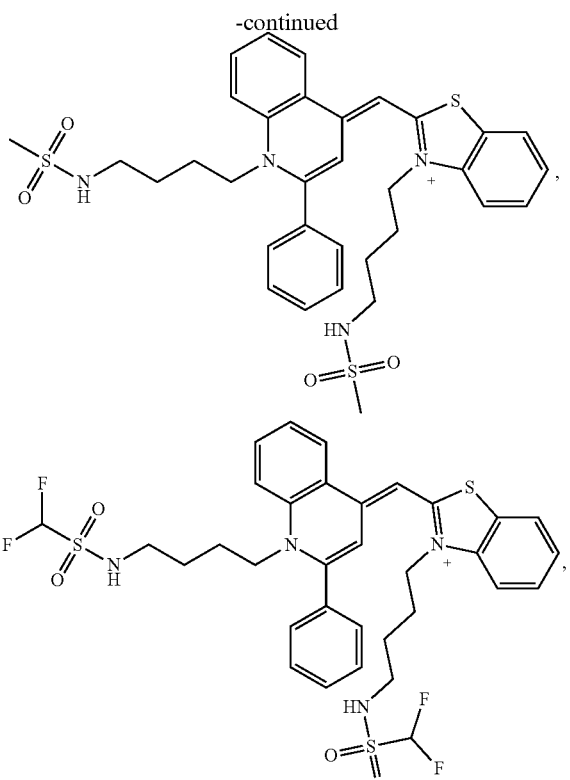

and

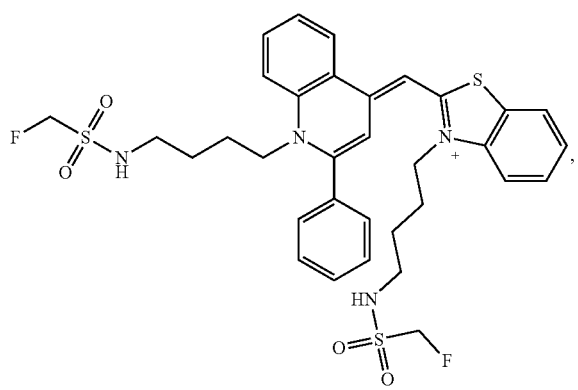

or a tautomer thereof, or a salt thereof.

7. The compound according to claim 1, wherein each m is independently 3 or 4.

8. The compound according to claim 1, wherein X is S.

9. The compound according to claim 1, wherein X is O.

10. The compound according to claim 1, wherein X is NR20.

11. The compound according to claim 1, wherein R6 is selected from an optionally substituted phenyl and pyridyl.

12. The compound according to claim 11, wherein R6 is an optionally substituted phenyl.

13. The compound according to claim 10 wherein R20 is selected from hydrogen, optionally substituted alkyl, optionally substituted aryl, and optionally substituted heteroaryl.

14. The compound according to claim 13, wherein R20 is selected is from hydrogen and an optionally substituted alkyl.

15. The compound according to claim 2, wherein the compound is

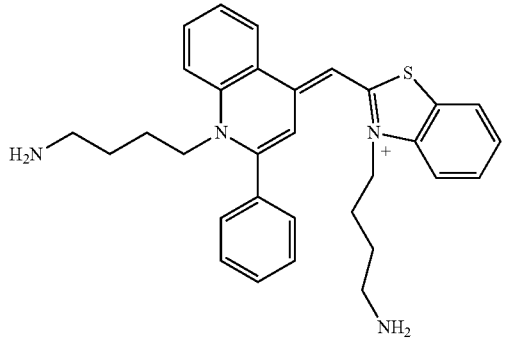

or a tautomer thereof, or a salt thereof.

16. A kit for detecting nucleic acids in a sample, the kit comprising:
   a) one or more cyanine compounds according to claim 1;
   b) one or more components selected from a buffer, a nucleic acid standard, a DNA or RNA ladder, a detergent, a matrix, and an instruction sheet concerning use of the kit for detecting nucleic acids in a sample.

17. The kit according to claim 16, wherein the compound is

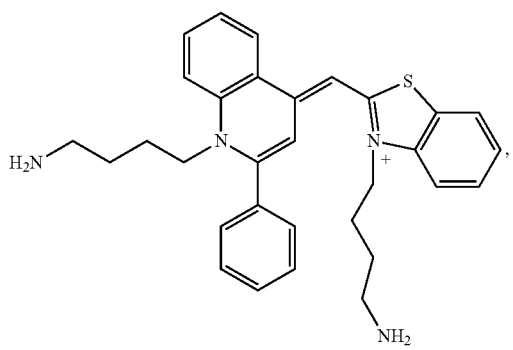

or a tautomer thereof, or a salt thereof.

18. A method of detecting nucleic acids in a sample, comprising:
   a) contacting a sample that contains a nucleic acid with the compound according to claim 1;
   b) incubating the contacted sample under conditions sufficient for the compound to associate with the nucleic acid in the sample to produce a fluorescent nucleic acid-dye complex; and
   c) detecting a fluorescent signal of the nucleic acid-dye complex.

19. The method according to claim 18, wherein the compound is
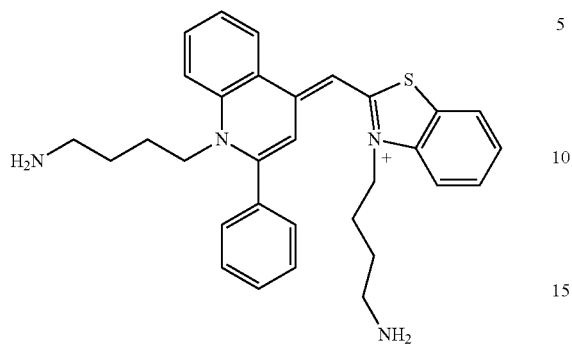
or a tautomer thereof, or a salt thereof.
20. A cyanine compound selected from:
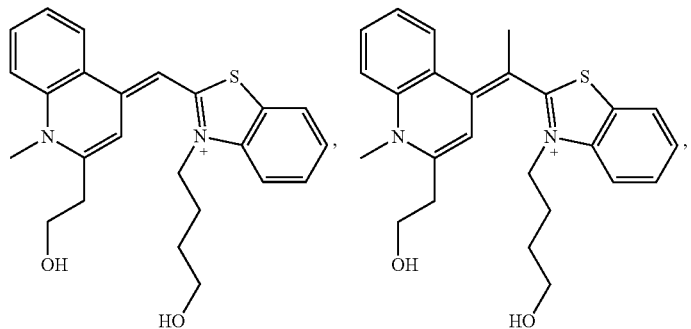
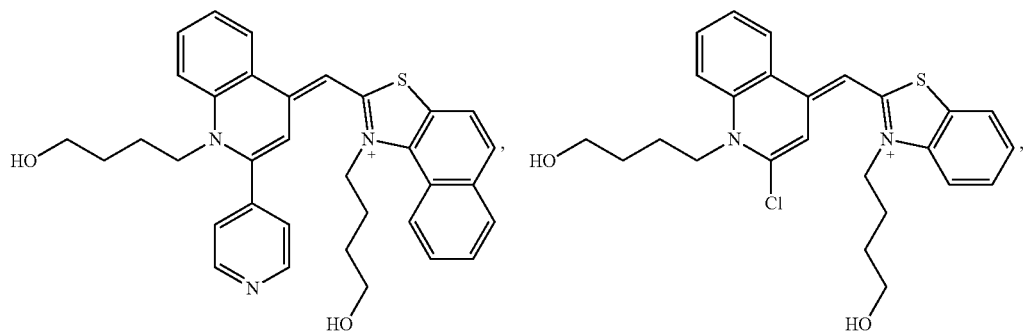
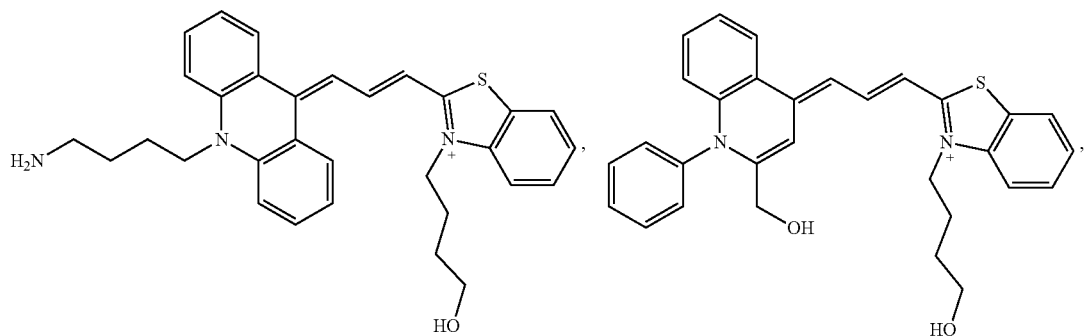

-continued
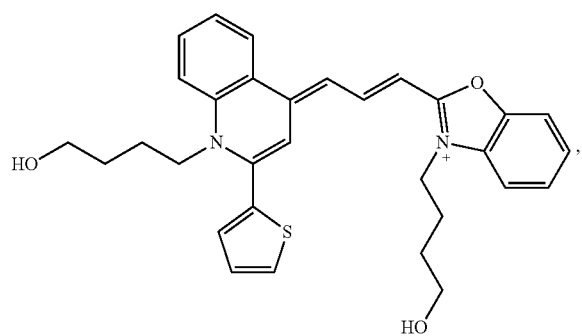
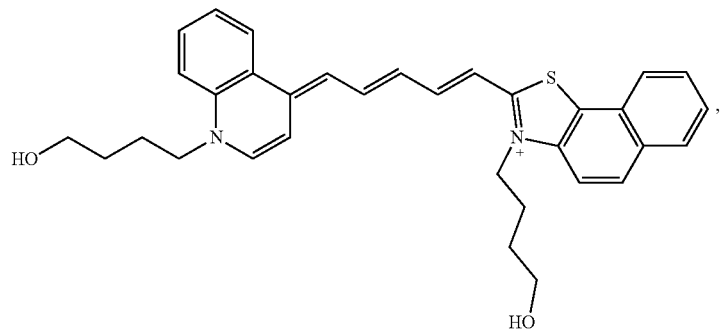
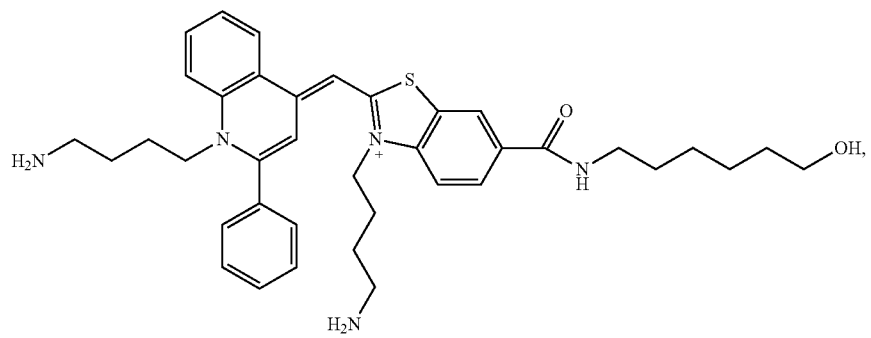
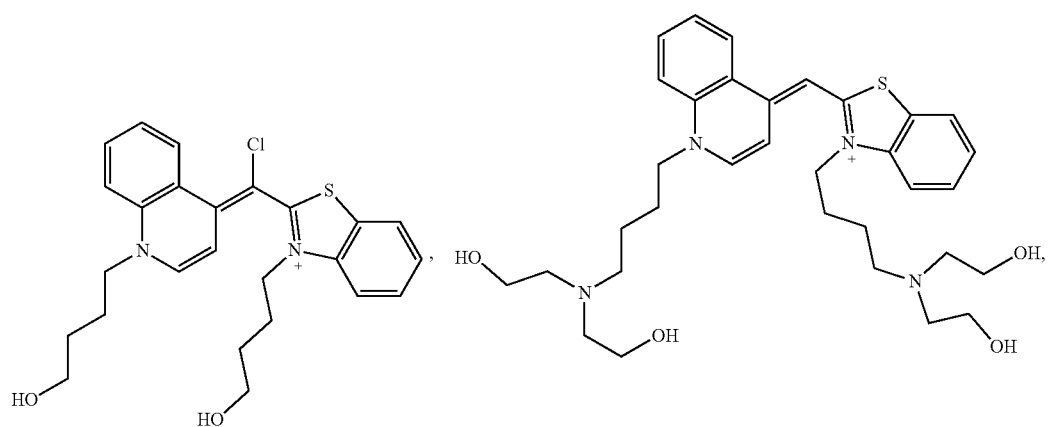

77 78
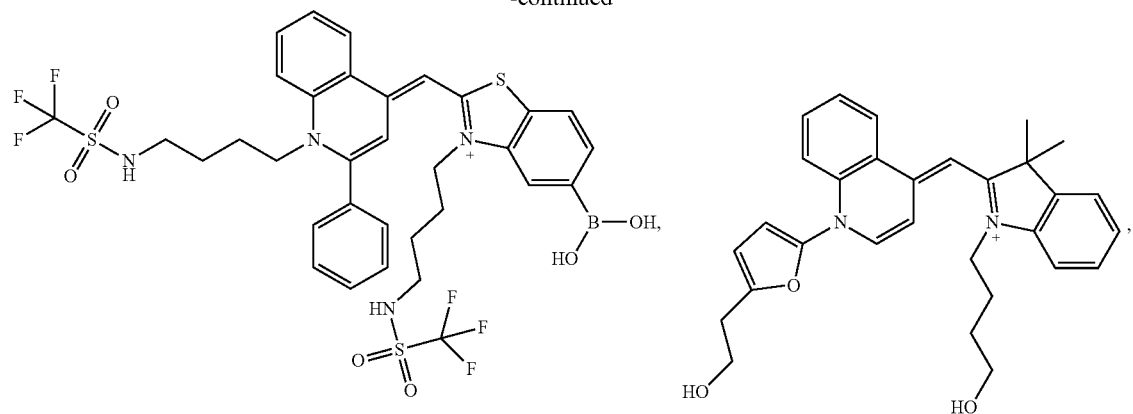
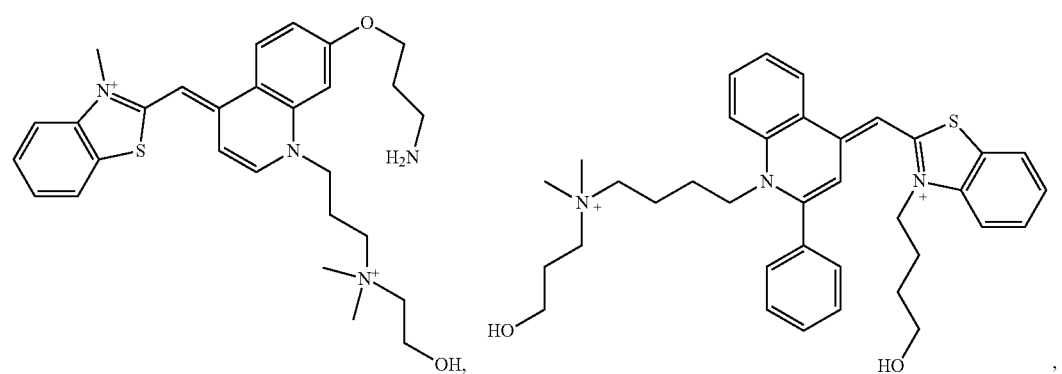
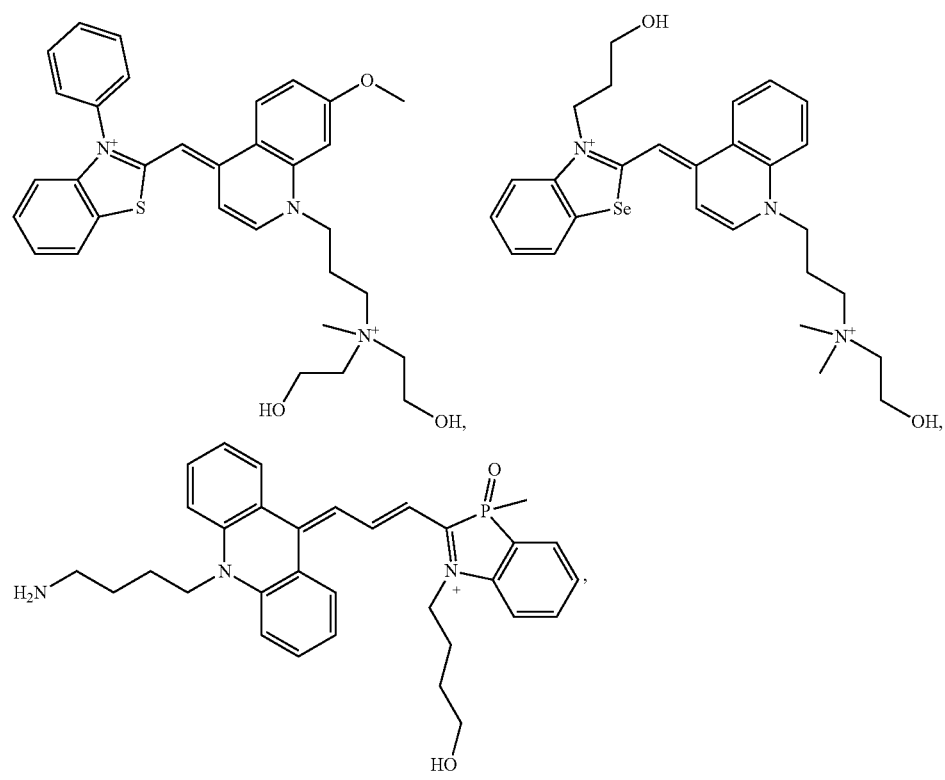

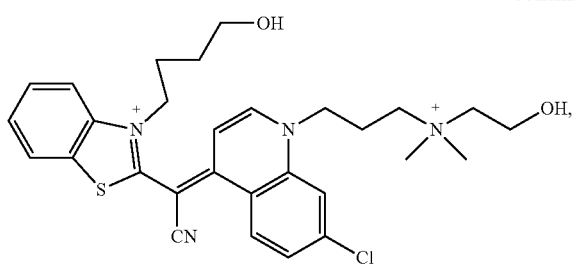
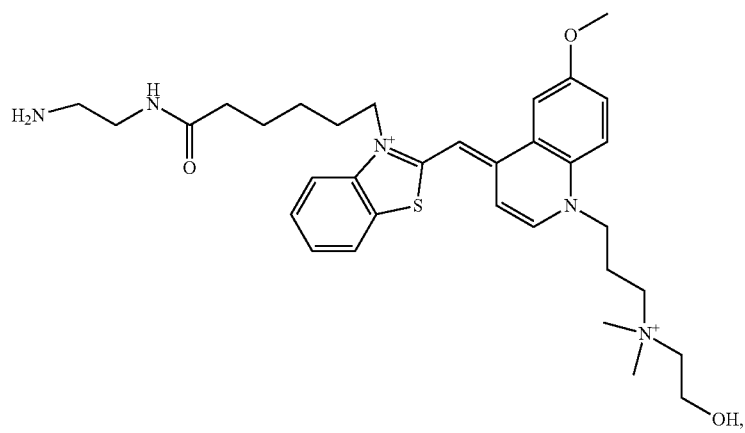
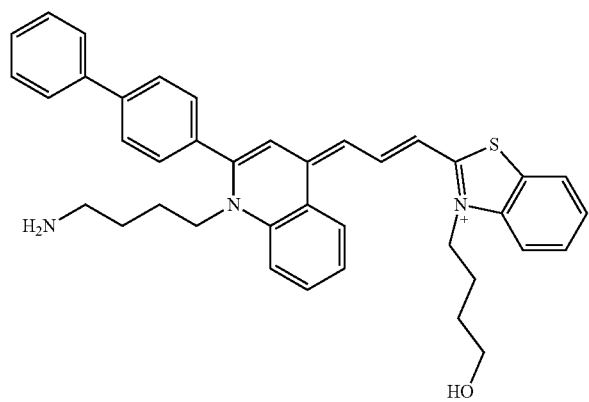
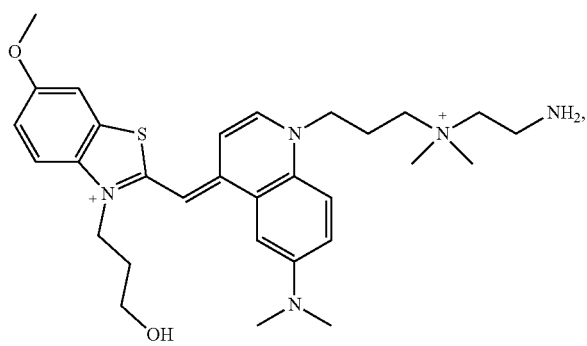

-continued
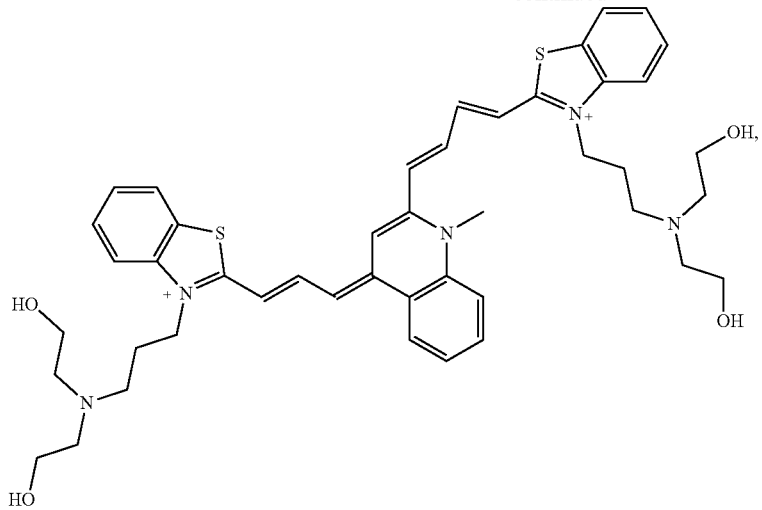
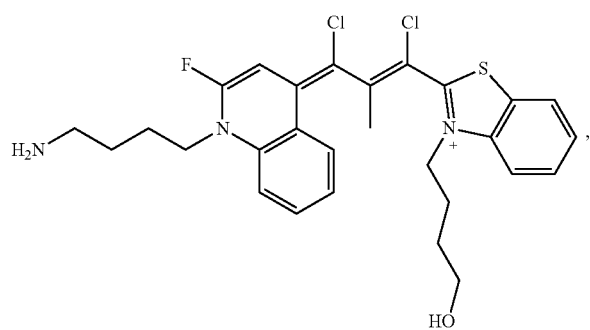
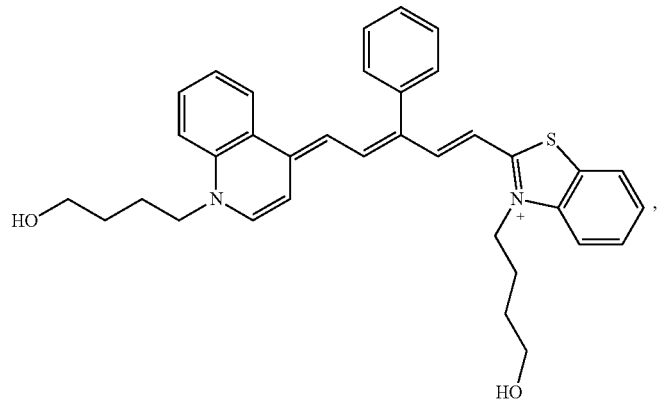
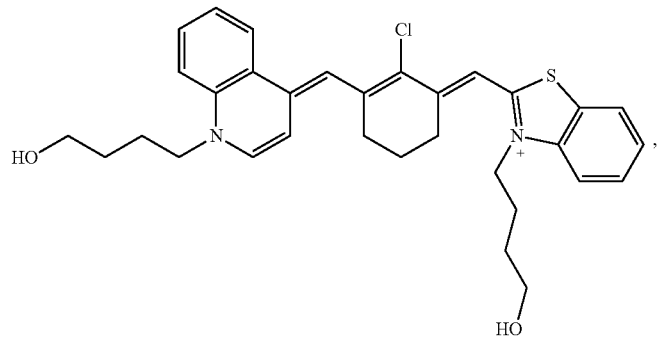

-continued
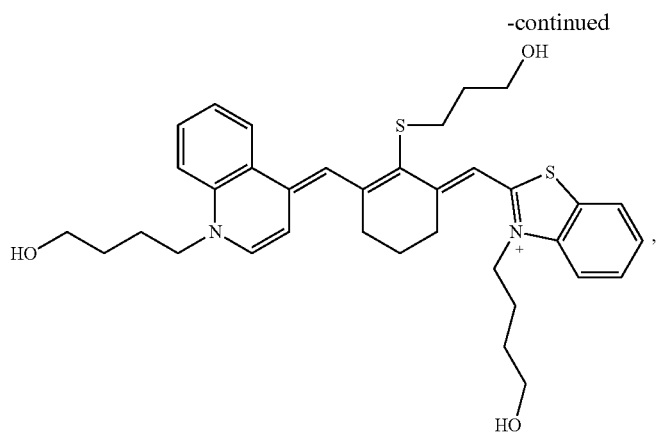
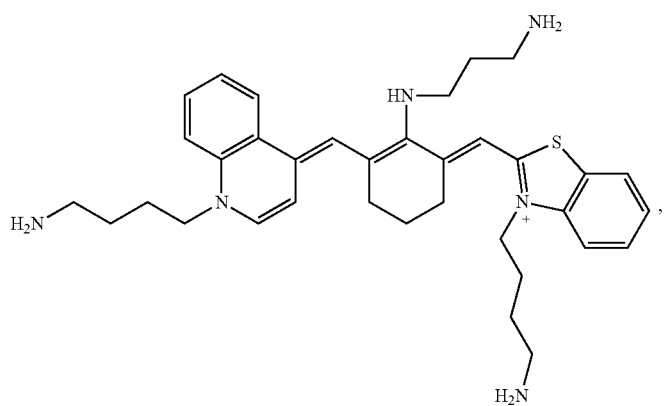
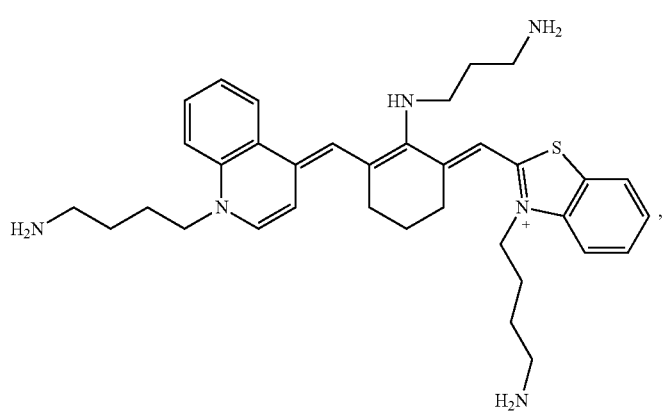
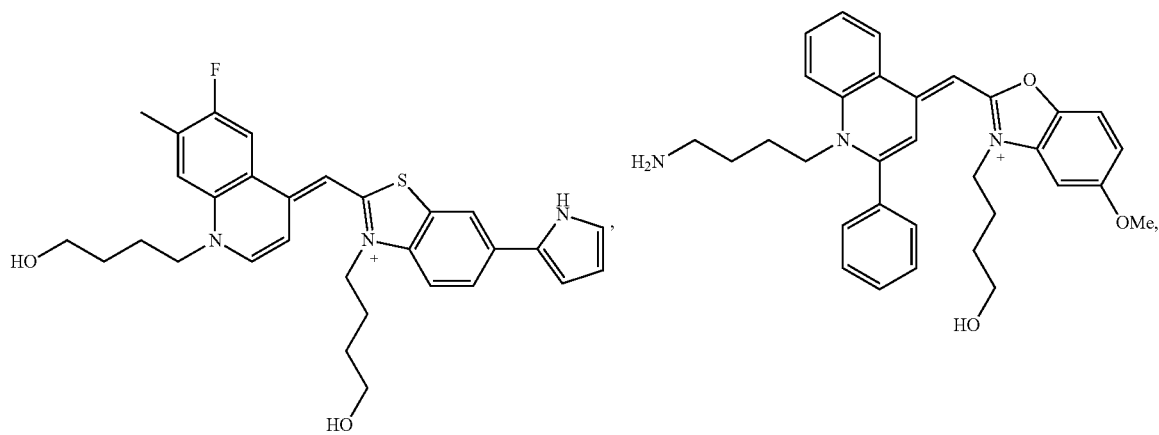

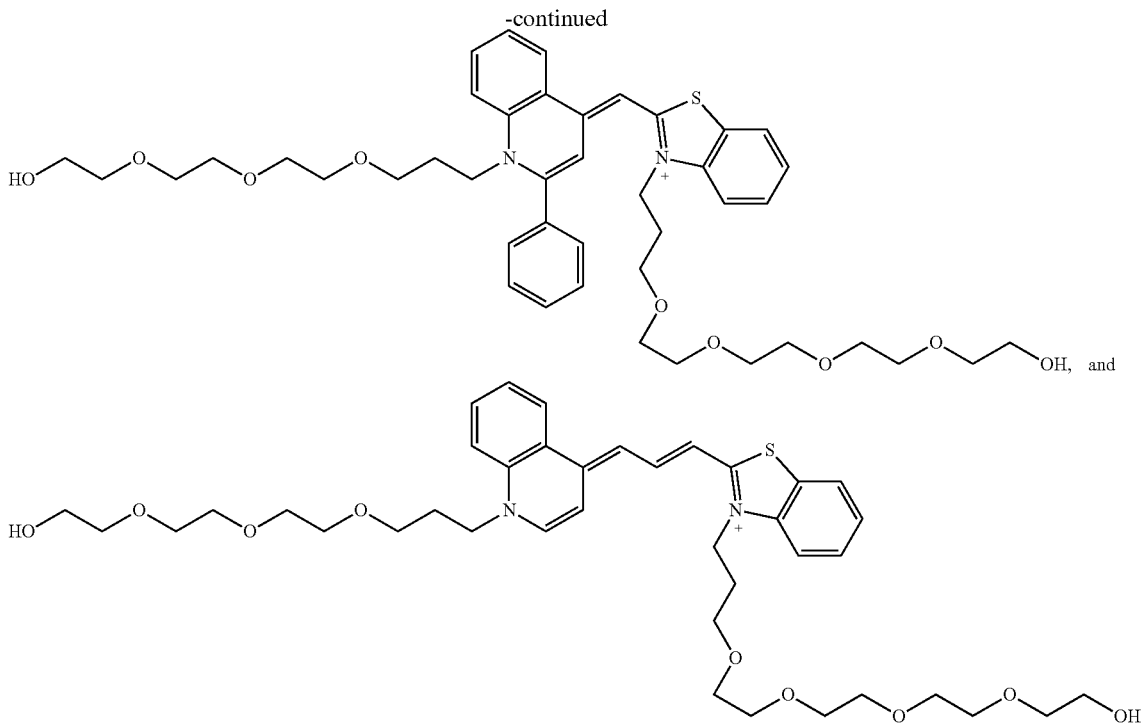

or a tautomer thereof, or a salt thereof.

21. A fluorescent complex comprising:
a nucleic acid; and
one or more cyanine compounds according to claim 20.

22. A kit for detecting nucleic acids in a sample, the kit comprising:

a) one or more cyanine compounds according to claim 20;
b) one or more components selected from a buffer, a nucleic acid standard, a DNA or RNA ladder, a detergent, a matrix, and an instruction sheet concerning use of the kit for detecting nucleic acids in a sample.

* * * * *

UNITED STATES PATENT AND TRADEMARK OFFICE
CERTIFICATE OF CORRECTION

PATENT NO. : 12,169,166 B2
APPLICATION NO. : 17/176847
DATED : December 17, 2024
INVENTOR(S) : Diwu et al.

Page 1 of 1

It is certified that error appears in the above-identified patent and that said Letters Patent is hereby corrected as shown below:

In the Claims

In Column 67, in Claim 1, Line 36, delete "–NHSOCH$_3$," and insert -- –NHSO$_2$CH$_3$, --, therefor.

Signed and Sealed this
Eighteenth Day of March, 2025

Coke Morgan Stewart
*Acting Director of the United States Patent and Trademark Office*